United States Patent
Nii et al.

(10) Patent No.: US 8,039,630 B2
(45) Date of Patent: Oct. 18, 2011

(54) CATIONIC COMPOUND, DYE COMPOUND AND METHOD OF USING THE SAME, AND OPTICAL INFORMATION RECORDING MEDIUM

(75) Inventors: Kazumi Nii, Kanagawa (JP); Tatsuo Mikami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 833 days.

(21) Appl. No.: 11/917,045

(22) PCT Filed: Nov. 9, 2006

(86) PCT No.: PCT/JP2006/322365
§ 371 (c)(1),
(2), (4) Date: Dec. 10, 2007

(87) PCT Pub. No.: WO2007/055273
PCT Pub. Date: May 18, 2007

(65) Prior Publication Data
US 2009/0130367 A1      May 21, 2009

(30) Foreign Application Priority Data
Nov. 11, 2005   (JP) ................................. 2005-327009

(51) Int. Cl.
*C07D 401/00*   (2006.01)
*C07D 213/22*   (2006.01)
(52) U.S. Cl. ........................................ 546/256; 546/257
(58) Field of Classification Search .................. None
See application file for complete search history.

(56) References Cited

U.S. PATENT DOCUMENTS

| | | | |
|---|---|---|---|
| 4,968,593 A | 11/1990 | Inagaki et al. | |
| 6,020,105 A | 2/2000 | Wariishi | |
| 6,541,092 B2 | 4/2003 | Shibata et al. | |
| 6,646,132 B2 | 11/2003 | Morishima et al. | |
| 6,849,316 B2 | 2/2005 | Wariishi et al. | |
| 2002/0009669 A1 | 1/2002 | Morishima et al. | |
| 2007/0020562 A1 | 1/2007 | Akiba et al. | |

FOREIGN PATENT DOCUMENTS

| | | | |
|---|---|---|---|
| JP | 57-057779 A | 4/1982 | |
| JP | 63-209995 A | 8/1988 | |
| JP | 10-109475 A | 4/1998 | |
| JP | 10-297103 A | 11/1998 | |
| JP | 2000-52658 A | 2/2000 | |
| JP | 2002-59652 A | 2/2002 | |
| JP | 2002-249674 A | 9/2002 | |
| JP | 2004-188968 A | 7/2004 | |

OTHER PUBLICATIONS

Doddi, Giancarlo et al, "Template Effects in the Self-Assembly of a [2] Rotaxane and a [2] Pseudorotaxane with the Same Binding Sites in the Linear Component", Journal of Organic Chemistry, 66 (14), 2001, pp. 4950-4953.
Nambu, Y. et al, "Design of novel viologens bearing benzophenone structure for effective photoinduced electron transfer", Chem. Funct. Dyes, Proc. Int. Symp., 2nd, 1993, pp. 145-148.
Extended European Search Report dated Dec. 6, 2010 on European Application No. 06823252.9.

*Primary Examiner* — Janet Andres
*Assistant Examiner* — Heidi Reese
(74) *Attorney, Agent, or Firm* — Sughrue Mion, PLLC

(57) ABSTRACT

The present invention relates to a cationic compound denoted by the general formula (I). In general formula (I), $Ar^1$ and $Ar^2$ each independently denote an optionally substituted aryl group or aromatic heterocyclic group, $L^1$ denotes a single bond or a divalent linkage group, with at least one from among $Ar^1$, $Ar^2$ and $L^1$ comprising one or more onium cations; $R^3$ and $R^4$ each independently denote a substituent and may form a ring with a benzene ring substituted; m3 and m4 each independently denote an integer ranging from 0 to 4, and plural $R^3$s and $R^4$s may be identical or different from each other when m3 and m4 are an integer ranging from 2 to 4.

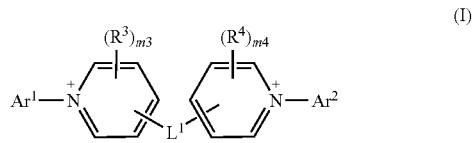

12 Claims, 2 Drawing Sheets

[Fig. 1]
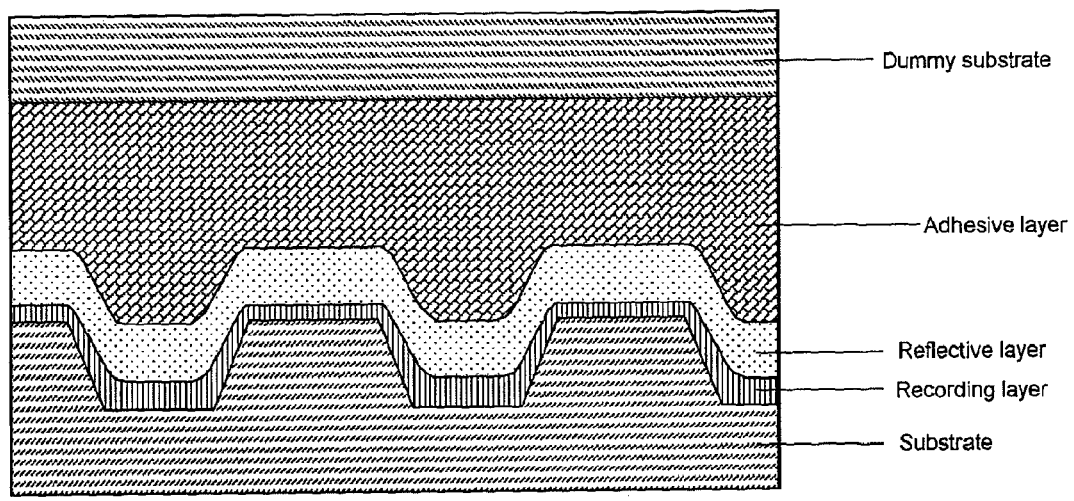

[Fig. 2]
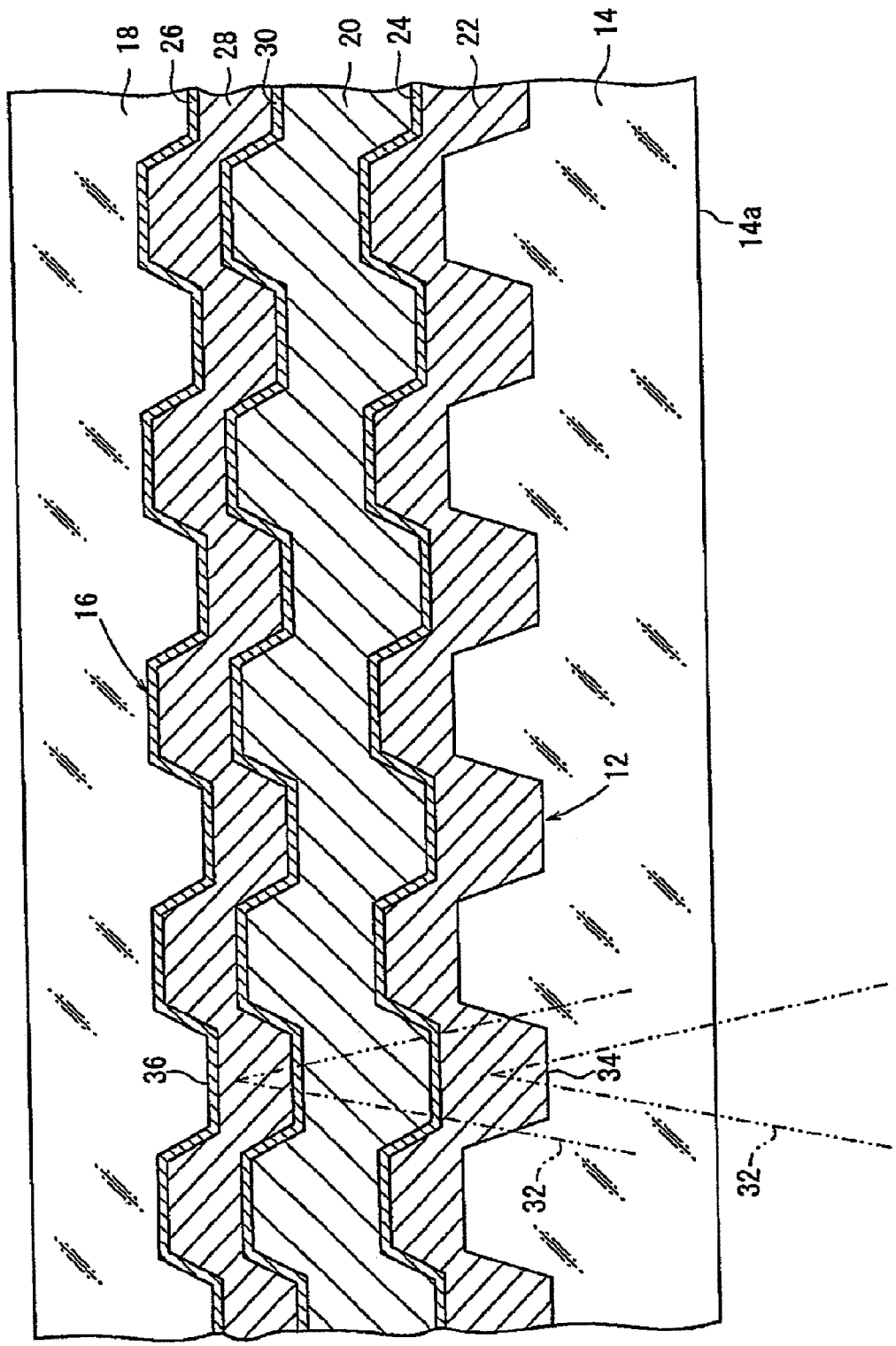

CATIONIC COMPOUND, DYE COMPOUND AND METHOD OF USING THE SAME, AND OPTICAL INFORMATION RECORDING MEDIUM

TECHNICAL FIELD

The present invention relates to a novel cationic compound capable of providing a dye compound suitable for use as a dye for a recording layer of an optical information recording medium. The present invention further relates to a dye compound comprising the cationic compound, a method of using the same, and an optical information recording medium comprising the dye compound as a dye for a recording layer. The dye compound is suitable as dye for a recording layer of heat-mode information recording media, such as recordable digital versatile disks (DVD-R), on which information is recorded with a visible laser beam.

BACKGROUND TECHNIQUE

The recordable CD (so-called "CD-R") is known as an information recording medium (optical disk) on which information can be recorded just once with a laser beam. It affords an advantage in that smaller quantities of CDs can be provided at more reasonable cost and more rapidly than when manufacturing conventional CDs. Demand for it has increased as personal computers have become widespread. The typical configuration of a CD-R information recording medium comprises a transparent disklike substrate on which are sequentially stacked a recording layer comprised of an organic dye, a reflective layer comprised of a metal such as gold, and a protective layer made of resin. Data are recorded on an optical disk by irradiating a near infrared laser beam (normally, a laser beam with a wavelength in the vicinity of 780 nm) onto the recording layer, causing it to undergo localized thermal deformation. Data are read (reproduced) by irradiating a laser beam of the same wavelength as the laser beam for recording and detecting differences in the reflectance of portions of the recording layer that have been thermally deformed (recorded portions) and portions that have not been deformed (unrecorded portions).

As the performance of personal computers has improved and the speed of the Internet has increased in recent years, image data (particularly animation and the like) comes to be handled, requiring higher capacity information recording media. An optical disk known as a recordable digital variable disk (so-called "DVD-R"), in which a narrowed laser beam of shorter wavelength is used to increase the recording density, is being sold as information recording media of higher recording density. This optical disk is manufactured in a configuration comprising two disks, each of which sequentially comprises a transparent disklike substrate that is 120 mm or 80 mm in diameter, on which are formed pregrooves with a track pitch of 0.8 micrometer, which is narrower than the 1.6 micrometers of a CD-R; a recording layer comprising dye; and, normally, a reflective layer and a protective layer over the recording layer. Alternatively, the configuration may comprise such a disk, adhered by means of adhesive to a disklike protective substrate of roughly identical size, with the recording layer to the inside. Recording and reproduction on a DVD-R are conducted by irradiation with a visible laser beam (normally, a laser beam with a wavelength falling within a range of 600 nm to 700 nm), permitting higher density recording than is possible with a CD-R optical disk. An optical disk with specifications similar to those of the DVD-R is now being sold as the DVD+R.

The recordable DVD information recording medium permits the recording of several times the quantity of data of a conventional CD-R. Since high recording sensitivity and, in particular, the rapid processing of large amounts of information are required, a low error rate is desirable in high-speed recording. The recording layer comprising dye generally has low stability over time to heat or light. Thus, the development of a recording layer capable of maintaining stable performance for extended periods to heat or light is desirable.

In a recordable DVD, the reduction in recording time, that is, the increase in recording speed, is desirable as in a CD-R. There is a need for the recordable DVD to increase the sensitivity and improve the decreasing writing precision (deterioration in the form of jitter) due to increase the writing laser power.

Japanese Unexamined Patent Publication (KOKAI) Showa No. 63-209995 [Patent Reference 1] discloses a CD-R information recording medium in which a recording layer comprised of an oxonol dye is provided on a substrate. The use of such a dye compound is described as maintaining stable recording reproduction characteristics for an extended period, and an oxonol dye compound into which ammonium is introduced in the form of a salt is described. Japanese Unexamined Patent Publication (KOKAI) Heisei No. 10-109475 [Patent Reference 2] describes bipyridinium as being effective in enhancing resistance to light as an ammonium introduced in the form of a salt. It is further stated that the dye is not limited to oxonol, and that a variety of dyes are effective. Japanese Unexamined Patent Publication (KOKAI) Heisei No. 10-297103 [Patent Reference 3] describes that an oxonol dye having a biologen-paired salt is effective. Japanese Unexamined Patent Publication (KOKAI) No. 2000-52658 [Patent Reference 4] and Japanese Unexamined Patent Publication No. 2002-249674 [Patent Reference 5] describe oxonol dye compounds exhibiting high resistance to light and durability and providing optical information recording media with good recording characteristics. Japanese Unexamined Patent Publication (KOKAI) No. 2002-59652 [Patent Reference 6] describes a technique of mixing two dyes of differing sensitivity, with oxonol dyes among them. Japanese Unexamined Patent Publication (KOKAI) No. 2004-188968 [Patent Reference 7] discloses bis-oxonol dyes of specific structure.

DISCLOSURE OF THE INVENTION

In recent years, DVD-R DL (double layer) media having a double-layered recording surface, each surface having a capacity of 8.5 GB, about 1.8 times that of the single layer media (4.7 GB), have been developed. In the same manner as for the single-layer DVD-R, an investigation has been made into reducing the recording time. Since DVD-R DL media have two stacked dye layers, the properties required of the dye constituting each layer with regard to sensitivity, reflectance, jitter, and the like are stricter than for the dyes employed in single-layer media, and there is need for dyes of higher performance.

Further, in addition to the above properties, good manufacturing suitability, such as solubility during the preparation of dye coating liquids, dissolution stability of coating liquids over time, and coating properties when employing high-concentration coating solutions (coating film smoothness) are also required of the recording layer dyes of optical information recording media.

Under such circumstances, the present invention was devised with the object of providing a novel dye capable of providing an optical information recording medium exhibiting good sensitivity, jitter, and reflectance, as well as having good suitably to manufacturing, in particular, exhibiting good characteristics as a dye for DVD-R media.

The present inventors conducted extensive research into achieving the above-stated object, resulting in the discovery that a dye compound formed from an anion and a novel cationic compound having three or more cation moieties per molecule yielded an optical information recording medium having good sensitivity, jitter, and reflectance; that this dye compound had good solubility during dye coating liquid preparation and afforded good dissolution stability of coating liquids over time; and yielded a good coating surface with the coating of a high concentration coating solution. The present invention was devised on this basis.

That is, the present invention that is a means for achieving the above-stated object relates to a cationic compound denoted by the following general formula (I).

[Chem. 1]

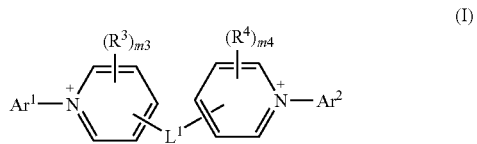

(I)

[In general formula (I), $Ar^1$ and $Ar^2$ each independently denote an optionally substituted aryl group or aromatic heterocyclic group, $L^1$ denotes a single bond or a divalent linkage group, with at least one from among $Ar^1$, $Ar^2$ and $L^1$ comprising one or more onium cations; $R^3$ and $R^4$ each independently denote a substituent and may form a ring with a benzene ring substituted; m3 and m4 each independently denote an integer ranging from 0 to 4, and plural $R^3$s and $R^4$s may be identical or different from each other when m3 and m4 are an integer ranging from 2 to 4.]

In the above general formula (I), $Ar^1$ can be denoted by:

[Chem. 2]

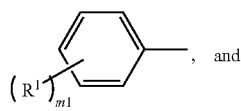, and $Ar^2$ can be denoted by:

[Chem. 3]

.

[In the above, $R^1$ and $R^2$ each independently denote a substituent and may form a ring with a benzene ring substituted; one of m1 and m2 denotes an integer ranging from 0 to 5 and the other denotes an integer ranging from 1 to 5, and plural $R^1$s and $R^2$s may be identical or different from each other when m1 and m2 are an integer ranging from 2 to 5.]

Furthermore, in the above general formula (I), at least one from among $R^1$ and $R^2$ can denote a substituent comprising a nitrogen cation, and $L^1$ can be a single bond. The above nitrogen cation can be a tetra-substituted nitrogen atom cation or nitrogen atom-containing aromatic heterocyclic cation, and the above nitrogen atom-containing aromatic heterocyclic cation is a pyridinium cation, imidazolium cation, thiazolium cation, oxazolium cation, or iminium cation.

Furthermore, in the above general formula (I), $L^1$ can be denoted by:

[Chem. 4]

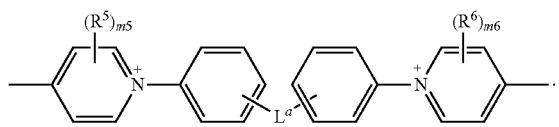

[In the above, $R^5$ and $R^6$ each independently denote a substituent; m5 and m6 each independently denote an integer ranging from 0 to 4, and plural $R^5$s and $R^6$s may be identical or different from each other when m5 and m6 are an integer ranging from 2 to 4.]

In addition, the compound denoted by the above general formula (I) can be a compound denoted by the following general formula (IV).

[Chem. 5]

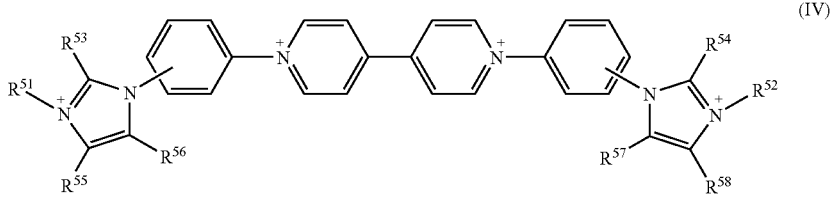

(IV)

[In general formula (IV), $R^{51}$ and $R^{52}$ each independently denote a hydrogen atom or alkyl group; $R^{53}$, $R^{54}$, $R^{55}$, $R^{56}$, $R^{57}$, and $R^{58}$ each independently denote a hydrogen atom, alkyl group, aryl group, or aromatic heterocyclic group, it being permissible for $R^{55}$ and $R^{56}$, and $R^{57}$ and $R^{58}$, to be linked, forming a five or six-membered ring, and $R^{51}$, $R^{52}$, $R^{53}$, $R^{54}$, $R^{55}$, $R^{56}$, $R^{57}$, and $R^{58}$ each may be further substituted.]

Another aspect of the present invention relates to a dye compound comprising the cationic compound of the present invention mentioned above and an anion in an amount capable of neutralizing the charge of the above cationic compound. In this dye compound, the above anion can be an anionic dye, the above anionic dye can be an oxonol dye, and the above oxonol dye can be denoted by the following general formula (V).

[Chem. 6]

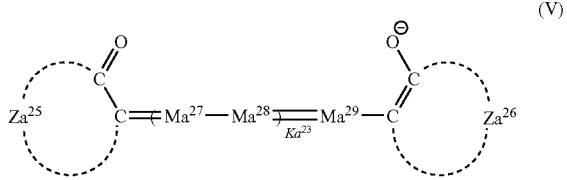
(V)

[In general formula (V), $Za^{25}$ and $Za^{26}$ each independently denote an atom group forming an acidic nucleus; $Ma^{27}$, $Ma^{28}$, and $Ma^{29}$ each independently denote a substituted or unsubstituted methine group; $Ka^{23}$ denotes an integer ranging from 0 to 3, and plural $Ma^{27}$s and $Ma^{28}$s may be identical or different from each other when $Ka^{23}$ is 2 or 3.]

Furthermore, the above oxonol dye can be denoted by the following general formula (VI).

[Chem. 7]

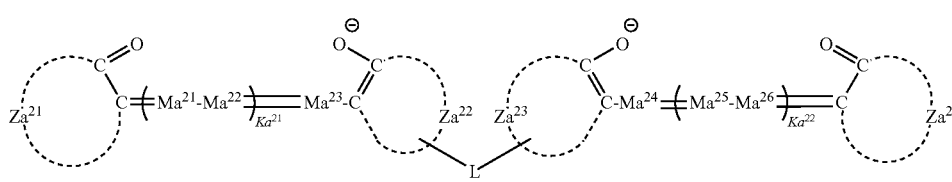
(VI)

[In general formula (VI), $Za^{21}$, $Za^{22}$, $Za^{23}$, and $Za^{24}$ each independently denote an atom group forming an acidic nucleus; $Ma^{21}$, $Ma^{22}$, $Ma^{23}$, $Ma^{24}$, $Ma^{25}$, and $Ma^{26}$ each independently denote a substituted or unsubstituted methine group; L denotes a divalent linkage group that does not form a pi-conjugation with two bonds, and plural $Ma^{21}$s, $Ma^{22}$s, $Ma^{25}$s, and $Ma^{26}$s may be identical or different from each other when $Ka^{21}$ and $Ka^{22}$ are 2 or 3.]

The present invention further relates to an optical information recording medium comprising a recording layer on a substrate, wherein the above recording layer comprises the dye compound of the present invention mentioned above. This optical information recording medium can be a recordable optical information recording medium, or can be a DVD-R optical information recording medium.

The present invention further relates to a method of using the dye compound of the present invention mentioned above as a dye for a recording layer of an optical information recording medium. In this method, the above optical information recording medium can be a recordable optical information recording medium, or can be a DVD-R optical information recording medium.

According to the present invention, optical information recording media exhibiting excellent sensitivity, jitter, and reflectance can be provided. Furthermore, the dye compound of the present invention has excellent solubility during the preparation of dye coating liquids and dissolution stability of coating liquids over time, permitting the formation of a recording layer with good coating surface state even when the recording layer is formed by coating a high-concentration coating solution.

[Cationic Compound]

The cationic compound of the present invention is a cationic compound denoted by the following general formula (I).

[Chem. 8]

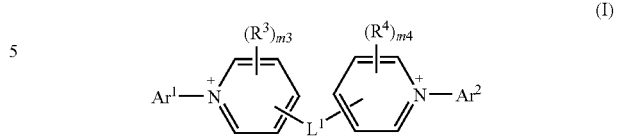
(I)

The cationic compound of the present invention comprises three or more cationic moieties per molecule, and together with an anionic moiety, forms a dye compound that is useful as a dye for a recording layer of an optical information recording medium. The cationic compound of the present invention will be described in detail below.

General Formula (I)

In general formula (I), $Ar^1$ and $Ar^2$ each independently denote an optionally substituted aryl group or aromatic heterocyclic group, with at least one from among $Ar^1$, $Ar^2$ and $L^1$ comprising one or more onium cations. The aryl group denoted by $Ar^1$, $Ar^2$ preferably has 6 to 30, more preferably 6 to 20, and further preferably, 6 to 12 carbon atoms. Examples are phenyl groups, p-methylphenyl groups, naphthyl groups, and anthranyl groups.

The aromatic heterocyclic group denoted by $Ar^1$ and $Ar^2$ preferably has 1 to 30, more preferably 1 to 20, and further preferably, 1 to 12 carbon atoms. The hetero atoms contained in the aromatic heterocyclic group can be nitrogen atoms, oxygen atoms, and sulfur atoms, for example. Specific examples of the aromatic heterocyclic group are pyrrole groups, pyrazole groups, imidazole groups, pyridine groups, furan groups, thiophene groups, oxazole groups, thiazole groups, benzo condensed ring products thereof, and heterocyclic condensed ring products thereof. It is particularly desirable for $Ar^1$, $Ar^2$ to denote a phenyl group.

When at least one from among $Ar^1$ and $Ar^2$ comprises an onium cation, the onium cation may be contained in a substituent of $Ar^1$ and $Ar^2$. The onium cation may also be produced by further replacement of a hetero atom on an aromatic heterocyclic group denoted by $Ar^1$ and $Ar^2$. The onium cation is not specifically limited; preferably denotes an ammonium cation, oxonium cation, phosphonium ion, sulfonium cation, selenium ion, or iodonium cation, with an ammonium cation being preferred. In this context, the ammonium cation denotes a cationic group having a positive charge on a nitrogen atom, preferably a tetra-substituted nitrogen atom cation (the substituent being an alkyl group, aryl group, or aromatic heterocyclic group, described further below), pyridinium cation, imidazolium cation, thiazolium cation, oxazolium cation, iminium cation, or the like.

$Ar^1$ and $Ar^2$ may have further substituents. Examples of these substituents are alkyl groups (preferably having 1 to 30, more preferably 1 to 20, and particularly preferably, 1 to 10 carbon atoms, such as methyl groups, ethyl groups, iso-propyl groups, tert-butyl groups, n-octyl groups, n-decyl groups, n-hexadecyl groups, cyclopropyl groups, cyclopentyl groups, and cyclohexyl groups), alkenyl groups (preferably having 2 to 30, more preferably 2 to 20, and particularly preferably, 2 to 10 carbon atoms, such as vinyl groups, allyl groups, 2-butenyl groups, and 3-pentenyl groups), alkynyl groups (preferably having 2 to 30, more preferably 2 to 20, and particularly preferably, 2 to 10 carbon atoms, such as propargyl groups and 3-pentynyl groups), aryl groups (preferably having 6 to 30, more preferably 6 to 20, and particularly preferably, 6 to 12 carbon atoms, such as phenyl groups, p-methylphenyl groups, naphthyl groups, and anthranyl groups), amino groups (preferably having 0 to 30, more preferably 0 to 20, and particularly preferably, 0 to 10 carbon atoms, such as amino groups, methylamino groups, dimethylamino groups, diethylamino groups, dibenzylamino groups, diphenylamino groups, and ditolylamino groups), alkoxy groups (preferably having 1 to 30, more preferably 1 to 20, and particularly preferably, 1 to 10 carbon atoms, such as methoxy groups, ethoxy groups, butoxy groups, and 2-ethylhexyoxy groups), aryloxy groups (preferably having 6 to 30, more preferably 6 to 20, and particularly preferably, 6 to 12 carbon atoms, such as phenyloxy groups, 1-naphthyloxy groups, and 2-naphthyloxy groups), aromatic heterocyclic oxy groups (preferably having 1 to 30, more preferably 1 to 20, and particularly preferably, 1 to 12 carbon atoms, such as pyridyloxy groups, pyrazyloxy groups, pyrimidyloxy groups, and quinolyloxy groups), acyl groups (preferably having 1 to 30, more preferably 1 to 20, and particularly preferably, 1 to 12 carbon atoms, such as acetyl groups, benzoyl groups, formyl groups, and pivaloyl groups), alkoxycarbonyl groups (preferably having 2 to 30, more preferably 2 to 20, and particularly preferably, 2 to 12 carbon atoms, such as methoxycarbonyl groups and ethoxycarbonyl groups), aryloxycarbonyl groups (preferably having 7 to 30, more preferably 7 to 20, and particularly preferably, 7 to 12 carbon atoms, such as phenyloxycarbonyl groups), acyloxy groups (preferably having 2 to 30, more preferably 2 to 20, and particularly preferably, 2 to 10 carbon atoms, such as acetoxy groups and benzoyloxy groups), acylamino groups (preferably having 2 to 30, more preferably 2 to 20, and particularly preferably, 2 to 10 carbon atoms, such as acetylamino groups and benzoylamino groups), alkoxycarbonylamino groups (preferably having 2 to 30, more preferably 2 to 20, and particularly preferably, 2 to 12 carbon atoms, such as methoxycarbonylamino groups), aryloxycarbonylamino groups (preferably having 7 to 30, more preferably 7 to 20, and particularly preferably, 7 to 12 carbon atoms, such as phenyloxycarbonylamino groups), sulfonylamino groups (preferably having 1 to 30, more preferably 1 to 20, and particularly preferably, 1 to 12 carbon atoms, such as methanesulfonylamino groups and benzenesulfonyl amino groups), sulfamoyl groups (preferably having 0 to 30, more preferably 0 to 20, and particularly preferably, 0 to 12 carbon atoms, such as sulfamoyl groups, methylsulfamoyl groups, dimethylsulfamoyl groups, and phenylsulfamoyl groups), carbamoyl groups (preferably having 1 to 30, more preferably 1 to 20, and particularly preferably, 1 to 12 carbon atoms, such as carbamoyl groups, methylcarbamoyl groups, diethylcarbamoyl groups, and phenylcarbamoyl groups), alkylthio groups (preferably having 1 to 30, more preferably 1 to 20, and particularly preferably, 1 to 12 carbon atoms, such as methylthio groups and ethylthio groups), arylthio groups (preferably having 6 to 30, more preferably 6 to 20, and particularly preferably, 6 to 12 carbon atoms, such as phenylthio groups), aromatic heterocyclic thio groups (preferably having 1 to 30, more preferably 1 to 20, and particularly preferably, 1 to 12 carbon atoms, such as pyridylthio groups, 2-benzimizolylthio groups, 2-benzoxazolylthio groups, and 2-benzthiazolylthio groups), sulfonyl groups (preferably having 1 to 30, more preferably 1 to 20, and particularly preferably, 1 to 12 carbon atoms, such as mesyl groups and tosyl groups), sulfinyl groups (preferably having 1 to 30, more preferably 1 to 20, and particularly preferably, 1 to 12 carbon atoms, such as methanesulfinyl groups and benzenesulfinyl groups), ureido groups (preferably having 1 to 30, more preferably 1 to 20, and particularly preferably, 1 to 12 carbon atoms, such as ureido groups, methylureido groups, and phenylureido groups), phosphoramide groups (preferably having 1 to 30, more preferably 1 to 20, and particularly preferably, 1 to 12 carbon atoms, such as diethylphosphoramide group and phenylphosphoramide group), hydroxy groups, mercapto groups, halogen atoms (such as fluorine, chlorine, bromine, and iodine atoms), cyano groups, sulfo groups, carboxyl groups, nitro groups, hydroxamic acid groups, sulfino groups, hydrazino groups, imino groups, aromatic heterocyclic groups (preferably having 1 to 30, more preferably 1 to 12 carbon atoms, with examples of the hetero atom being nitrogen, oxygen, and sulfur atoms, more specific examples being: imidazolyl groups, pyridyl groups, quinolyl groups, furyl groups, thienyl groups, piperidyl groups, morpholino groups, benzoxazolyl groups, benzimidazolyl groups, benzthioazolyl groups, carbazolyl groups, and azepinyl groups), and silyl groups (preferably having 3 to 40, more preferably 3 to 30, and particularly preferably, 3 to 24 carbon atoms, such as trimethylsilyl groups and triphenylsilyl groups). These substituents may be further substituted.

$R^3$ and $R^4$ each independently denote a substituent. Examples of the substituents denoted by $R^3$ and $R^4$ are preferably the examples of substituents given for $Ar^1$ and $Ar^2$ above, more preferably alkyl groups, aryl groups, heterocyclic groups, amino groups, alkoxy groups, acyl groups, acyloxy groups, acylamino groups, and particularly preferably, alkyl groups, aryl groups, alkoxy groups, and acyl groups. The substituents denoted by $R^3$ and $R^4$ may be bonded together. That is, the left and right pyridine rings may be bonded with a linkage group in which $R^3$ and $R^4$ bond together. Further, $R^3$ and $R^4$ may form a ring with a benzene ring on which $R^3$ and $R^4$ respectively substitute.

m3 and m4 each independently denote an integer ranging from 0 to 4. Each of m3 and m4 preferably denotes 0 to 2, more preferably 0 to 1. When m3 and m4 denote integers falling within a range of 2 to 4, plural $R^3$s and $R^4$s may be identical or different from each other $L^1$ denotes a single bond or a divalent linkage group. The divalent linkage group desirably has a pyridinium group on both ends. The divalent linkage group denoted by $L^1$ is as described further below for the linkage group in general formula (III).

The number of cationic moieties in general formula (I) is preferably equal to or greater than 3 and equal to or less than 1,000, more preferably equal to or greater than 3 and equal to or less than 10, and particularly preferably equal to or greater than 4 and equal to or less than 6.

A preferred embodiment of the cationic compound of the present invention can be a cationic compound in which, in general formula (I), $Ar^1$ is denoted by:

[Chem. 9]

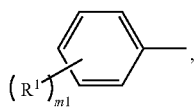

and Ar² is denoted by:

[Chem. 10]

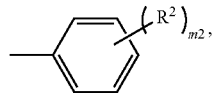

that is, a cationic compound denoted by the following general formula (II).

[Chem. 11]

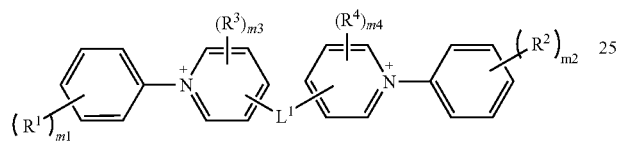
(II)

A further preferred embodiment can be a cationic compound in which, in general formula (II), $L^1$ is a single bond, and at least one from among $R^1$ and $R^2$ denotes a substituent comprising a nitrogen cation.

Another preferred embodiment of the cationic compound of the present invention can be a compound in which, in general formula (II), L1 is:

[Chem. 12]

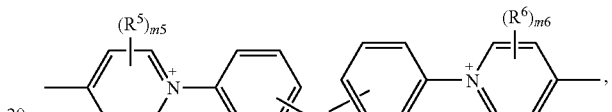

wherein $R^1$ and $R^2$ each independently denote a substituent that may be form a ring with a benzene ring substituted, that is, a cationic compound denoted by the following general formula (III).

[Chem. 13]

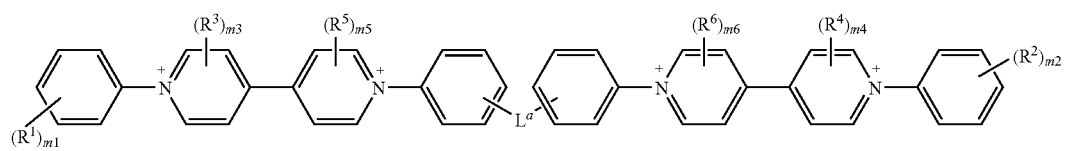
(III)

Another more preferred embodiment of the cationic compound of the present invention can be a cationic compound dented by the following general formula (IV).

[Chem. 14]

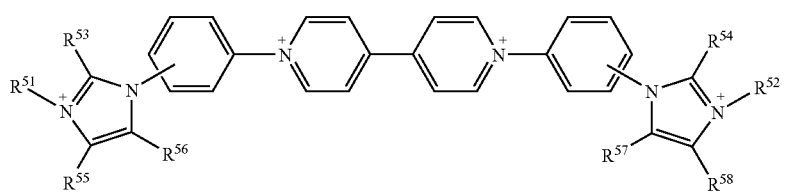
(IV)

General formulas (II), (III), and (IV) will be sequentially described in detail below.

General Formula (II)

In general formula (II), $R^1$ and $R^2$ each independently denote a substituent. Examples of these substituents are, in addition to those described for substituents of $R^3$ and $R^4$ above, substituents having nitrogen cations. In this context, the term "nitrogen cation" means a cation comprising one or more nitrogen atoms, with at least one of the nitrogen atoms having a positive charge.-

Desirable examples of the nitrogen cation are tetra-substituted nitrogen atom cations (with the substituents denoting the alkyl groups, aryl groups, and aromatic heterocyclic groups described as examples of substituents of $Ar^1$ and $Ar^2$) and nitrogen atom-containing aromatic heterocyclic cations.

A preferred embodiment of the tetra-substituted nitrogen atom cation can be:

[Chem. 15]

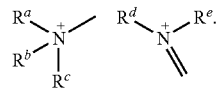

In the above, $R^a$, $R^b$, $R^c$, $R^d$, and $R^e$ each independently denote one of the alkyl groups, aryl groups, or aromatic heterocyclic groups described by way of example for the substituents of $Ar^1$ and $Ar^2$ above.

Examples of nitrogen atom-containing aromatic heterocyclic cations are pyridinium cations, imidazolium cations, thiazolium cations, oxazolium cations, and iminium cations. Specific examples are:

[Chem. 16]

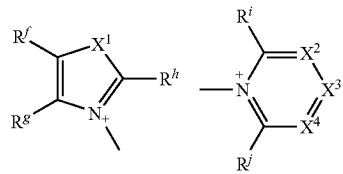

In the above, $X^1$ denotes O, N, S, or CR (where R denotes a hydrogen atom or a substituent), with N being preferred. $R^f$, $R^g$, and $R^h$ each independently denote a hydrogen atom or a substituent. $R^g$ and $R^h$ may each form a ring with a nitrogen atom contained in a hetero ring. When $X^1$ denotes CR, $X^1$ and $R^f$ or $R^h$ may link to form a ring. $X^2$, $X^3$, and $X^4$ each independently denote N or CR' (where R' denotes a hydrogen atom or a substituent), and $R^i$ and $R^j$ each independently denote a hydrogen atom or a substitutent. $R^i$ and $R^j$ may each form a ring with a nitrogen atom contained in a hetero ring. When $X^2$ denotes CR', $X^2$ and $R^i$ may link to form a ring. When $X^4$ denotes CR', $X^4$ and $R^j$ may link to form a ring. The above substituents are the alkyl groups, aryl groups, and aromatic heterocyclic groups described by way of example for the substituents of $Ar^1$ and $Ar^2$ above.

Examples of the above nitrogen atom-containing aromatic heterocyclic cation are the nitrogen atom-containing aromatic heterocycles given below in which at least one nitrogen is substituted.

[Chem. 17]

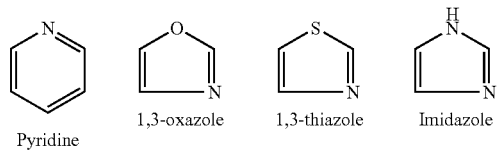

Pyridine    1,3-oxazole    1,3-thiazole    Imidazole

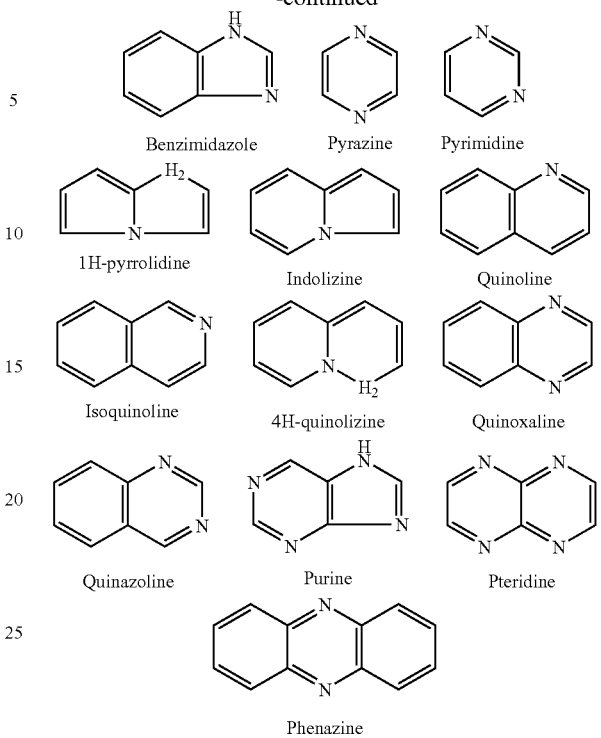

Among the above examples, those in which, in pyridine, 1,3-oxazole, 1,3-thiazole, imidazole or benzimidazole, at least one nitrogen is substituted are preferred.

When $L^1$ is a single bond, at least one from among $R^1$ and $R^2$ desirably denotes the above-described substituent having a nitrogen cation, it being preferable for both to denote a substituent having a nitrogen cation. $R^1$ and $R^2$ may each form a ring with a benzene ring on which they respectively substitute.

One of m1 and m2 denotes an integer ranging from 0 to 5, preferably from 0 to 2 and the other denotes an integer ranging from 1 to 5, preferably from 1 to 2. When m1 and m2 are an integer ranging from 2 to 5, plural $R^1$s and $R^2$s may be identical or different from each other.

In general formula (II), $R^3$, $R^4$, $L^1$, m3, and m4 are each defined as in general formula (I); the details are as set forth above. The number of cationic moieties in general formula (II), as in general formula (I), is preferably equal to or greater than 3 and equal to or less than 1,000, more preferably equal to or greater than 3 and equal to or less than 10, particularly preferably equal to or greater than 4 and equal to or less than 6.

General Formula (III)

In general formula (III), $R^1$, $R^2$, $R^3$, and $R^4$ are defined as in general formulas (I) and (II). $R^5$ and $R^6$ each independently denote a substituent. The details of the substituents denoted by $R^5$ and $R^6$, such as desirable examples thereof, are as set forth above for the substituents of $R^3$ and $R^4$. Particularly preferred examples of the substituents denoted by $R^1$, $R^2$, $R^3$, $R^4$, $R^5$, and $R^6$ in general formula (III) are: alkyl groups, aryl groups, alkoxy groups, aryloxy groups, acyl groups, alkoxycarbonyl groups, amide groups, sulfamoyl groups, and ureido groups.

In general formula (III), m5 and m6 each independently denote an integer ranging from 0 to 4, preferably 0 to 2, and more preferably, 0. When m5 and m6 denote integers falling within a range of 2 to 4, plural $R^5$s and $R^6$s may be identical or different from each other.

In general formula (III), m1, m2, m3, and m4 are defined as in general formulas (I) and (II). In general formula (III), $m^1$ and $m^2$ more preferably denote integers falling within a range of 0 to 2; $m^3$ and $m^4$ preferably denote integers falling within a range of 0 to 4, more preferably 0 to 2, and particularly preferably, 0.

In general formula (III), $L^a$ denotes a divalent linkage group; preferably a single bond, oxygen atom, sulfur atom, nitrogen atom, methylene group, phenylene group, carbonyl group, sulfanyl group, amide group, and combination groups of the above; and more preferably, the following linkage group.

[Chem. 18]

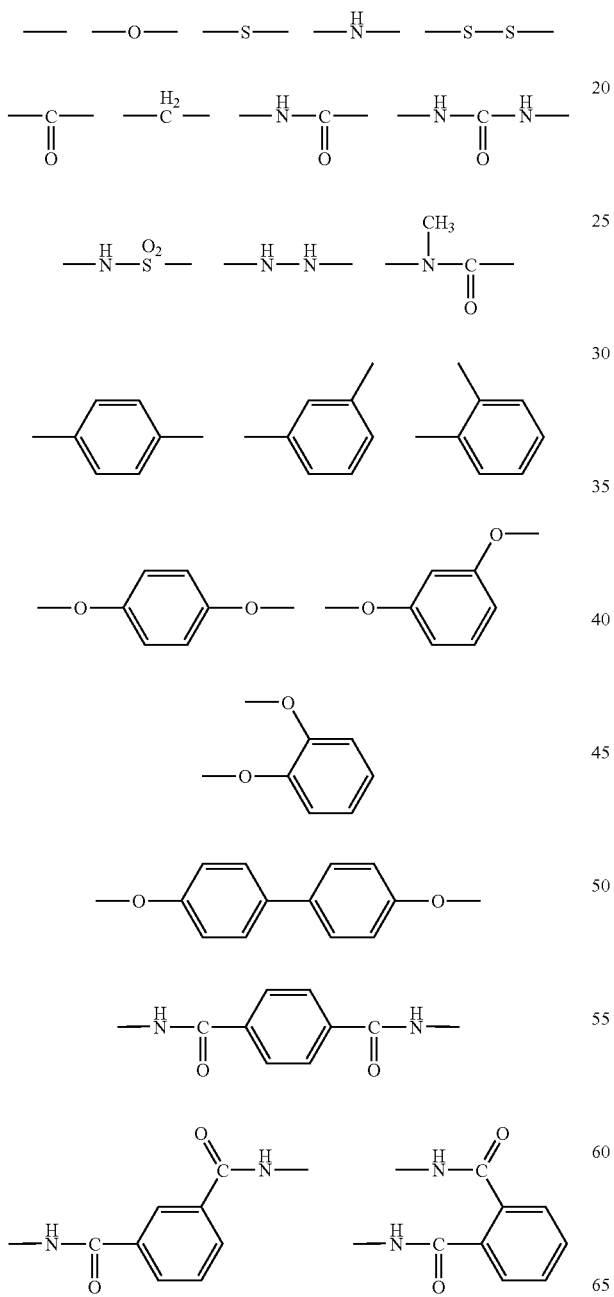

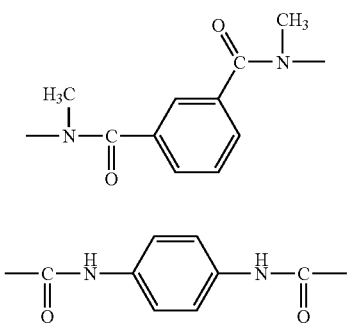

The number of cationic moieties in general formula (III) is the same as for general formulas (I) and (II), preferably equal to or greater than 3 and equal to or less than 1,000, more preferably equal to or greater than 3 and equal to or less than 10, and particularly preferably equal to or greater than 4 and equal to or less than 6.

General Formula (IV)

In general formula (IV), $R^{51}$ and $R^{52}$ each independently denote a hydrogen atom or alkyl group. $R^{53}$, $R^{54}$, $R^{55}$, $R^{56}$, $R^{57}$ and $R^{58}$ each independently denote a hydrogen atom, alkyl group, aryl group, or aromatic heterocyclic group, it being permissible for $R^{55}$ and $R^{56}$, and $R^{57}$ and $R^{58}$, to be linked, forming a five or six-membered ring. The ring that is formed may be an aliphatic ring, benzene ring, aromatic hetero ring, or the like. The examples of the substituents set forth above are also examples of the alkyl groups, aryl groups, and aromatic heterocyclic groups that are denoted by $R^{51}$, $R^{52}$, $R^{53}$, $R^{54}$, $R^{55}$, $R^{56}$, $R^{57}$, and $R^{58}$; further substitution is also possible.

$R^{51}$ and $R^{52}$ preferably denote substituted or unsubstituted alkyl groups (such as methyl and benzyl groups), it being more preferable for both to denote identical alkyl groups. It is preferable for $R^{53}$, $R^{54}$, $R^{55}$, $R^{56}$, $R^{57}$, and $R^{58}$ to all denote hydrogen atoms, or for $R^{53}$ and $R^{54}$ to denote hydrogen atoms and for $R^{55}$ and $R^{56}$ to be linked and $R^{57}$ and $R^{58}$ to be linked to form benzene rings.

Preferred examples of the cationic compound of the present invention will be given below. However, the present invention is not limited to the following examples.

[Chem. 19]
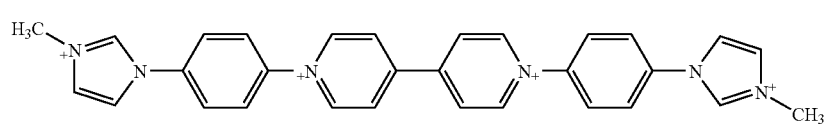 (V-1)
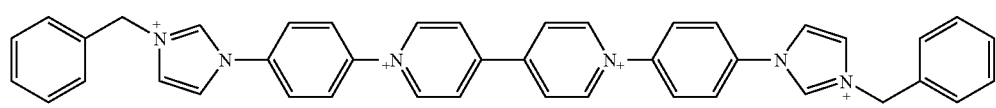 (V-2)
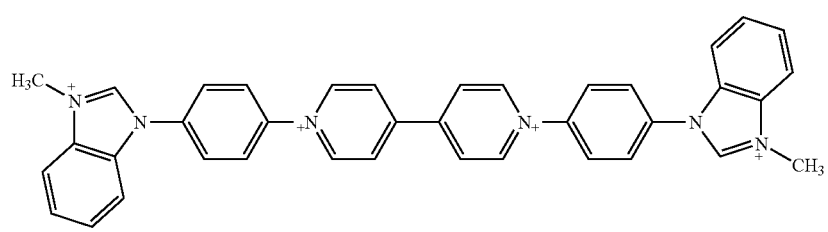 (V-3)
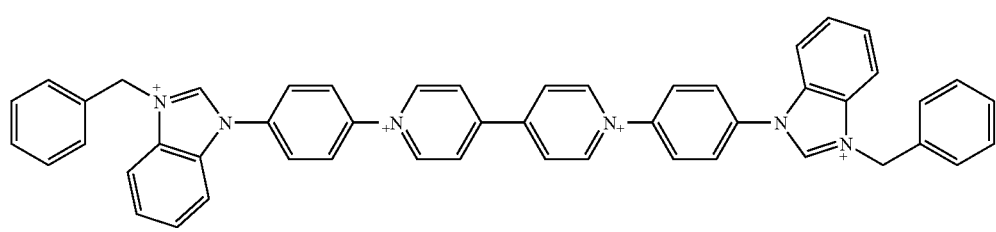 (V-4)
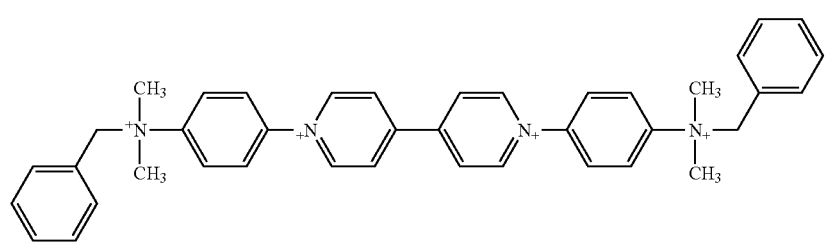 (V-5)
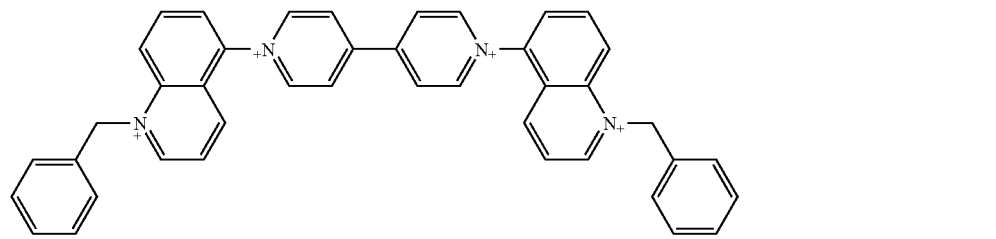 (V-6)
[Chem. 20]
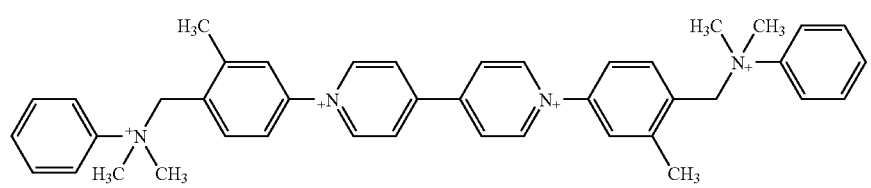 (V-7)
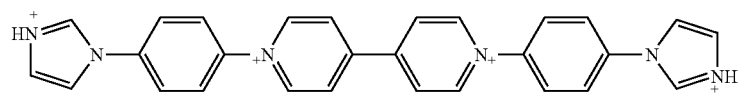 (V-8)

-continued
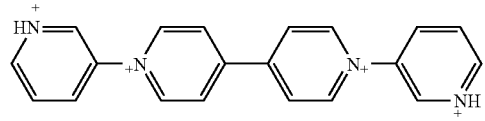
(V-9)
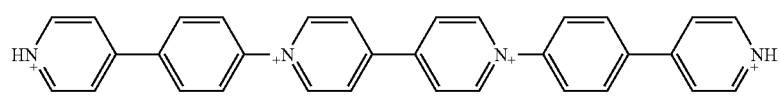
(V-10)
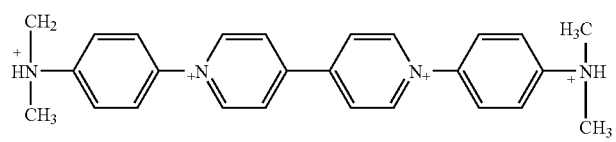
(V-11)
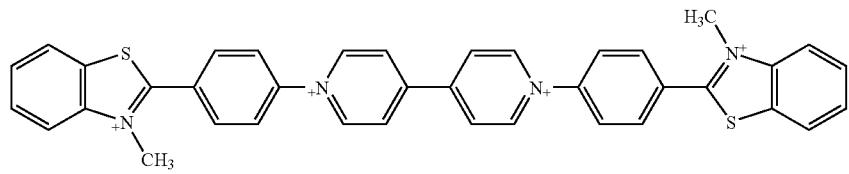
(V-12)
[Chem. 21]
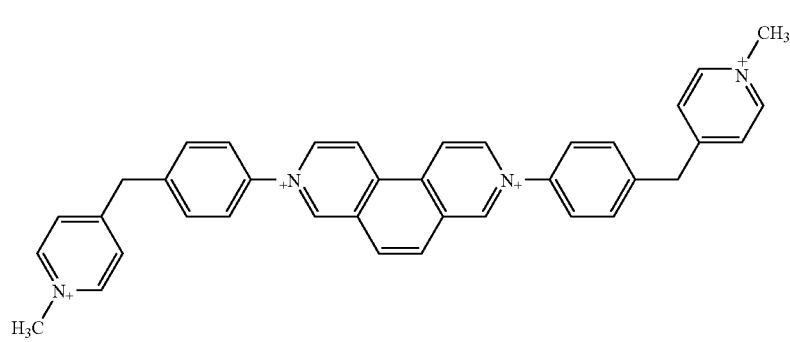
(V-13)
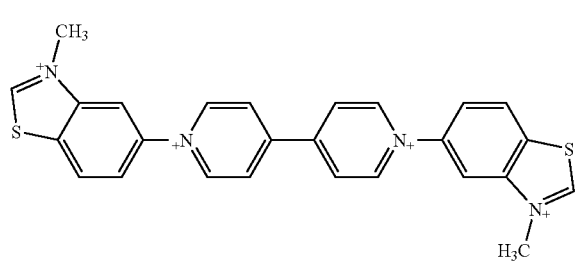
(V-14)
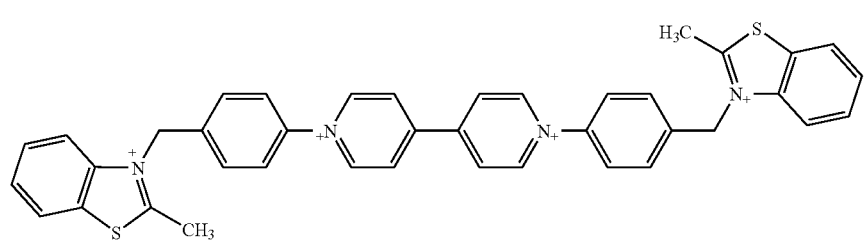
(V-15)

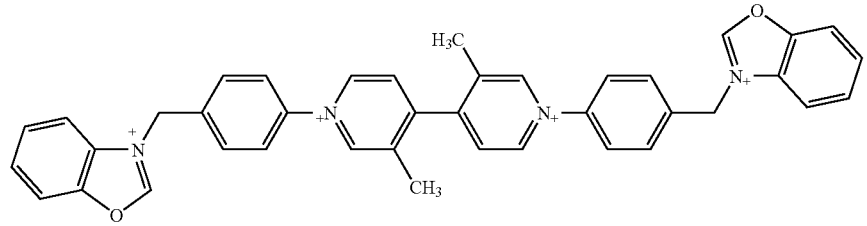
(V-16)
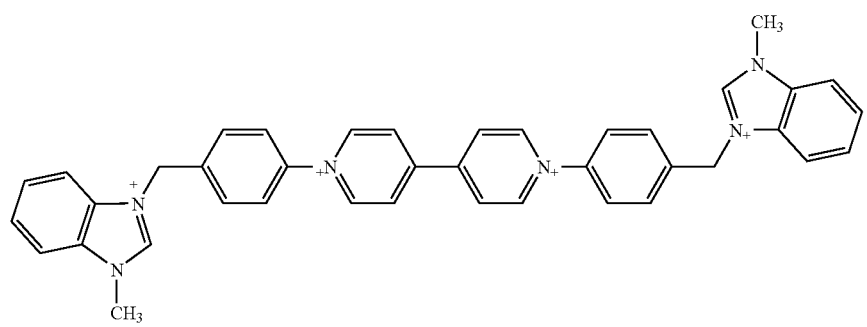
(V-17)
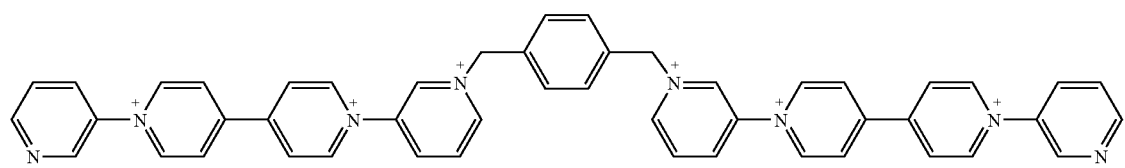
(V-18)
[Chem. 22]
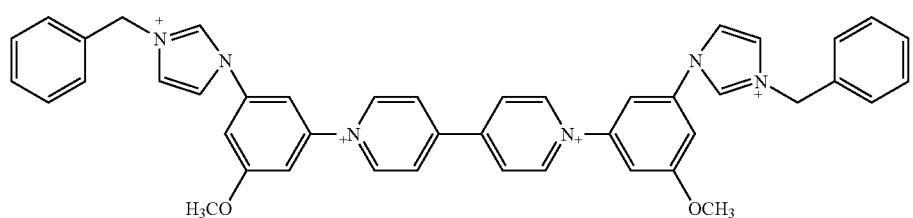
(V-19)
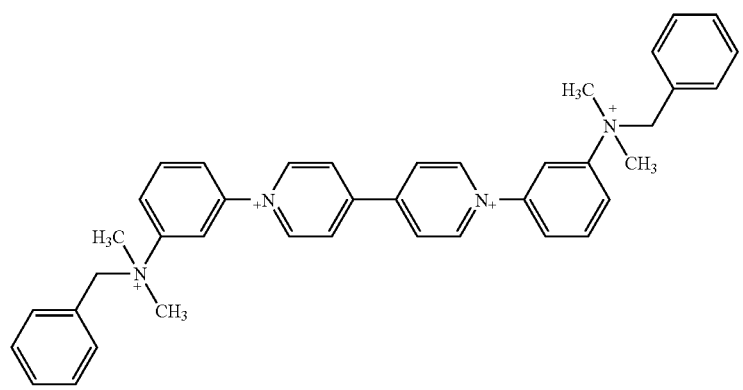
(V-20)

-continued
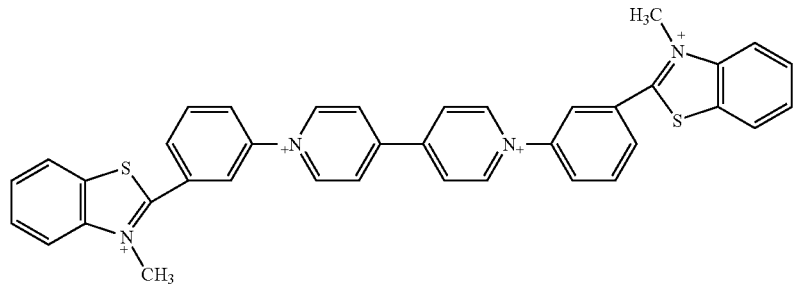
(V-21)
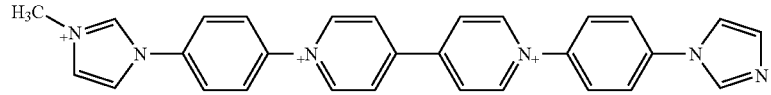
(V-22)
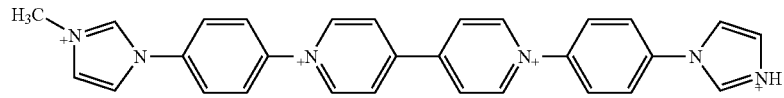
(V-23)
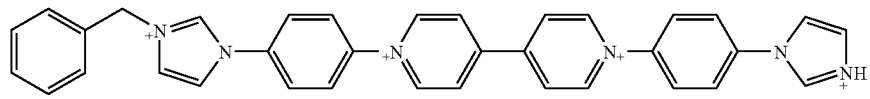
(V-24)
[Chem. 23]
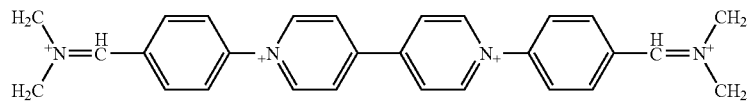
(V-25)
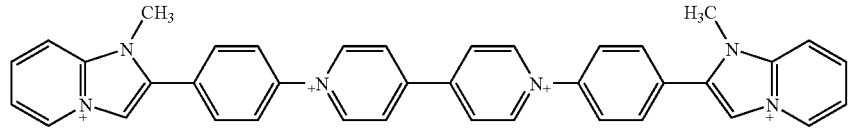
(V-26)
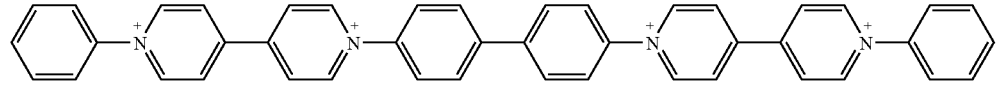
(V-27)
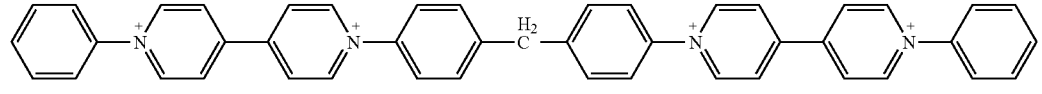
(V-28)
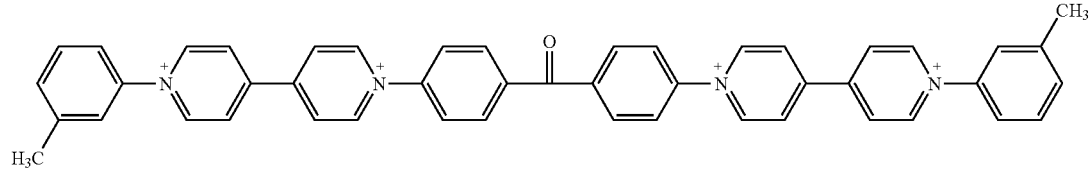
(V-29)
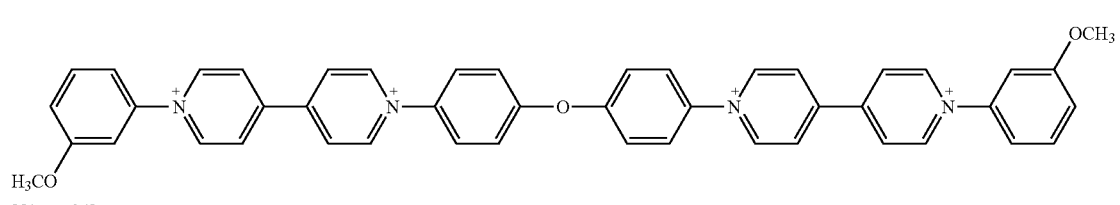
(V-30)
[Chem. 24]
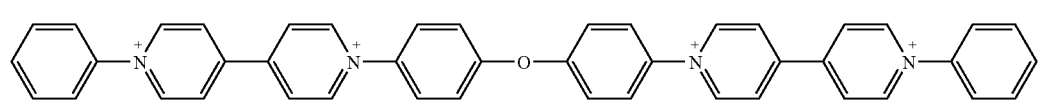
(V-31)

(V-32)
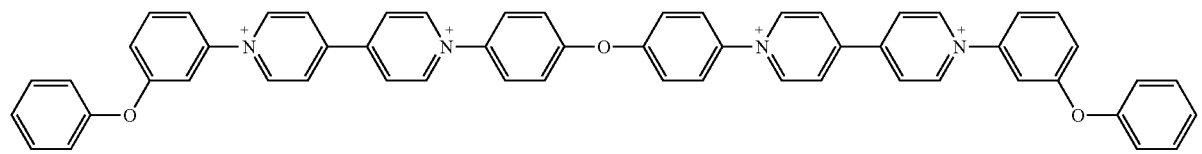
(V-33)
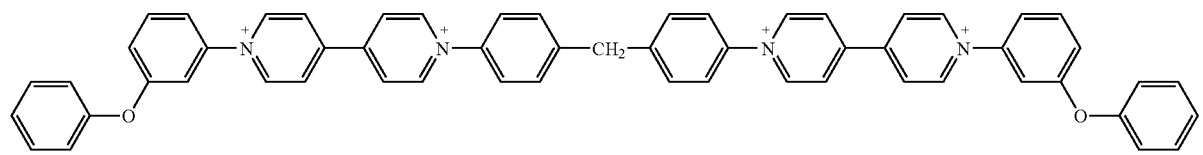
(V-34)
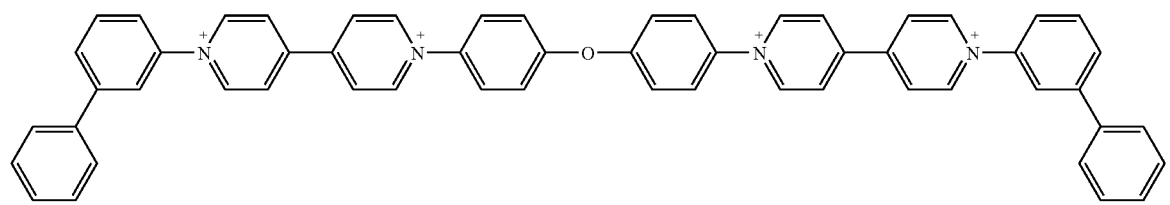
(V-35)
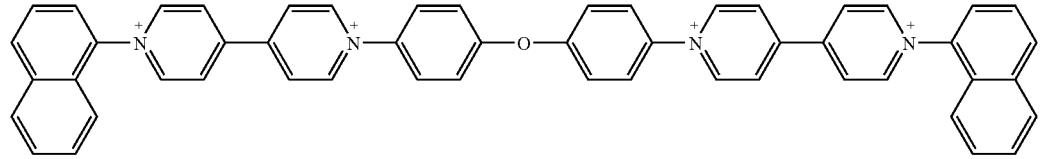
(V-36)
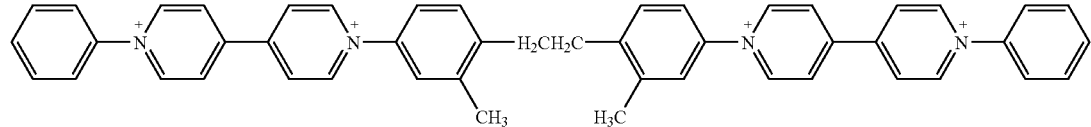
(V-37)
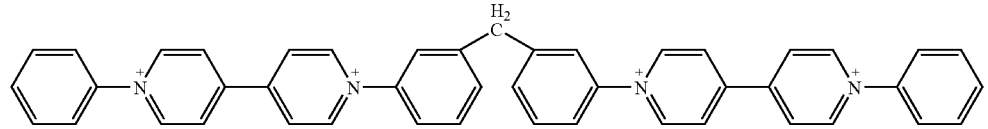
[Chem. 25]
(V-38)
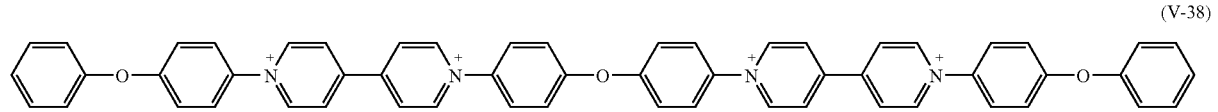
(V-39)
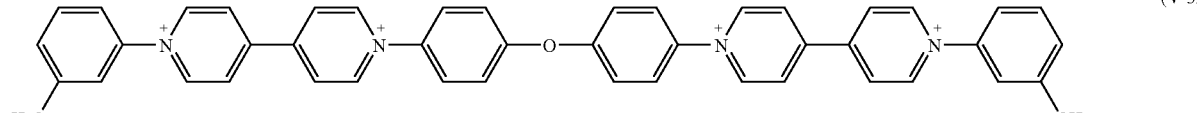
(V-40)
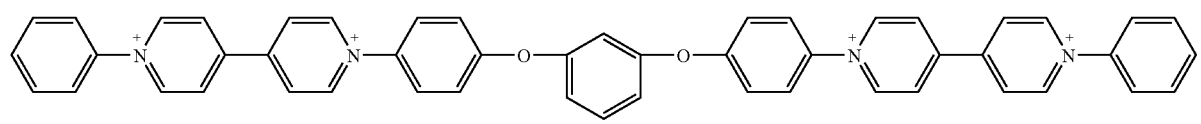

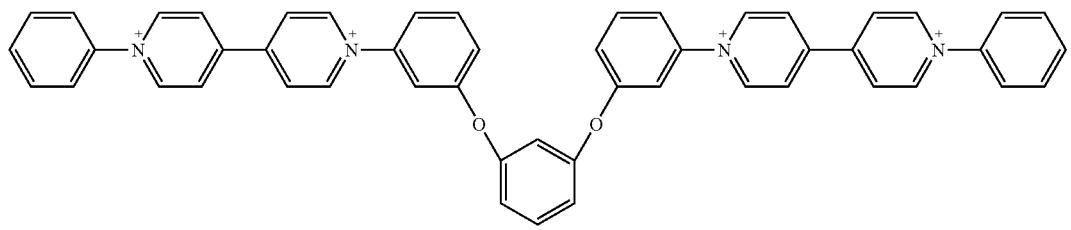
(V-41)
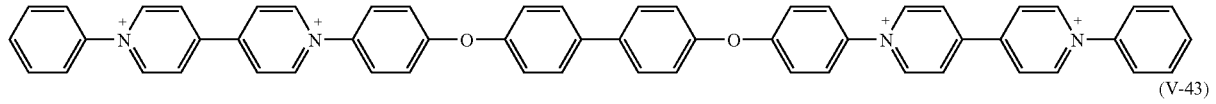
(V-42)
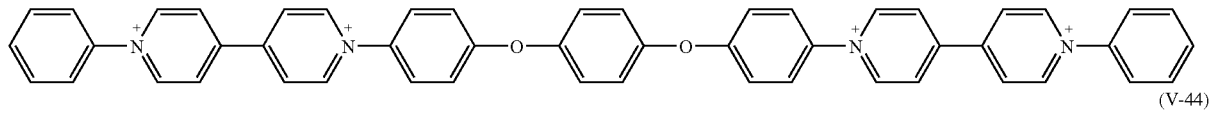
(V-43)
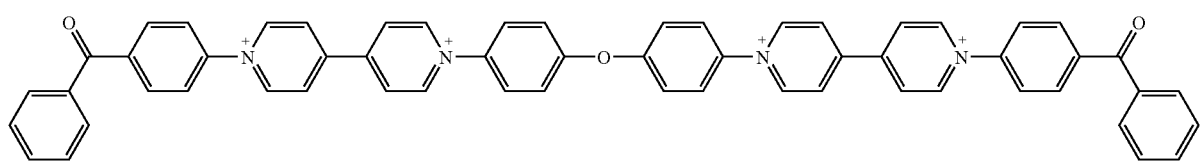
(V-44)
[Chem. 26]
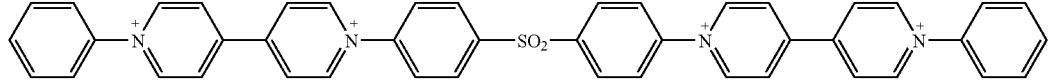
(V-45)
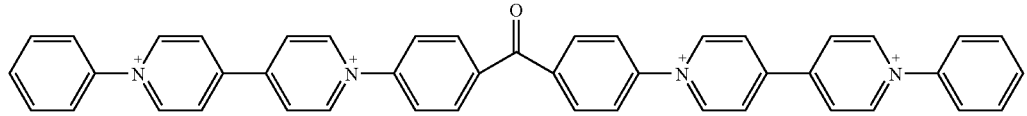
(V-46)
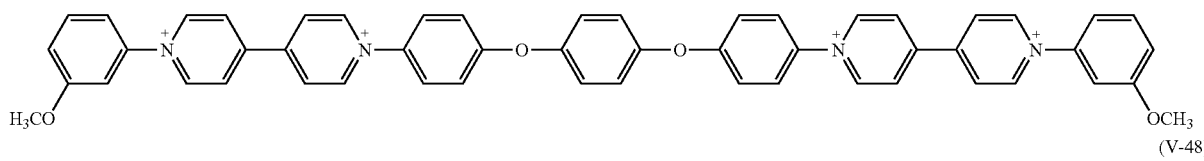
(V-47)
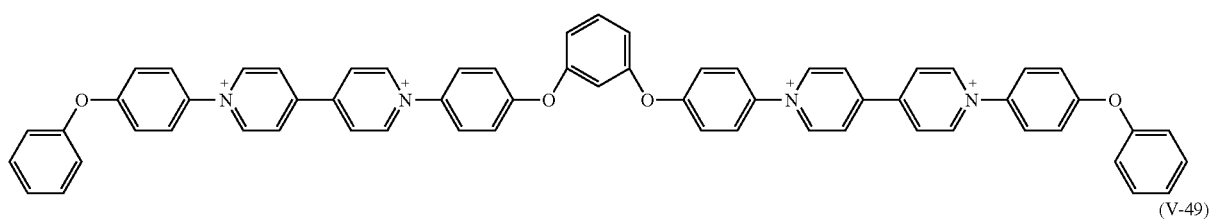
(V-48)
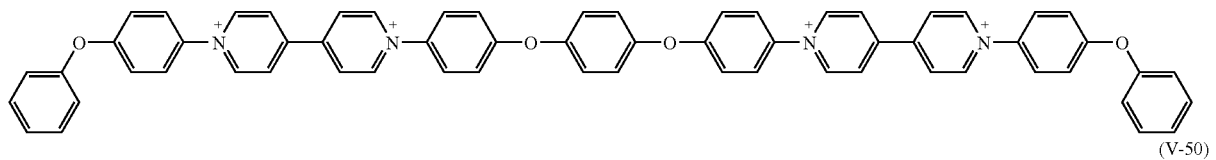
(V-49)
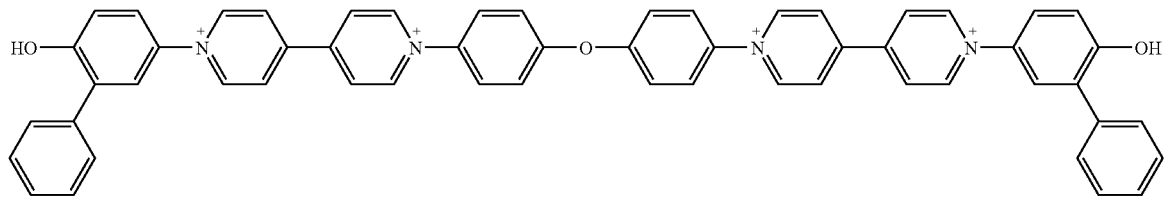
(V-50)

-continued
(V-51)
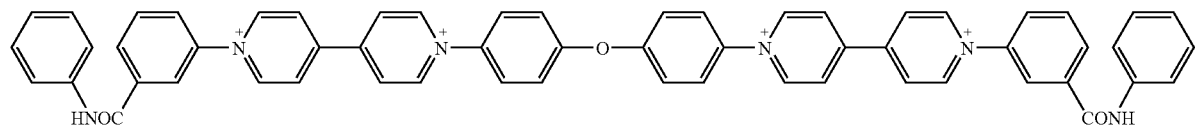
[Chem. 27]
(V-52)
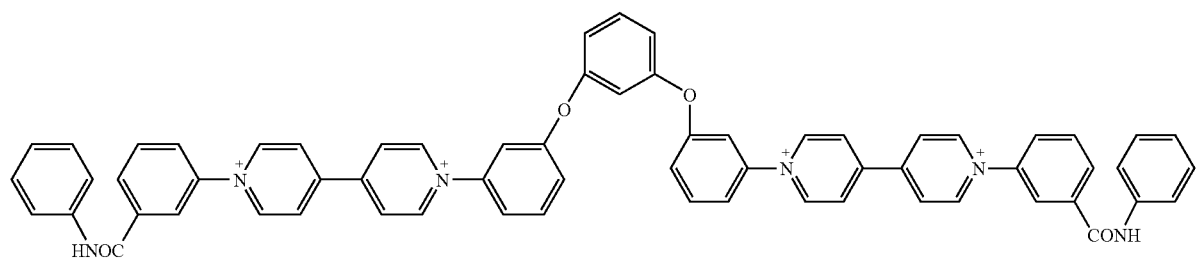
(V-53)
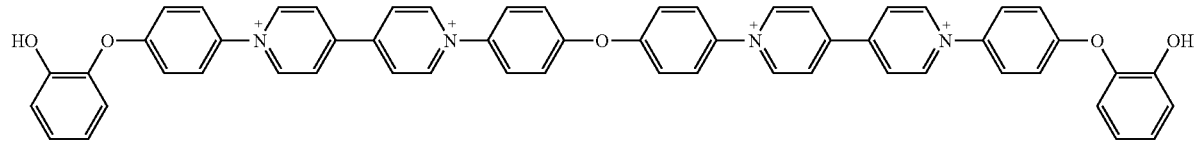
(V-54)
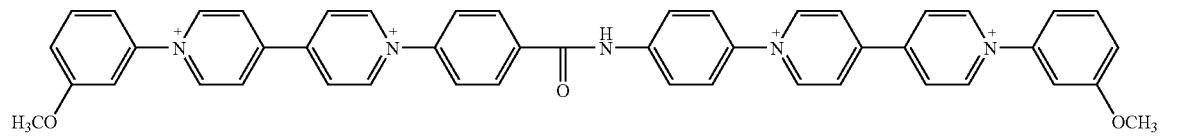
(V-55)
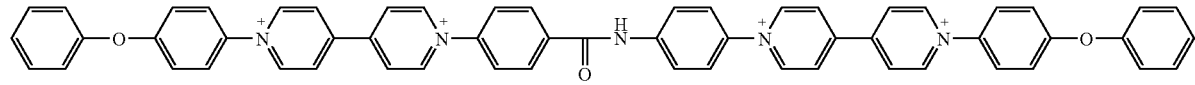
(V-56)
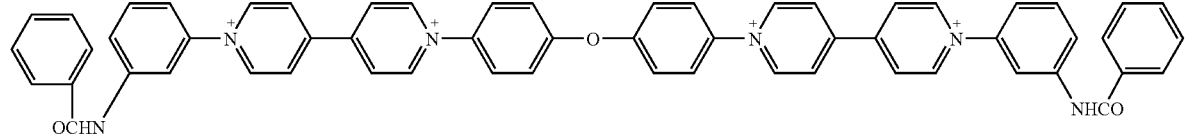
(V-57)
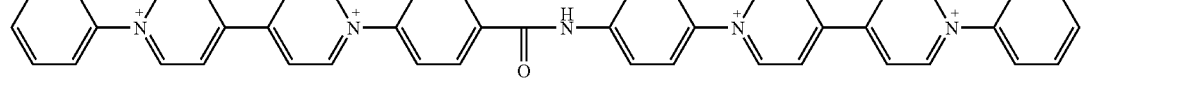
(V-58)
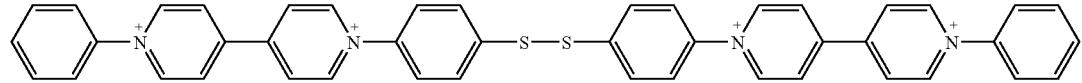
[Chem. 28]
(V-59)
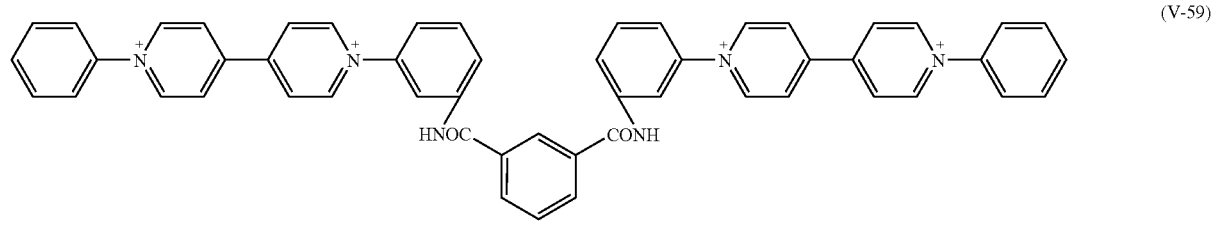

-continued
(V-60)
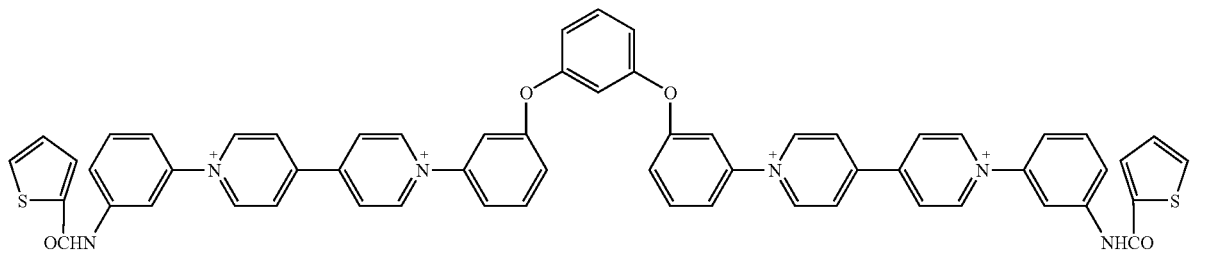
(V-61)
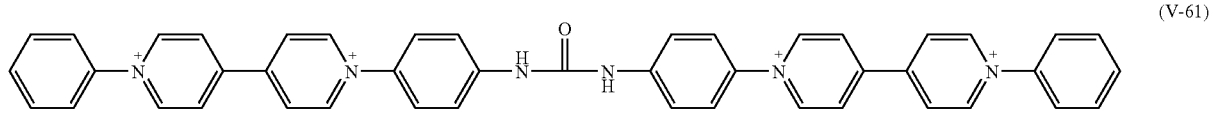
(V-62)
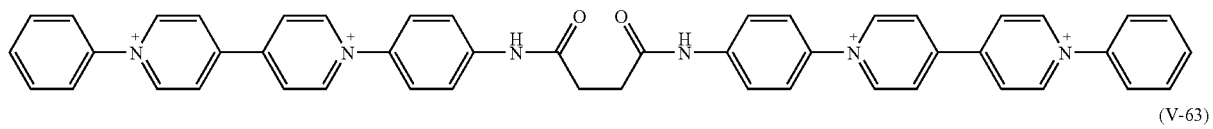
(V-63)
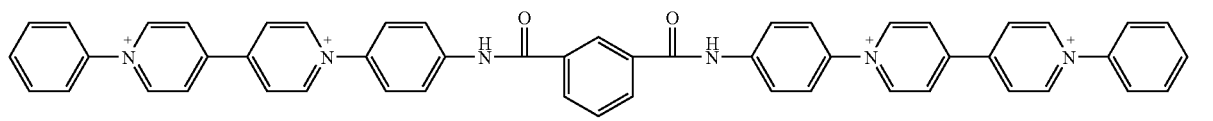
(V-64)
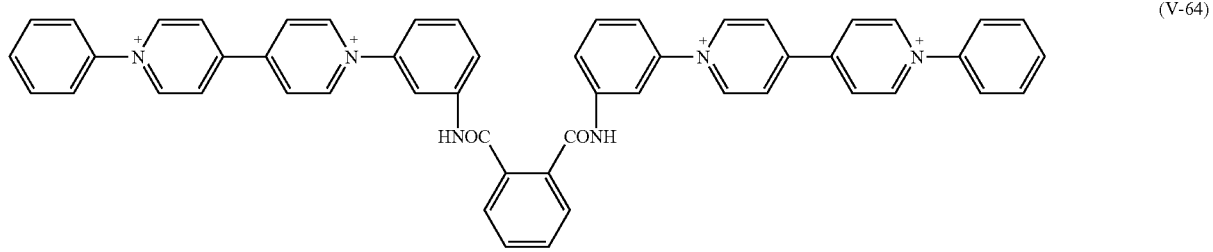
(V-65)
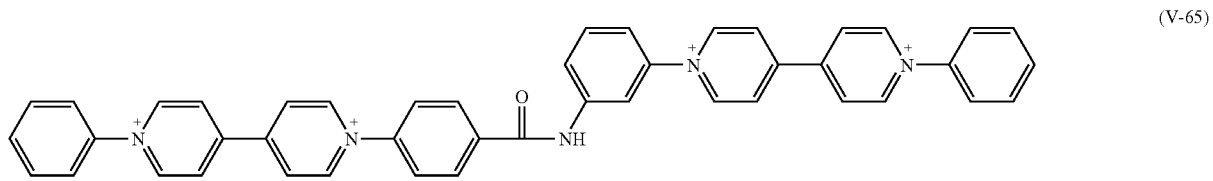
[Chem. 29]
(V-66)
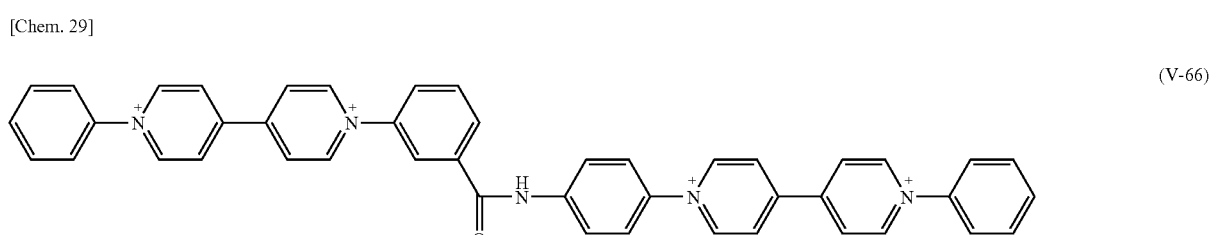
(V-67)
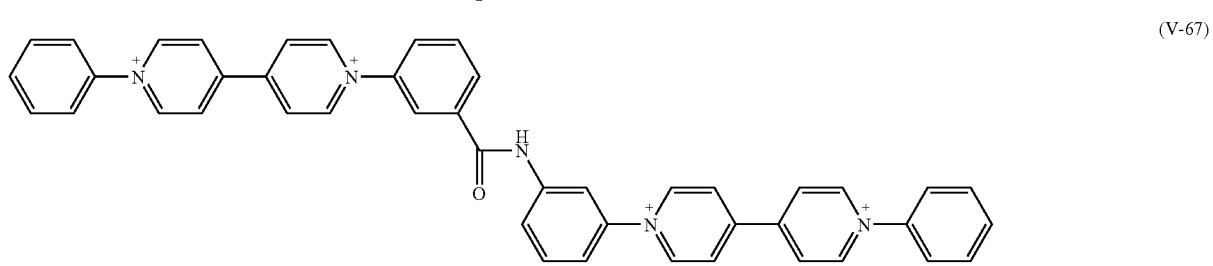

-continued (V-68)
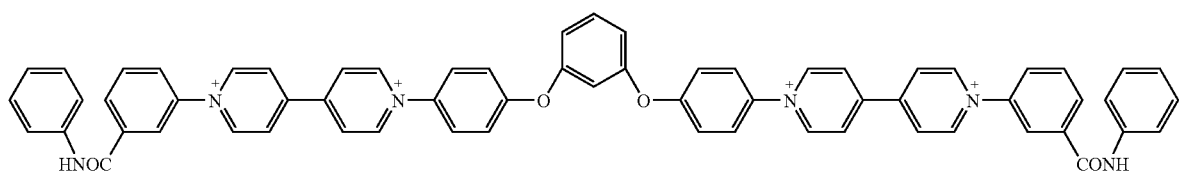

(V-69)
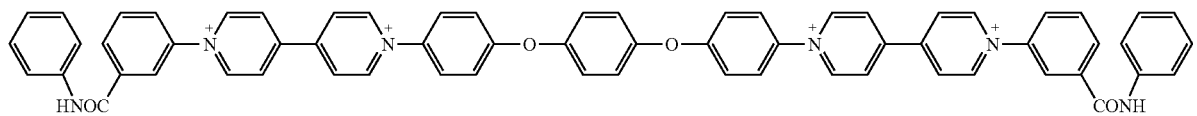

(V-70)
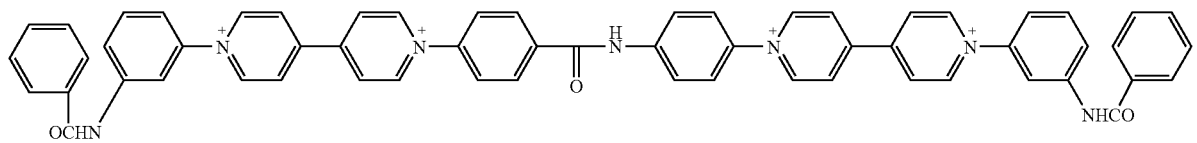

(V-71)
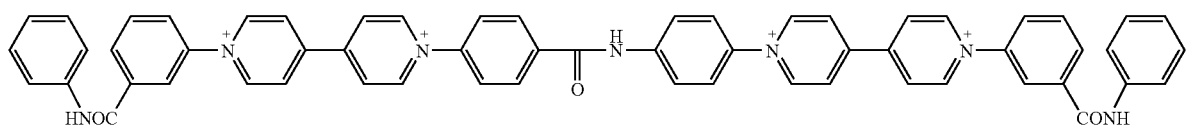

(V-72)
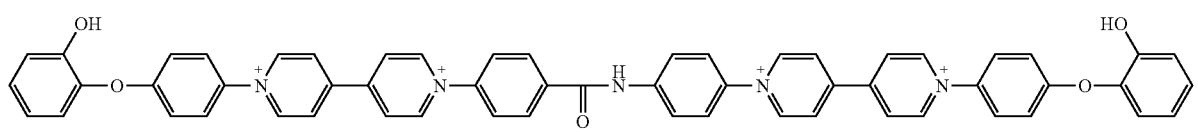

As described in Japanese Unexamined Patent Publication (KOKAI) No. 2003-128654, the cationic compound of the present invention can be synthesized by substituting a pyridinium compound on which a dinitrobenzene or heteroaryl substitutes onto the nitrogen thereof with an aniline or heteroarylamine. Further, the cationic compound of the present invention, having three or more cationic groups, can be synthesized by employing, as the above aniline or heteroarylamine, that already comprising a cationic group. It can also be synthesized by oniumizing a substituent of an aryl group or heteroaryl group on a nitrogen of a bipiridinium compound.

The compound obtained can be purified by known methods. Confirmation that the cationic compound of the present invention has been obtained can be done by a known analysis method, such as NMR.

[Dye Compound]

The dye compound of the present invention comprises the cationic compound of the present invention and an anion in an amount capable of neutralizing a charge of the above cationic compound. The dye compound is preferably a compound in the form of a salt formed by the cationic compound and the anion. The dye compound of the present invention preferably has a maximum absorption wavelength in the dye film of equal to or higher than 500 nm and less than 720 nm, more preferably equal to or higher than 550 nm and less than 600 nm, and optimally, equal to or higher than 565 nm and less than 590 nm.

The anion may be either an inorganic anion or organic anion, so long as it is capable of neutralizing the charge of the cationic compound of the present invention and forming a salt. Examples are halide ions (Cl$^-$, Br$^-$, I$^-$, and the like); sulfonate ions (such as $CH_3SO_3^-$, $CF_3SO_3^-$, $CF_3(CF_2)_7SO_3^-$, p-toluenesulfonate ions, and napthalene-1,5-disulfonate ions); sulfuric acid ions ($CH_3SO_4^-$ and the like); $ClO_4^-$; $BF_4^-$; $SbF_6^-$; phosphoric acid ions ($PF_6^-$,

[Chem. 30]

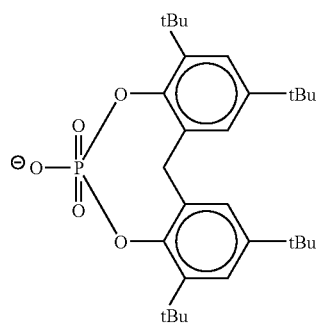

and the like); metal complex ions (such as,

[Chem. 31]

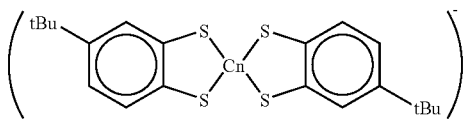

[Chem. 32]

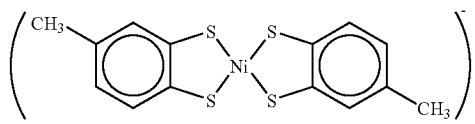

[Chem. 33]

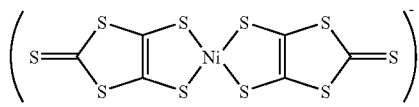

and the like); and anionic dyes (such as oxonol dyes and anionic dye moieties from which anionic dissociative groups (OH groups, NH groups, COOH groups, $SO_3H$ groups, and the like) are dissociated. The anions are preferably anionic dyes, more preferably oxonol dyes. Oxonol dyes are compounds denoted by general formula (A) below, the structure of which is not specifically limited other than that the maximum absorption wavelength be equal to or higher than 350 nm and less than 720 nm. A dye having 5 to 7 methines and a chainlike acidic nucleus or cyclic acidic nucleus is desirable.

[Chem. 34]

General formula (A)

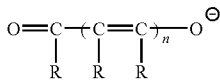

R: hydrogen or substituent,
n: integer of equal to or greater than 0

In general formula (A), n preferably denotes an integer ranging from 1 to 4. Examples of the substituent denoted by R can be those described by way of example for the substituents of $Ar^1$ and $Ar^2$. Preferred examples are alkyl groups having 1 to 20 carbon atoms (such as methyl groups, ethyl groups, and isopropyl groups), halogen atoms (such as chlorine, bromine, iodine, and fluorine), alkoxy groups having 1 to 20 carbon atoms (such as methoxy groups, ethoxy groups, and isopropyloxy groups), aryl groups having 6 to 26 carbon atoms (such as phenyl groups and 2-naphthyl groups), heterocyclic groups having 0 to 20 carbon atoms (such as 2-pyridyl groups and 3-pyridyl groups), aryloxy groups having 6 to 20 carbon atoms (such as phenoxy groups, 1-naphthoxy groups, and 2-naphthoxy groups), acylamino groups having 1 to 20 carbon atoms (such as acetylamino groups and benzoylamino groups), carbamoyl groups having 1 to 20 carbon atoms (such as N,N-dimethylcarbamoyl groups), sulfo groups, hydroxy groups, carboxy groups, alkylthio groups having 1 to 20 carbon atoms (such as methylthio groups), and cyano groups. Plural Rs may link to form a ring. The anion is more preferably an oxonol dye having the cyclic acidic nucleus denoted by the following general formula (V);

[Chem. 35]

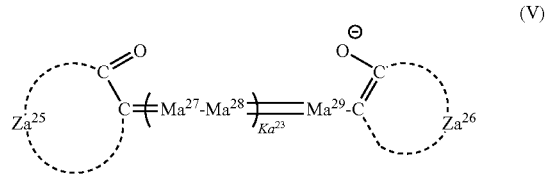

and particularly preferably, an oxonol dye denoted by the following general formula (VI).

[Chem. 36]

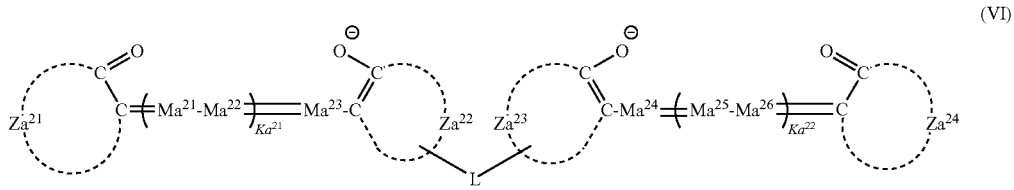

General formulas (V) and (VI) will be sequentially described below in detail.

General Formula (V)

In general formula (V), $Za^{25}$ and $Za^{26}$ each independently denote an atom group forming an acidic nucleus. Examples are described in James, ed., The Theory of the Photographic Process, 4th Ed., Macmillan Publishers, Ltd., 1977, p. 198. The following are specific examples, each of which may be optionally substituted: pyrazol-5-one, pyrazolidine-3,5-dione, imidaozoline-5-one, hydantoin, 2 or 4-thiohydantoin, 2-iminoxazolidine-4-one, 2-oxazoline-5-one, 2-thiooxasoline-2,4-dione, isorhodanine, rhodanine, thiophene-3-one, thiophene-3-one-1,1-dioxide, 3,3-dioxo[1,3]oxathiolane-5-one, indoline-2-one, indoline-3-one, 2-oxoindazolium, 5,7-dioxo-6,7-dihydrothiazolo[3,2-a]pyrimidine, 3,4-dihydroisoquinoline-4-one, 1,3-dioxane-4,6-dione (for example, Meldrum's acid), barbituric acid, 2-thiobarbituric acid, coumarin-2,4-dione, indazoline-2-one, pyrido[1,2-a]pyrimidine-1,3-dione, pyrazolo[15-b]quinozolone, pyrazolopyridone, and five or six-membered carbon rings (such as hexane-1,3-dione, pentane-1,3-dione, and indane-1,3-dione). Preferred examples are: pyrazole-5-one, pyrazolidine-3,5-dione, barbituric acid, 2-thiobarbituric acid, 1,3-dioxane-4,6-dione, 3,3-dioxo[1,3]oxathiolane-5-one, indanedione, pyrazolone, pyrazolinedione, and benzothiophene-one-dioxide. Each of $Za^{25}$ and $Za^{26}$ optimally denotes optionally substituted 1,3-dioxane-4,6-dione.

Examples of the substituents substituting on the acidic nucleus are: halogen atoms, alkyl groups (including cycloalkyl groups and bicycloalkyl groups), alkenyl groups (including cycloalkenyl groups and bicycloalkenyl groups), alkynyl groups, aryl groups, heterocyclic groups, cyano groups, hydroxyl groups, nitro groups, carboxyl groups, alkoxy groups, aryloxy groups, silyloxy groups, heterocyclooxy groups, acyloxy groups, carbamoyloxy groups, alkoxycarbonyloxy groups, aryloxycarbonyloxy groups, amino groups (including alkylamino groups and arylamino groups), acylamino groups, aminocarbonylamino groups, alkoxycarbonylamino groups, aryloxycarbonylamino groups, sulfamoylamino groups, alkyl and arylsulfonylamino groups, mercapto groups, alkylthio groups, arylthio groups, heterocyclothio groups, sulfamoyl groups, sulfo groups, alkyl and aryl sulfinyl groups, alkyl and arylsulfonyl groups, acyl groups, aryloxycarbonyl groups, alkoxycarbonyl groups, carbamoyl groups, aryl and heterocycloazo groups, imido groups, phosphino groups, phosphinyl groups, phosphinyloxy groups, phosphinylamino groups, and silyl groups. Of these, substituted or unsubstituted alkyl groups having 1 to 20 carbon atoms and substituted or unsubstituted aryl groups having 6 to 20 carbon atoms are preferred.

An acidic nucleus that is unsubstituted, substituted with a substituted or unsubstituted alkyl group having 1 to 20 carbon atoms, or substituted with a substituted or unsubstituted aryl group having 6 to 20 carbon atoms, is desirable.

$Ma^{27}$, $Ma^{28}$, and $Ma^{29}$ each independently denote a substituted or unsubstituted methine group. The substituent is desirably, for example, an alkyl group having 1 to 20 carbon atoms (such as a methyl group, ethyl group, or isopropyl group), a halogen atom (such as chlorine, bromine, iodine, or fluorine), an alkyoxy group having 1 to 20 carbon atoms (such as a methoxy group, ethoxy group, or isopropyl group), an aryl group having 6 to 26 carbon atoms (such as a phenyl group or 2-naphthyl group), a heterocyclic group having 0 to 20 carbon atoms (such as a 2-pyridyl group or a 3-pyridyl group), an aryloxy group having 6 to 20 carbon atoms (such as a phenoxy group, 1-naphthoxy group, or 2-naphthoxy group), an acylamino group having 1 to 20 carbon atoms (such as an acetylamino group or benzoylamino group), a carbamoyl group having 1 to 20 carbon atoms (such as an N,N-dimethylcarbamoyl group), a sulfo group, a hydroxy group, a carboxy group, an alkylthio group having 1 to 20 carbon atoms (such as a methylthio group), or a cyano group. Bonding with another methine group to form a ring structure is also possible, as is bonding with the atom groups denoted by $Za^{27}$ to $Za^{29}$ to form a ring structure.

Each of $Ma^{27}$, $Ma^{28}$, and $Ma^{29}$ desirably independently denotes an unsubstituted methine group, or a methine group substituted with an ethyl group, methyl group, or phenyl group. An unsubstituted methine group is optimal.

In general formula (V), $Ka^{23}$ denotes an integer ranging from 0 to 3. When $Ka^{23}$ denotes 2 or 3, plural $Ma^{27}$s and $Ma^{28}$s may be identical or different from each other. $Ka^{23}$ preferably denotes 2.

The dye in the form of a salt formed by the cationic compound of the present invention with the anionic dye moiety denoted by general formula (V) is neutral; the number of cations and the number of anions in the dye compound are equal. The number of cations and the number of anions are each preferably 3 to 10, more preferably 4 to 6.

In general formula (V), it is preferable that each of $Za^{25}$ and $Za^{26}$ denotes pyrazol-5-one, pyrazolidine-3,5-dione, barbituric acid, 2-thiobarbituric acid, 1,3-dioxane-4,6-dione, or 3,3-dioxo[1,3]oxathiolane-5-one that is either unsubstituted or substituted with a substituted or unsubstituted alkyl group having 1 to 20 carbon atoms, or a substituted or unsubstituted aryl group having 6 to 20 carbon atoms; $Ma^{27}$, $Ma^{28}$, and $Ma^{29}$ each independently denote an unsubstituted methine group, or a methine group substituted with an ethyl group, methyl group, or phenyl group; and $Ka^{23}$ denotes 2. Particularly preferably, $Za^{25}$ and $Za^{26}$ each independently denote 1,3-dioxane-4,6-dione that is either unsubstituted or substituted with a substituted or unsubstituted alkyl group having 1 to 20 carbon atoms, or a substituted or unsubstituted aryl group having 6 to 20 carbon atoms; $Ma^{27}$, $Ma^{28}$, and $Ma^{29}$ denote an unsubstituted methine group; and $K^{23}$ denotes 2.

General Formula (VI)

In general formula (VI), $Za^{21}$, $Za^{22}$, $Za^{23}$, and $Za^{24}$ each independently denote an atom group forming an acidic nucleus. The acidic nucleus is defined identically with that formed by $Za^{25}$ and $Za^{26}$ in general formula (V), and the specific examples are also identical. The acidic nucleus formed by $Za^{21}$, $Za^{22}$, $Za^{23}$, and $Za^{24}$ is preferably pyrazol-5-one, pyrazolidine-3,5-dione, barbituric acid, 2-thiobarubituric acid, 1,3-dioxane-4,6-dione, 3,3-dioxo[1,3]oxathiolane-5-one, indanedione, pyrazolone, pyrazolinedione, or benzothiophene-one-dioxide. Of these, 1,3-dioxane-4,6-dione is optimal.

$Ma^{21}$, $Ma^{22}$, $Ma^{23}$, $Ma^{24}$, $Ma^{25}$, and $Ma^{26}$ each independently denote a substituted or unsubstituted methine group defined identically with those of $Ma^{27}$, $Ma^{28}$, and $Ma^{29}$ of general formula (V) as well as having the same specific examples and preferred examples. $Ma^{21}$, $Ma^{22}$, $Ma^{23}$, $Ma^{24}$, $Ma^{25}$, and $Ma^{26}$ preferably denote unsubstituted methine groups.

L denotes a divalent linkage group that does not form a pi-conjugation with two bonds. The divalent linkage group is not specifically limited other than that it doesn't form a pi-conjugation between chromophores to which it bonds; it preferably denotes a linkage group having 0 to 100 carbon atoms, preferably 1 to 20 carbon atoms, comprised of one or a combination of two or more of alkylene groups (having 1 to 20 carbon atoms, such as a methylene group, ethylene group, propylene group, butylene group, or pentylene group), arylene groups (having 6 to 26 carbon atoms, such as a phenylene group or naphthylene group), alkenylene groups (having 2 to 20 carbon atoms, such as an ethenylene group or propenylene group), alkynylene groups (having 2 to 20, such as an ethynylene group or propynylene group), —CO—N($R^{101}$)—, —CO—O—, —$SO_2$—N($R^{102}$)—, —$SO_2$—O—, —N($R^{103}$)—CO—N($R^{104}$)—, —$SO_2$—, —SO—, —S—, —O—, —CO—, —N($R^{105}$)—, and heterylene groups (having 1 to 26 carbon atoms, such as 6-chloro-1,3,5-triazyl-2,4-diyl or pyrimidine-2,4-diyl group). The above $R^{101}$, $R^{102}$, $R^{103}$, $R^{104}$, and $R^{105}$ each independently denote a hydrogen atom, substituted or unsubstituted alkyl group, or substituted or unsubstituted aryl group. One or more linkage groups denoted by L may be present between the two chromophores to which they bond, and plural (preferably 2) linkage groups may bond together to form a ring.

L preferably denotes two alkylene groups (preferably, ethylene groups) that bond together to form a ring. Of these, the case where a five or six-membered ring (preferably a cyclohexyl) is formed is further preferred.

Desirable specific examples of the oxonol dye will be given below. However, the present invention is not limited thereto.

[Chem. 37]

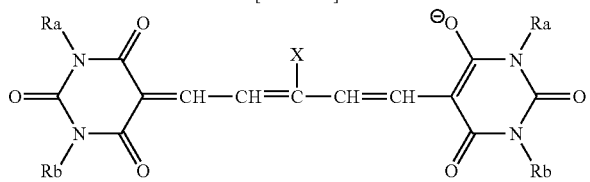

| No. | Ra | Rb | X |
|---|---|---|---|
| B-1 | Phenyl | H | H |
| B-2 | Phenyl | H | $CH_3$ |
| B-3 | Phenyl | H | $C_2H_5$ |
| B-4 | Phenyl | H | Phenyl |
| B-5 | Phenyl | H | —$CH_2$—C$_6$H$_5$ |
| B-6 | Phenyl | H | Cl |
| B-7 | Phenyl | H | $NHCOCH_3$ |
| B-8 | Phenyl | H | $OCH_3$ |
| B-9 | Phenyl | H | 4-pyridyl |
| B-10 | Phenyl | H | N-methyl-2-pyrrolidinonyl |
| B-11 | $CH_3$ | H | H |
| B-12 | $CH_3$ | H | Phenyl |
| B-13 | n-$C_4H_9$ | H | H |
| B-14 | H | H | H |
| B-15 | H | H | $CH_3$ |
| B-16 | Phenyl | Phenyl | H |
| B-17 | Phenyl | Phenyl | Phenyl |
| B-18 | Phenyl | Phenyl | $CH_3$ |
| B-19 | $CH_3$ | $CH_3$ | $CH_3$ |
| B-20 | $CH_3$ | $CH_3$ | H |
| B-21 | $CH_3$ | $CH_3$ | Phenyl |
| B-22 | $CH_3$ | $CH_3$ | $OCH_3$ |

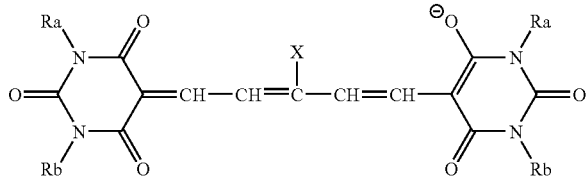

| No. | Ra | Rb | X |
|---|---|---|---|
| B-23 | H | H | H |
| B-24 | $CH_3$ | H | H |
| B-25 | $CH_3$ | H | Phenyl |

-continued

| | | | |
|---|---|---|---|
| B-26 | Phenyl | H | H |
| B-27 | Phenyl | H | Phenyl |
| B-28 | Phenyl | Phenyl | H |
| B-29 | C$_2$H$_5$ | C$_2$H$_5$ | H |
| B-30 | C$_2$H$_5$ | C$_2$H$_5$ | CH$_3$ |
| B-31 | C$_2$H$_5$ | Phenyl | H |

[Chem. 38]

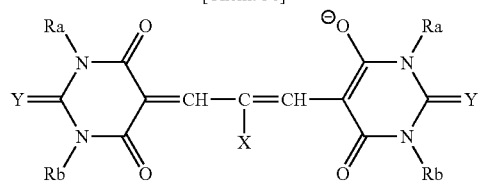

| No. | Ra | Rb | X | Y |
|---|---|---|---|---|
| B-32 | H | H | H | O |
| B-33 | H | H | CH$_3$ | O |
| B-34 | Phenyl | H | H | O |
| B-35 | Phenyl | H | CH$_3$ | O |
| B-36 | CH$_3$ | CH$_3$ | CH$_3$ | O |
| B-37 | CH$_3$ | CH$_3$ | H | O |
| B-38 | H | H | H | S |
| B-39 | Phenyl | H | H | S |
| B-40 | C$_2$H$_5$ | C$_2$H$_5$ | H | S |
| B-41 | C$_2$H$_5$ | C$_2$H$_5$ | CH$_3$ | S |

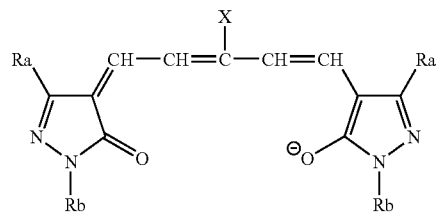

| No. | Ra | Rb | X |
|---|---|---|---|
| B-42 | COOC$_2$H$_5$ | H | H |
| B-43 | COOC$_2$H$_5$ | CH$_3$ | H |
| B-44 | COOC$_2$H$_5$ | Phenyl | H |
| B-45 | COOC$_2$H$_5$ | 2,4,6-trichlorophenyl | H |
| B-46 | COOC$_2$H$_5$ | CONHC$_4$H$_9$(n) | H |
| B-47 | CN | Phenyl | H |
| B-48 | COCH$_3$ | Phenyl | H |
| B-49 | CONHCH$_3$ | Phenyl | H |
| B-50 | CONHC$_4$H$_9$(n) | CONHC$_4$H$_9$(n) | H |
| B-51 | | Phenyl | H |
| B-52 | Phenyl | 2,4,6-trichlorophenyl | CH$_3$ |
| B-53 | SO$_2$CH$_3$ | Phenyl | H |
| B-54 | NHSO$_2$CH$_3$ | Phenyl | H |
| B-55 | CH$_3$ | Phenyl | H |
| B-56 | CH$_3$ | Phenyl | Phenyl |
| B-57 | OC$_2$H$_5$ | Phenyl | H |
| B-58 | NHCOCH$_3$ | Phenyl | H |
| B-59 | NH$_2$ | Phenyl | H |

-continued

| | | | |
|---|---|---|---|
| B-60 | CF$_3$ | Phenyl | H |
| B-61 | COOC$_2$H$_5$ | Phenyl | CH$_3$ |
| B-62 | CN | Phenyl | CH$_3$ |

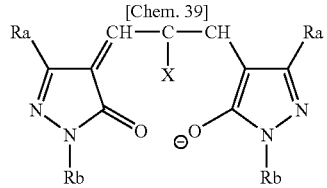
[Chem. 39]

| No. | Ra | Rb | X |
|---|---|---|---|
| B-63 | COOC$_2$H$_5$ | Phenyl | H |
| B-64 | CN | Phenyl | H |
| B-65 | CONHC$_4$H$_9$(n) | Phenyl | H |
| B-66 | CN | Phenyl | Cl |
| B-67 | NHCOCH$_3$ | Phenyl | H |
| B-68 | CH$_3$ | Phenyl | H |
| B-69 | CH$_3$ | CH$_3$ | CH$_3$ |
| B-70 | NH$_2$ | Phenyl | H |

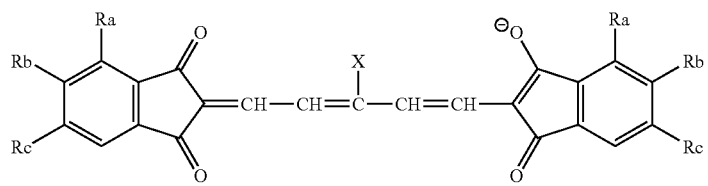

| No. | Ra | Rb | Rc | X |
|---|---|---|---|---|
| B-71 | H | H | H | H |
| B-72 | H | CH$_3$ | H | H |
| B-73 | H | t-C$_4$H$_9$ | H | H |
| B-74 | NO$_2$ | H | H | H |
| B-75 | NH$_2$ | H | H | H |
| B-76 | H | Phenyl | H | H |
| B-77 | H | Cl | Cl | H |
| B-78 | H | H | H | Phenyl |
| B-79 | H | H | H | CH$_3$ |
| B-80 | H | H | H | CONH$_2$ |

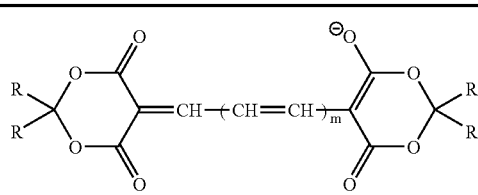

| No. | R | m |
|---|---|---|
| B-81 | CH$_3$ | 3 |
| B-82 | CH$_3$ | 2 |
| B-83 | CH$_3$ | 1 |
| B-84 | 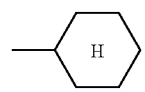 | 3 |
| B-85 | 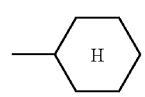 | 2 |
| B-86 | CH$_2$CH$_2$OCH$_3$ | 3 |
| B-87 | CH$_2$CH$_2$OCH$_3$ | 2 |
| B-88 | Phenyl | 2 |
| B-89 | Phenyl | 3 |

[Chem. 40]
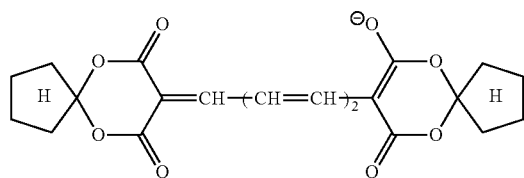
B-90
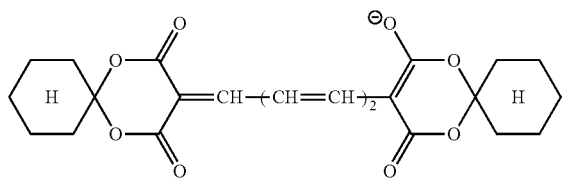
B-91
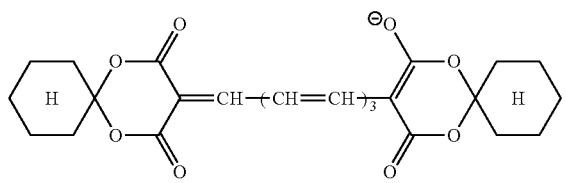
B-92
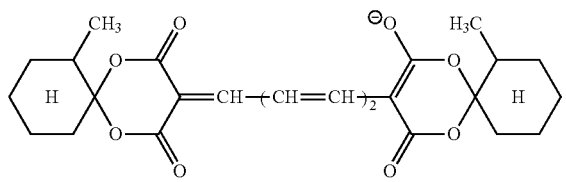
B-93
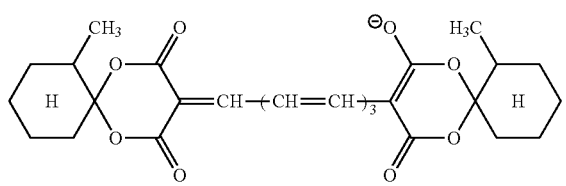
B-94
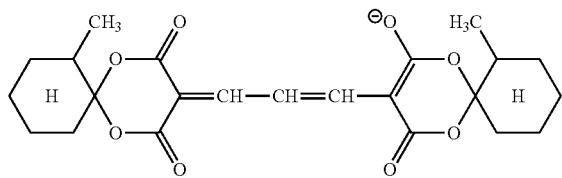
B-95
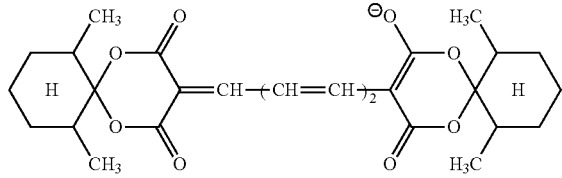
B-96

-continued

[Chem. 41]

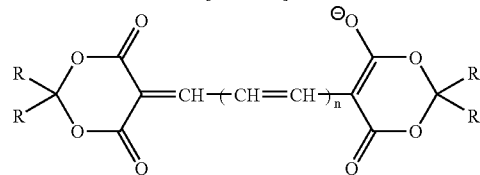

| No. | Ra | Rb | n |
|---|---|---|---|
| B-97 | CH$_3$ | C$_2$H$_5$ | 3 |
| B-98 | CH$_3$ | Phenyl | 3 |
| B-99 | CH$_3$ | Phenyl | 2 |
| B-100 | CH$_3$ | CH(CH$_3$)$_2$ | 2 |
| B-101 | CH$_3$ | CH(CH$_3$)$_2$ | 3 |
| B-102 | CH$_3$ | CF$_3$ | 3 |

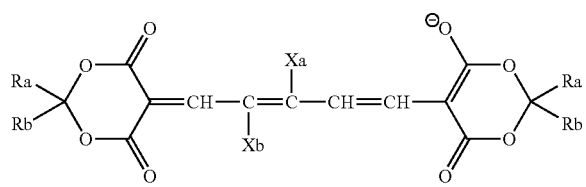

| No. | Ra | Rb | Xa | Xb |
|---|---|---|---|---|
| B-103 | CH$_3$ | CH$_3$ | CH$_3$ | H |
| B-104 | CH$_3$ | CH$_3$ | Phenyl | H |
| B-105 | CH$_3$ | CH$_3$ | OCH$_3$ | H |
| B-106 | CH$_3$ | CH$_3$ | 4-methylpiperidinyl | H |
| B-107 | CH$_3$ | CH$_3$ | Cl | H |
| B-108 | CH$_3$ | CH$_3$ | H | CH$_3$ |
| B-109 | CH$_3$ | CH$_2$CO$_2$C$_2$H$_5$ | CH$_3$ | H |

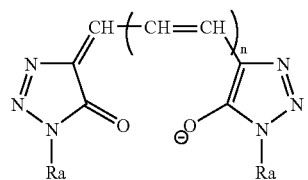

| No. | Ra | n |
|---|---|---|
| B-110 | Phenyl | 2 |
| B-111 | Phenyl | 1 |
| B-112 | CH$_3$ | 2 |
| B-113 | CH$_3$ | 1 |

[Chem. 42]

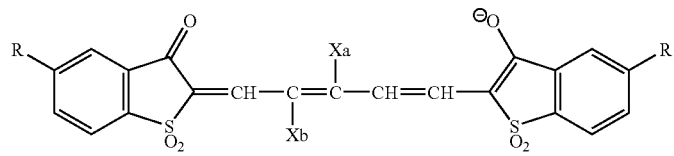

| No. | R | Xa | Xb |
|---|---|---|---|
| B-114 | H | H | H |
| B-115 | H | Phenyl | H |
| B-116 | OCH$_3$ | Phenyl | H |
| B-117 | H | OCH$_3$ | H |
| B-118 | H | Phenoxy | H |

-continued
| | | | |
|---|---|---|---|
| B-119 | H | CH$_3$ | H |
| B-120 | H | C$_2$H$_5$ | H |
| B-121 | H | 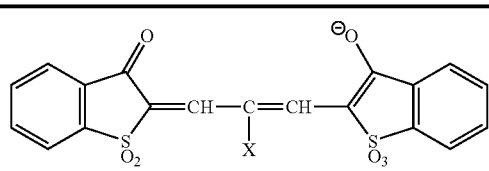 | H |
| B-122 | H | H | CH$_3$ |
| B-123 | H | Cl | H |
| B-124 | H | 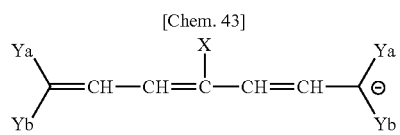 | H |
| B-125 | H | CONH$_2$ | H |
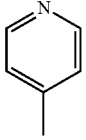
| No. | X |
|---|---|
| B-126 | H |
| B-127 | CH$_3$ |
| B-128 | C$_2$H$_5$ |
| B-129 | Phenyl |
| B-130 |  |
| B-131 | Cl |
[Chem. 43]
| No. | X | Ya | Yb |
|---|---|---|---|
| B-132 | H | CN | CN |
| B-133 | CH$_3$ | CN | CN |
| B-134 | OCH$_3$ | CN | —COCH$_3$ |
| B-135 | Phenyl | CO$_2$C$_2$H$_5$ | CO$_2$C$_2$H$_5$ |
| B-136 | H | CO$_2$nC$_4$H$_9$ | CO$_2$nC$_4$H$_9$ |
| B-137 | H | —COCH$_3$ | —COCH$_3$ |
| B-138 | H | CN | CO$_2$$^{(n)}$C$_4$H$_9$ |
| B-139 | Phenyl | CN | CO$_2$CH$_3$ |
| B-140 | H | —COCH$_3$ | CO$_2$CH$_3$ |

-continued
| | | | |
|---|---|---|---|
| B-141 | H | —C(=O)—C₆H₅ | $CO_2nC_4H_9$ |
| B-142 | $C_2H_5$ | —C(=O)CH₃ | $CON(C_2H_5)_2$ |
| B-143 | Phenyl | CN | $SO_2CH_3$ |
| B-144 | Phenyl | CN | —SO₂—C₆H₅ |
| B-145 | H | $CO_2C_2H_5$ | —SO₂—C₆H₅ |
| B-146 | H | —C(=O)NHCH₃ | $SO_2CH_3$ |
| B-147 | H | —P(=O)(OC₂H₅)₃ | $CO_2C_2H_5$ |
| B-148 | H | $NO_2$ | $CO_2C_2H_5$ |
| B-149 | Phenyl | $NO_2$ | $CO_2{}^{(n)}C_4H_9$ |
| B-150 | $CH_3$ | $SO_2NH$—C₆H₅ | $CO_2CH_3$ |
| B-151 | H | —C(=O)N(CH₃)₂ | —C(=O)N(CH₃)₂ |
$$Ya\text{-}C(Yb)=CH\text{-}CH=CH\text{-}CH=CH\text{-}CH=CH\text{-}C(Yb)(Ya)^{\ominus}$$
| No. | Ya | Yb |
|---|---|---|
| B-152 | CN | CN |
| B-153 | CN | $CO_2{}^{(n)}C_4H_9$ |
| B-154 | CN | —SO₂—C₆H₅ |
[Chem. 44]
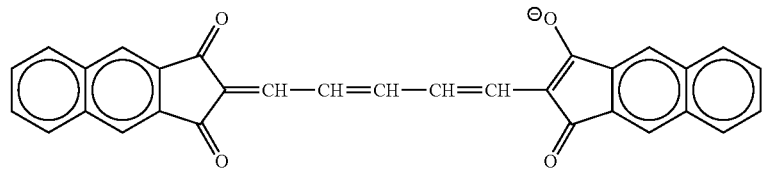
B-155
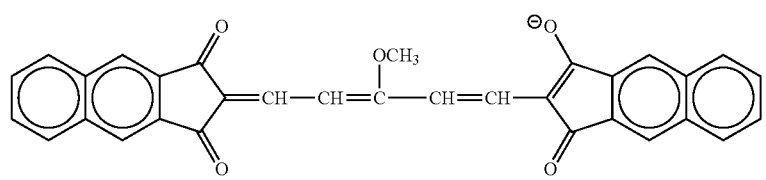
B-156

-continued
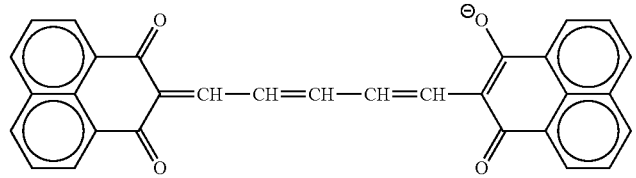
B-157
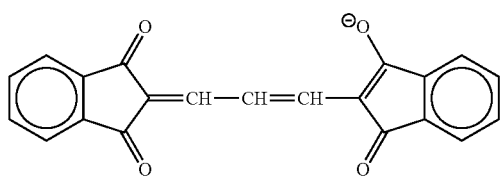
B-158
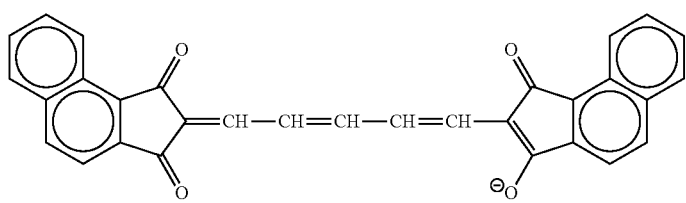
B-159
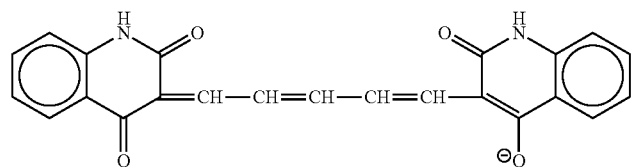
B-160
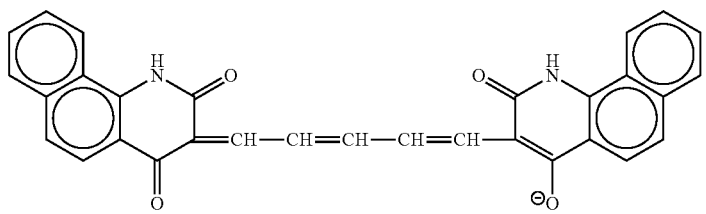
B-161
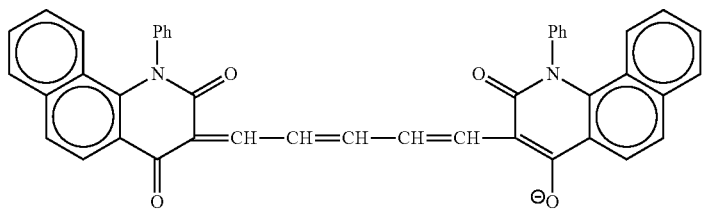
B-162
(Ph means phenyl, of which meaning is the same, hereinafter.)
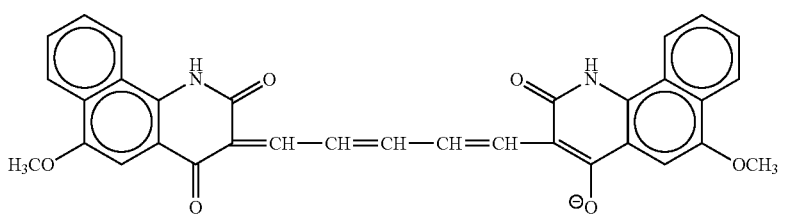
B-163

-continued
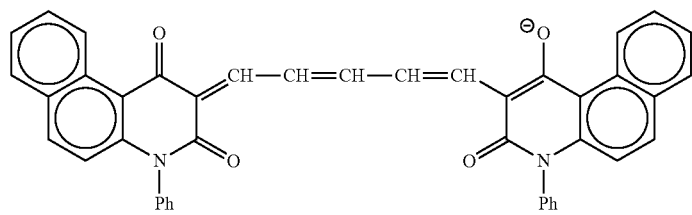
B-164
[Chem. 45]
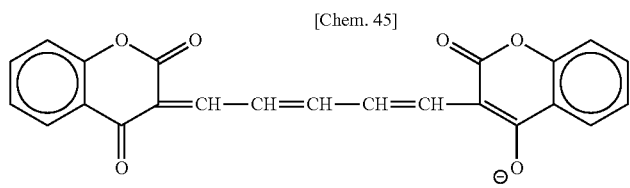
B-165
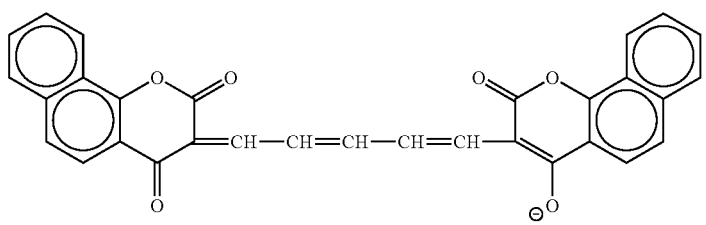
B-166
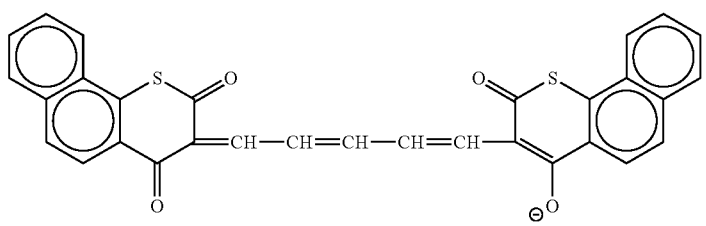
B-167
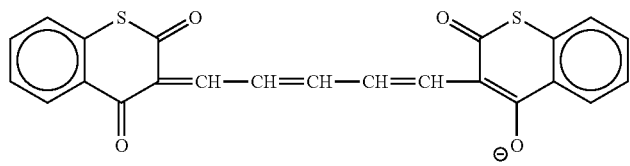
B-168
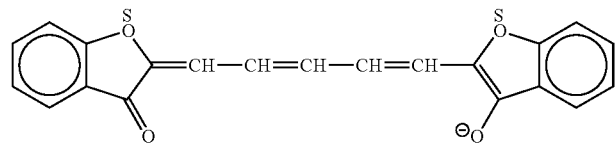
B-169
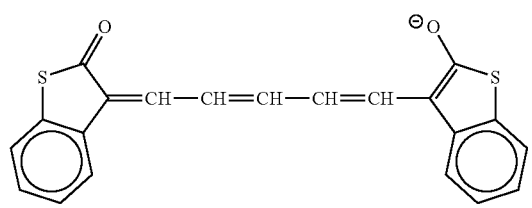
B-170
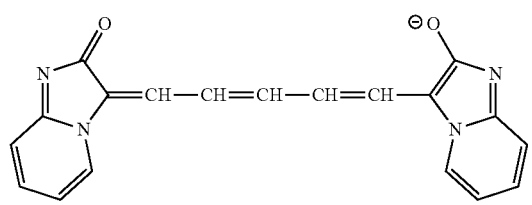
B-171

-continued
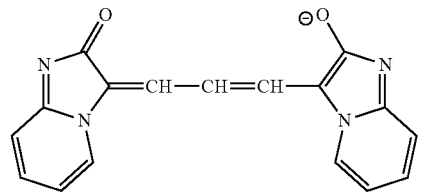
B-172
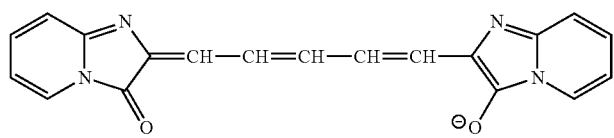
B-173
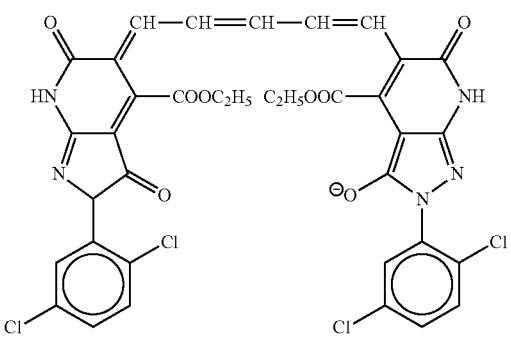
B-174
[Chem. 46]
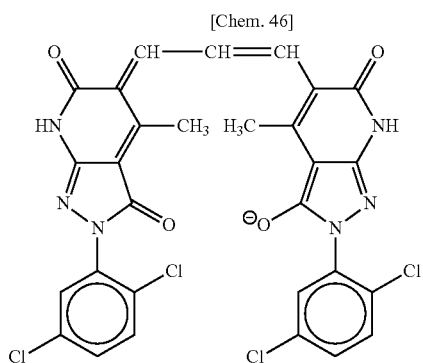
B-175
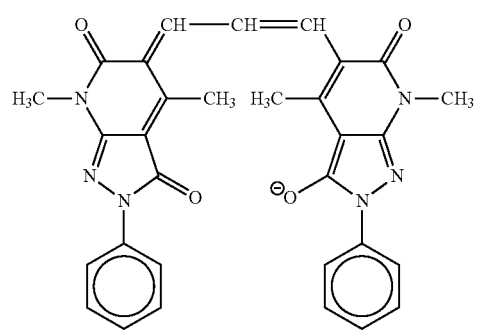
B-176

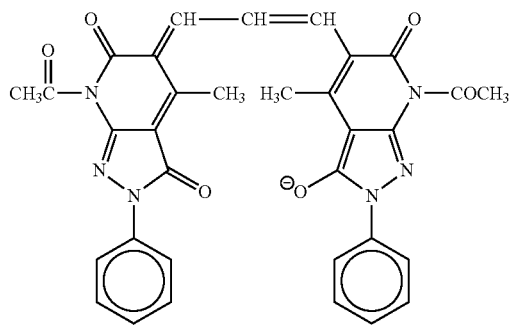
B-177
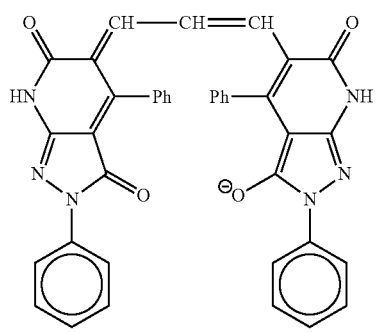
B-178
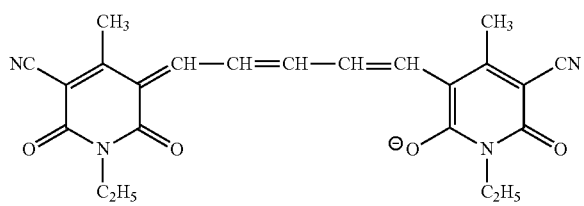
B-179
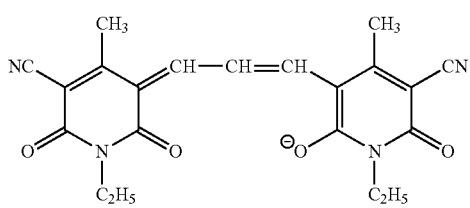
B-180
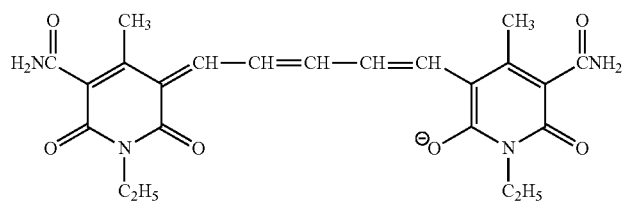
B-181
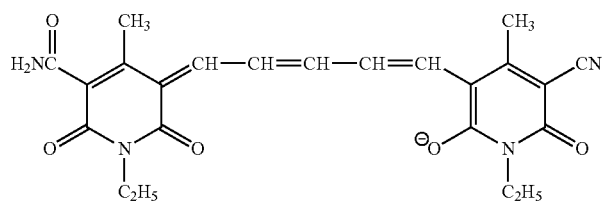
B-182

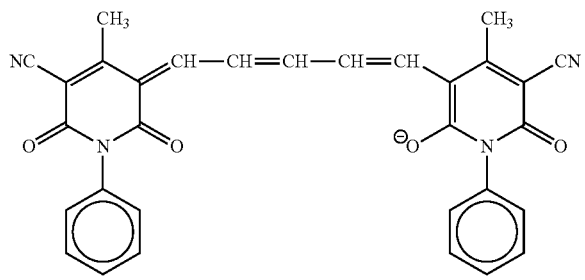
B-183
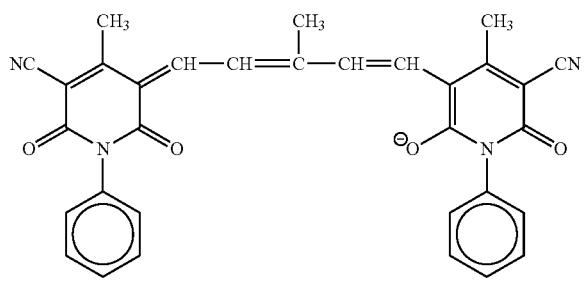
B-184
[Chem. 47]
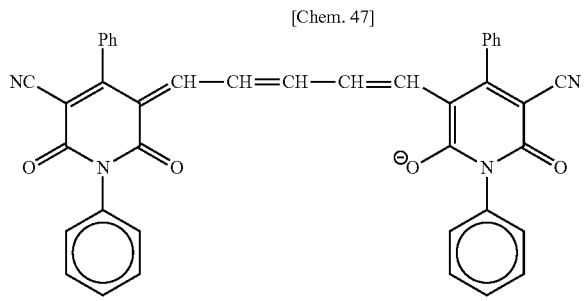
B-185
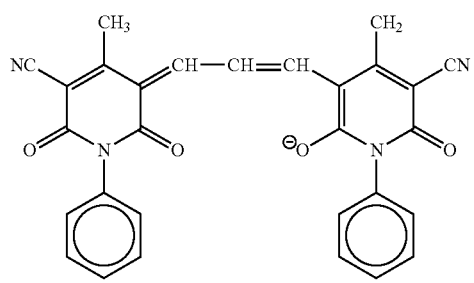
B-186
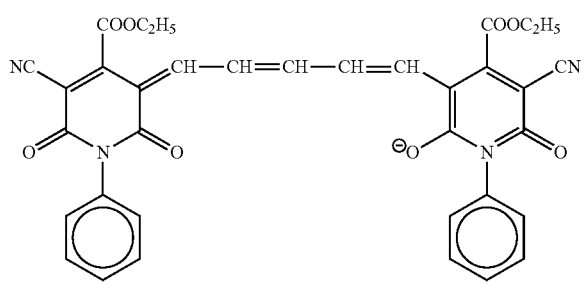
B-187
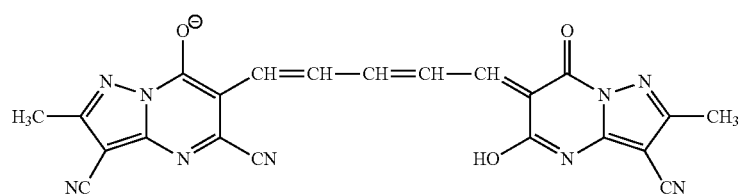
B-188

-continued
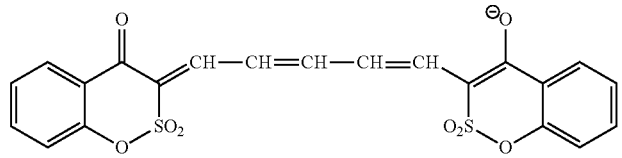
B-189
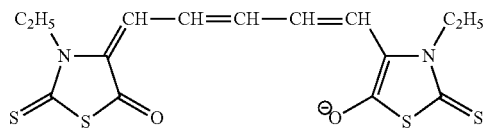
B-190
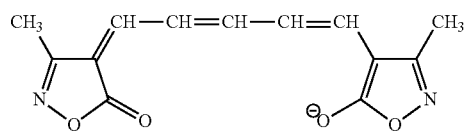
B-191
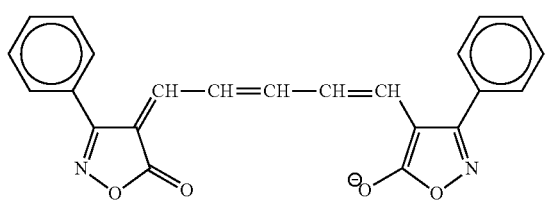
B-192
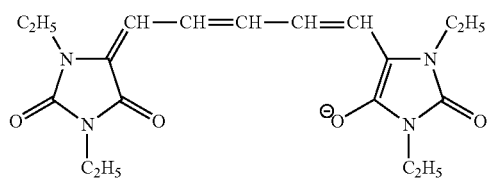
B-193
[Chem. 48]
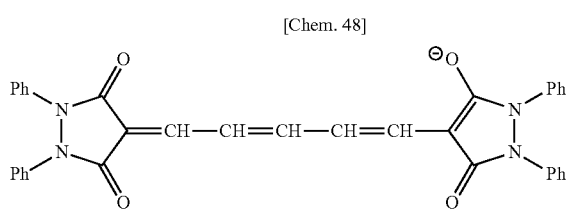
B-194
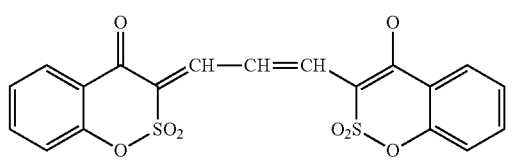
B-195
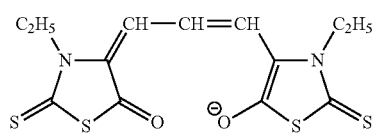
B-196
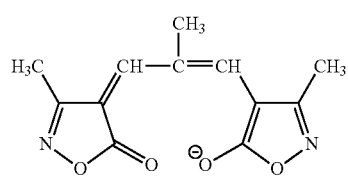
B-197

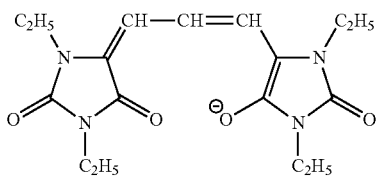 B-198
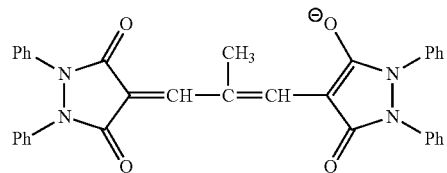 B-199
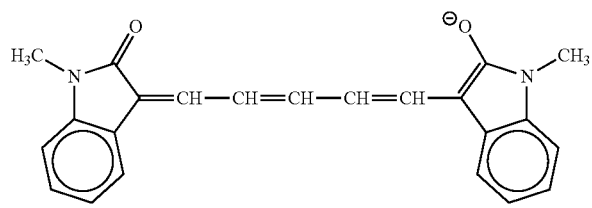 B-200
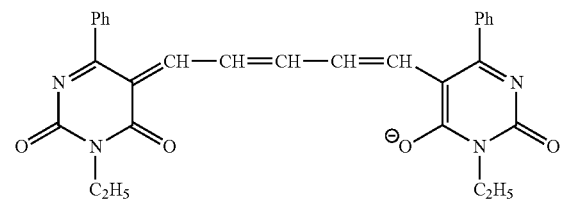 B-201
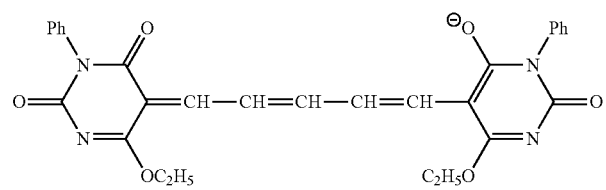 B-202
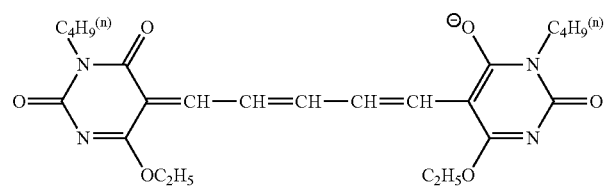 B-203
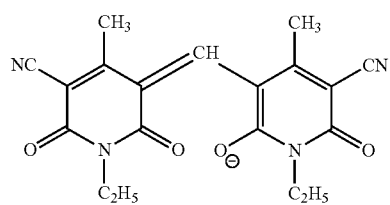 B-204

[Chem. 49]
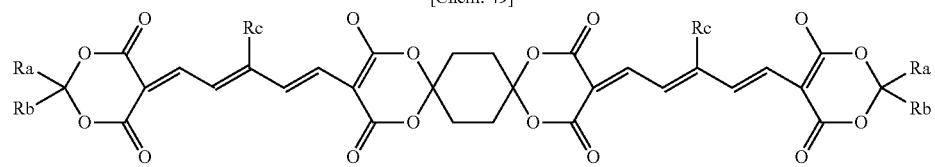
| Compound No. | Ra | Rb | Rc |
| --- | --- | --- | --- |
| C-1 | CH$_3$ | C$_2$H$_5$ | H |
| C-2 | CH$_3$ | C$_4$H$_9$-t | H |
| C-3 | C$_2$H$_5$ | C$_3$H$_7$-i | H |
| C-4 | C$_2$H$_5$ | C$_2$H$_5$ | H |
| C-5 | CH$_3$ | C$_3$H$_7$-n | H |
| C-6 | CH$_3$ | C$_3$H$_7$-n | CH$_3$ |
| C-7 | CH$_3$ | CH$_2$OCH$_3$ | H |
| C-8 | CH$_3$ | C$_2$H$_4$CO$_2$CH$_3$ | H |
| C-9 | CH$_3$ | C$_2$H$_4$CO$_2$C$_2$H$_5$ | H |
| C-10 | CH$_3$ | CH$_3$ | H |
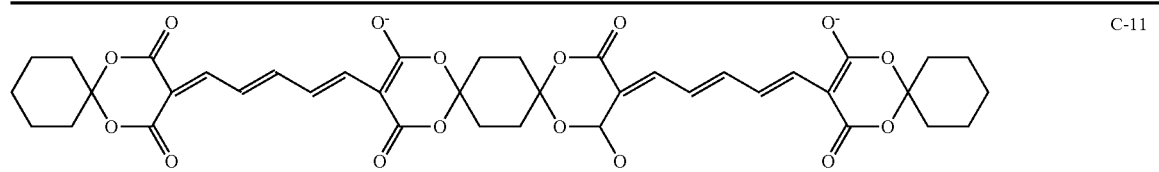
C-11
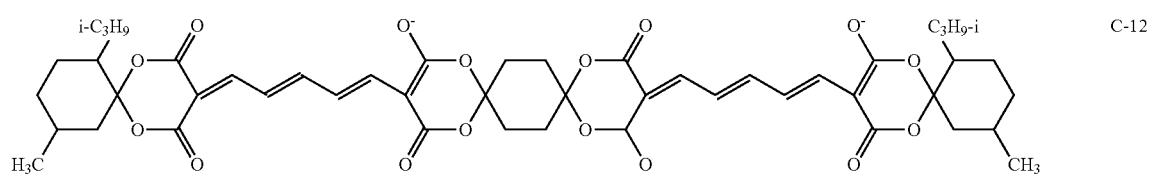
C-12
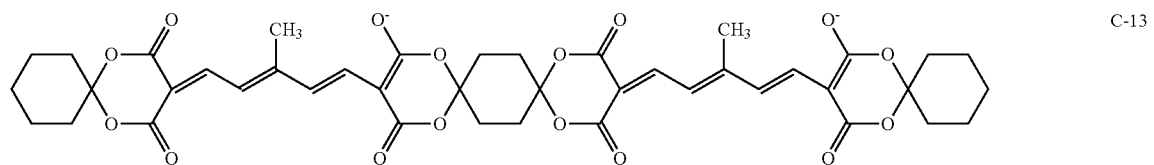
C-13
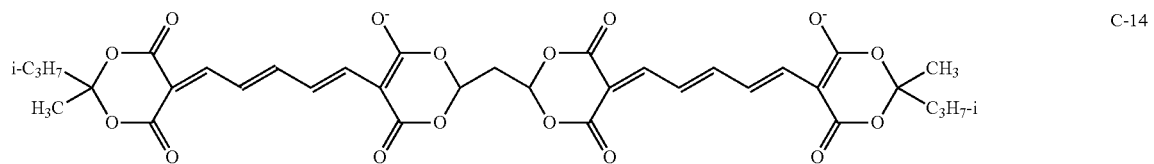
C-14
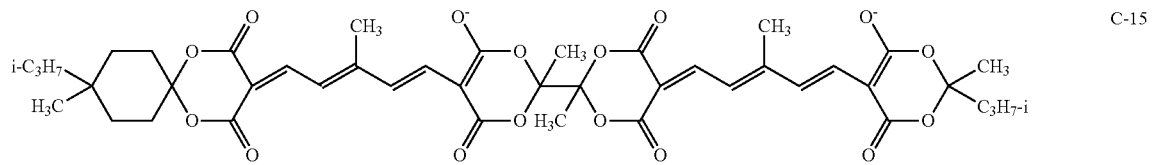
C-15
[Chem. 50]
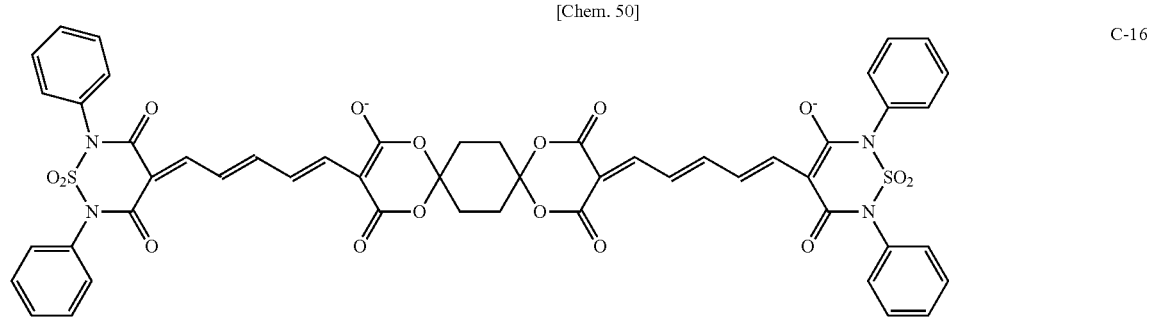
C-16

-continued

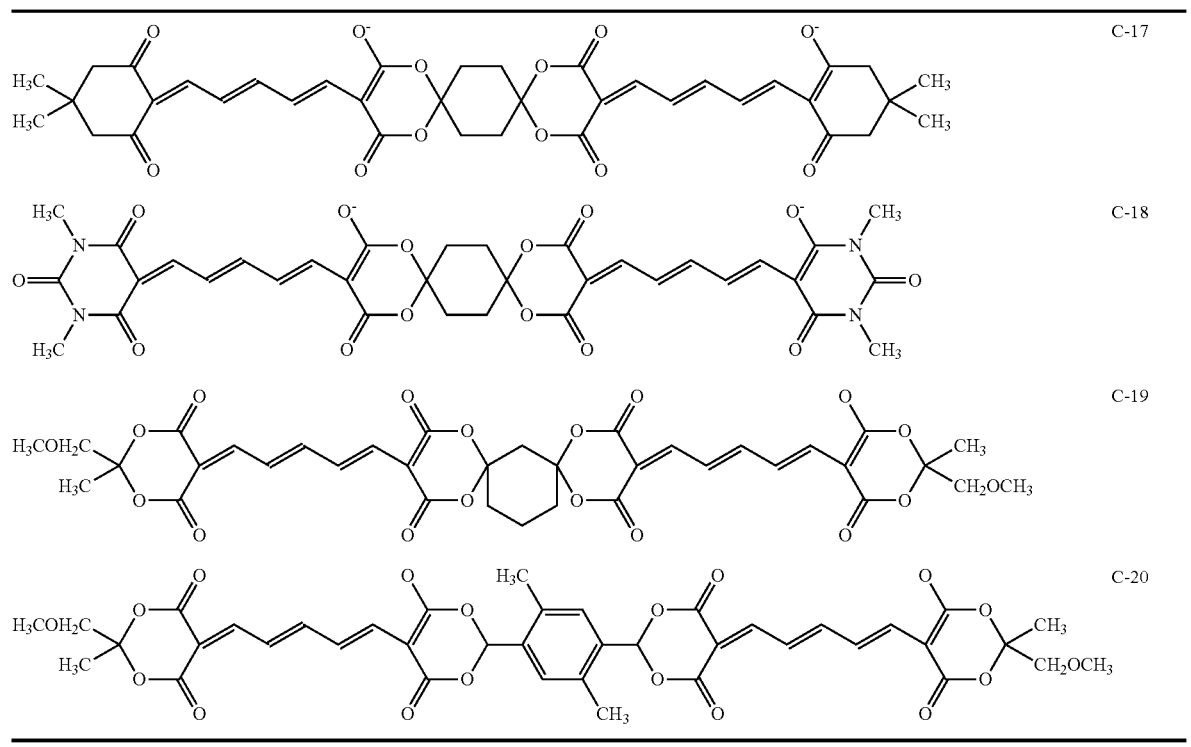

Generally, oxonol dyes can be synthesized by the condensation reaction of a corresponding active methylene compound and methine source (a compound used to introduce a methine group into a methine dye). For details regarding such compounds, Japanese Examined Patent Publication (KOKOKU) Showa Nos. 39-22069, 43-3504, 52-38056, 54-38129, 55-10059, and 58-35544; Japanese Unexamined Patent Publication (KOKAI) Showa Nos. 49-99620, 52-92716, 59-16834, 63-316853, and 64-40827; British Patent No. 1,133,986; U.S. Pat. Nos. 3,247,127, 4,042,397, 4,181,225, 5,213,956, and 5,260,179 can be referred.

European Patent EP1424691A2 discloses a method for synthesizing bis-oxonol dyes.

Desirable specific examples of the dye compound in which the cationic compound of the present invention and an anionic dye form a salt will be given below. However, the present invention is not limited to these examples.

[Table 1]

TABLE 1

| Compound No. | Anionic part | Cationic part |
|---|---|---|
| D-1 | C-5 | V-1 |
| D-2 | C-5 | V-2 |
| D-3 | C-5 | V-3 |
| D-4 | C-5 | V-4 |
| D-5 | C-1 | V-5 |
| D-6 | C-2 | V-6 |
| D-7 | C-3 | V-7 |
| D-8 | C-4 | V-9 |
| D-9 | C-5 | V-8 |
| D-10 | C-6 | V-10 |
| D-11 | C-7 | V-11 |
| D-12 | C-8 | V-12 |
| D-13 | C-9 | V-13 |
| D-14 | C-10 | V-14 |
| D-15 | C-11 | V-15 |
| D-16 | C-12 | V-16 |

TABLE 1-continued

| Compound No. | Anionic part | Cationic part |
|---|---|---|
| D-17 | C-13 | V-17 |
| D-18 | C-14 | V-18 |
| D-19 | C-15 | V-19 |
| D-20 | C-16 | V-20 |
| D-21 | C-17 | V-21 |
| D-22 | C-18 | V-22 |
| D-23 | C-19 | V-23 |
| D-24 | C-20 | V-24 |
| D-25 | C-5 | V-25 |
| D-26 | C-9 | V-26 |
| D-27 | C-5 | V-27 |
| D-28 | C-9 | V-28 |
| D-29 | C-5 | V-29 |
| D-30 | C-9 | V-30 |
| D-31 | B-1 | V-1 |
| D-32 | B-20 | V-2 |
| D-33 | B-29 | V-1 |
| D-34 | B-37 | V-3 |
| D-35 | B-45 | V-4 |
| D-36 | B-49 | V-3 |
| D-37 | B-65 | V-3 |
| D-38 | B-71 | V-6 |
| D-39 | B-85 | V-1 |
| D-40 | B-91 | V-3 |
| D-41 | B-94 | V-4 |
| D-42 | B-99 | V-8 |
| D-43 | B-104 | V-9 |
| D-44 | B-114 | V-12 |
| D-45 | B-127 | V-15 |
| D-46 | B-138 | V-18 |
| D-47 | B-155 | V-21 |
| D-48 | B-164 | V-24 |
| D-49 | B-169 | V-25 |
| D-50 | B-191 | V-27 |
| D-51 | B-194 | V-28 |
| D-52 | B-201 | V-30 |

[Table 2]

TABLE 2

| Compound No. | Anionic part | Cationic part |
| --- | --- | --- |
| D-53 | C-5 | V-31 |
| D-54 | C-9 | V-32 |
| D-55 | C-4 | V-33 |
| D-56 | C-9 | V-34 |
| D-57 | C-9 | V-35 |
| D-58 | C-11 | V-36 |
| D-59 | C-9 | V-37 |
| D-60 | C-9 | V-38 |
| D-61 | C-9 | V-39 |
| D-62 | C-5 | V-40 |
| D-63 | C-5 | V-41 |
| D-64 | C-9 | V-42 |
| D-65 | C-5 | V-43 |
| D-66 | C-9 | V-44 |
| D-67 | C-9 | V-45 |
| D-68 | C-11 | V-46 |
| D-69 | C-9 | V-47 |
| D-70 | C-5 | V-48 |
| D-71 | C-9 | V-49 |
| D-72 | C-5 | V-50 |
| D-73 | C-5 | V-51 |
| D-74 | C-5 | V-52 |
| D-75 | C-9 | V-53 |
| D-76 | C-5 | V-54 |
| D-77 | C-5 | V-55 |
| D-78 | C-5 | V-56 |
| D-79 | C-5 | V-57 |
| D-80 | C-4 | V-58 |
| D-81 | C-5 | V-59 |
| D-82 | C-9 | V-60 |
| D-83 | C-5 | V-61 |
| D-84 | C-9 | V-62 |
| D-85 | C-5 | V-63 |
| D-86 | C-9 | V-64 |
| D-87 | C-5 | V-65 |
| D-88 | C-5 | V-66 |
| D-89 | C-5 | V-67 |
| D-90 | C-5 | V-68 |
| D-91 | C-5 | V-69 |
| D-92 | C-9 | V-70 |
| D-93 | C-5 | V-71 |
| D-94 | C-9 | V-72 |

In addition to the above-described oxonol dye, a dissociative azo dye, azomethine dye, or methine dye having chromophore in the form of a dissociative group (hydroxyl group, amino group, or the like), or an azo dye, azomethine dye, methine dye, quinone-based dye, diaryl and triarylmetane-based dye, phthalocyanine dye, indigo dye, condensed ring-based dye, styryl-based dye, spiropyran, spirooxazine derivative, diarylethene derivative, squalium, croconium derivative, or the like, substituted with a dissociative group in addition to chromophore can be employed as the above anionic dye. The dyes described by Makoto OGAWARA, Ken MATSUOKA, Tsuneyoshi HIRAJIMA, and Teijiro KITAO (Kodansha) in "functional Dyes" are specific structural examples.

The dye compound of the present invention can be readily obtained by anionic exchange of a salt (hydrochloride or the like) of the cationic compound of the present invention. The dye compound that is obtained can be purified by known methods. Confirmation that the dye compound of the present invention has been obtained can be done by a known analysis method such as NMR.

The dye compound of the present invention affords good solubility during the preparation of a dye coating liquid, good dissolution stability over time in the coating liquid, and good coating properties (coating film smoothness) when using a high-concentration coating liquid. Thus, manufacturing suitability can be improved by using the dye compound of the present invention as a dye for a recording layer of an optical information recording medium.

Since the dye compound of the present invention also affords good recording characteristics, it yields an optical information recording medium with good recording sensitivity and good writing precision when used as a dye for a recording layer of an optical information recording medium. The details of how to use the dye compound of the present invention as a dye for a recording layer are set forth further below for the optical information recording medium of the present invention.

[Optical Information Recording Medium]

The optical information recording medium of the present invention comprises a recording layer on a substrate, wherein the recording layer comprises the dye compound of the present invention.

The recording layer may comprise just one, or may comprise a combination of two or more dye compounds of the present invention. The content of the dye compound is preferably 1 to 100 percent, more preferably 5 to 100 percent, and particularly preferably, 10 to 100 percent.

In addition to the dye compound of the present invention, both organic and inorganic components may be present in the recording layer. Specific examples of such components are dyes other than the dye compound of the present invention. Such combined dyes are preferably organic dyes, specific examples of which are azo dyes, cyanine dyes, oxonol dyes, pyromethene dyes, and phthalocyanine dyes. More specific examples are the oxonol dyes described in Japanese Unexamined Patent Publication (KOKAI) Heisei No. 10-279103; Japanese Unexamined Patent Publication (KOKAI) Nos. 2000-108520, 2002-59652, 2002-249674, 2003-39831, and 2004-188968. When combining additional dyes with the dye compound of the present invention as recording materials, from the perspectives of enhancing recording characteristics and manufacturing suitability, the mixture is desirably one in which the ratio of the dye compound of the present invention is from 60 to 100 mass percent and the ratio of the other dye is from 0 to 40 mass percent relative to the total dye component in the recording layer.

The optical information recording medium of the present invention is not specifically limited other than that the dye compound of the present invention be comprised in the recording layer, and is desirably a recordable optical recording medium. When applying the optical information recording medium of the present invention to a CD-R, the configuration is desirably one in which a recording layer comprising the dye compound of the present invention, a photoreflective layer, and a protective layer are present in this order on a transparent disklike substrate 1.2±0.2 mm in thickness on which pregrooves are formed with a track pitch of 1.4 to 1.8 micrometers.

The optical information recording medium of the present invention can also be a recordable DVD. Recordable DVDs can be those having a single recording layer and those having a double recording layer. The present invention may be adapted to either embodiment. In addition, recordable DVDs can be DVD-Rs or DVD+Rs; the present invention can be adapted to either embodiment.

Recordable DVDs having a single recording layer may adopt a layered structure having a recording layer between a pair of substrates (for example, in the order of a substrate, a recording layer, and a protective substrate (dummy substrate)). Additionally, the suitably formation of a reflective layer, a protective layer, and the like is also preferred. FIG. 1 shows an example of a recordable DVD having such a layer configuration.

The example of an optical information recording medium given below is a preferred embodiment of a DVD-R optical information recording medium having a single recording layer.

An optical information recording medium in which a laminate comprising a recording layer comprising the dye compound of the present invention and a photoreflective layer on a transparent disklike substrate 0.6±0.1 mm in thickness on which pregrooves have been formed with a track pitch of 0.6 to 0.9 micrometers is adhered to a transparent disklike protective substrate identical in shape to the disklike substrate of the laminate so that the recording layer is on the inside and the thickness of the optical information recording medium is 1.2±0.2 mm. In the above DVD-R optical information recording medium, it is possible to further provide a protective layer on the photoreflective layer.

The dye compound in which the oxonol dye denoted by general formula (VI) is combined with the cationic part denoted by general formula (III) or (IV) is preferable as the dye compound of the present invention employed in the single recording layer.

In a recordable DVD having two recording layers, a layer configuration in which two or more recording layers are present between a pair of opposing substrates (for example, comprising a first substrate, a first recording layer, a second recording layer, and a second substrate in this order) may also be adopted. FIG. 2 shows an example of a recordable DVD comprising two recording layers.

The recordable DVD shown in FIG. 2 has the configuration in which a first substrate 14 having a first recording layer 22 and a second substrate 18 having a second recording layer 28 are laminated with an intermediate layer 20 between them. A reflective layer 24 is provided on first recording layer 22, a barrier layer 30 is provided between intermediate layer 20 and second recording layer 28, and a reflective layer 26 is provided between second recording layer 28 and second substrate 18. Reflective layer 24 formed on first recording layer 22 is semitransparent so that a laser beam can be irradiated from the first substrate side.

In the recordable DVD shown in FIG. 2, when recording information on first recording layer 22, a laser beam 32 for recording is irradiated toward first recording layer 22 from the edge surface 14a of first substrate 14 and an image is formed by laser beam 32 on first recording layer 22 to form information (bits). At this time, information is recorded on the portion corresponding to groove 34 of first pregroove 12.

When recording information on second recording layer 28, the laser beam for recording is irradiated toward second recording layer 28 from the edge surface 14a of first substrate 14 and an image is formed by laser beam 32 on second recording layer 28 to record information (bits). At this time, information is recorded on the portion corresponding to land 36 of second pregroove 16 in second recording layer 28.

Intermediate layer 20 is a layer that functions to prevent interference between the information recorded on first recording layer 22 and the information recorded on second recording layer 28. Insertion of intermediate layer 20 makes it possible to obtain good recording and reproduction signals with first recording layer 22 and second recording layer 28.

In a recordable DVD capable of two-layer recording on a single side, such as has been set forth above, since the distance of the first recording layer from the entering beam source differs from that of the second recording layer, and their required heat decomposition characteristics and the like vary, the recording materials employed in each of these layers are desirably selected in consideration of their response characteristics and the like. The preferred dye for use as the dye compound in the recording layer nearest to the laser beam source (first recording layer 22 in FIG. 2) is the compound given as the preferred example for the above-described recordable DVD having a single recording layer.

The dye compound for use in the more distant recording layer from the laser beam source (second recording layer 28 in FIG. 2) is desirably a combination of the oxonol dye denoted by general formula (VI) with the cationic part denoted by general formula (III).

An example of a preferred embodiment of a DVD-R optical information recording medium having two recording layers will be given in the form of the optical information recording medium below.

An optical information recording medium in which two laminates each of which comprises a recording layer comprising the dye compound of the present invention and a photoreflective layer on a transparent disklike substrate 0.6±0.1 mm in thickness on which pregrooves have been formed at a track pitch of 0.6 to 0.9 micrometer are adhered together so that recording layers are respectively on the inside and the thickness of the optical information recording medium is 1.2±0.2 mm.

The optical information recording medium of the present invention can be manufactured by the method described below, for example. The substrate (including the protective substrate) can be selected as desired from various materials that are employed as substrates in conventional information recording media. Examples of substrate materials are: glass; polycarbonate; acrylic resins such as polymethyl methacrylate; vinyl chloride-based resins such as polyvinyl chloride and vinyl chloride copolymers; epoxy resin; and amorphous polyolefins and polyesters. These may be combined for use as needed. These materials may be employed as films, or as rigid substrates. Of these materials, polycarbonate is preferred from the perspectives of resistance to moisture, dimensional stability, and cost.

An undercoating layer can be provided on the surface of the substrate on the side on which the recording layer is positioned for the purpose of improving smoothness, enhancing adhesion, and preventing alteration of the recording layer. Examples of the material employed in the undercoating layer are: polymethyl methacrylate, copolymers of acrylic acid and methacrylic acid, copolymers of styrene and maleic anhydride, polyvinyl alcohol, N-methylol acrylamide, copolymers of styrene and vinyl toluene, chlorosulfonated polyethylene, nitrocellulose, polyvinyl chloride, chlorinated polyolefin, polyester, polyimide, copolymers of vinyl acetate and vinyl chloride, copolymers of ethylene and vinyl acetate, polyethylene, polypropylene, polycarbonate, other polymeric substances, and surface modifying agents such as silane coupling agents. After preparing a coating liquid by dissolving the above substance in a suitable solvent, the undercoating layer can be formed by applying the coating liquid to the substrate surface by a coating method such as spin coating, dip coating, or extrusion coating.

Irregularities (pregrooves) denoting information such as tracking grooves or address signals are formed on the substrate (or undercoating layer). The pregrooves are desirably formed at the above-stated track pitch directly on the substrate in the course of injection molding or extrusion molding of a resin material such as polycarbonate. The pregrooves may also be formed by providing a pregroove layer. Examples of materials suitable for use in the pregroove layer are a combination of one or more monomers (or oligomers) from among monoesters, diesters, triesters, and tetraesters of acrylic acid and a photopolymerization initiator. A pregroove layer can be formed, for example, by first applying a mixed liquid of the above-described acrylic acid ester and polymerization initiator on a precisely fashioned base mold (stamper), positioning the substrate on the coating liquid layer, and irradiating ultraviolet radiation through the substrate or base mold to cause the coating layer to be cured, thereby adhering the substrate and the coating layer. Then, the substrate can be removed from the base mold to obtain the pregroove layer.

A recording layer comprising the dye compound of the present invention is provided on the surface on which the pregrooves on the substrate (or undercoating layer) have been formed. Various color fastness-improving agents may be incorporated into the recording layer to further enhance photoresistance. Examples of typical color fastness-improving agents are the metal complexes, diimmonium salts, and aminium salts denoted by general formulas (III), (IV), or (V) described in Japanese Unexamined Patent Publication (KOKAI) Heisei No. 3-224793; the nitroso compounds described in Japanese Unexamined Patent Publication (KOKAI) Heisei Nos. 2-300287 and 2-300288; and the TCNQ derivatives described in Japanese Unexamined Patent Publication (KOKAI) Heisei No. 10-151861.

The recording layer may be formed by dissolving the dye compound of the present invention along with desired quenchers, binders, and the like, in a solvent to prepare a coating liquid, applying the coating liquid to a substrate surface, and drying the coating film that is formed. Examples of solvents for use in the coating liquid for forming the dye recording layer are: esters such as butyl acetate, ethyl lactate, and cellosolve acetate; ketones such as methyl ethyl ketone, cyclohexanone, and methyl isobutyl ketone; chlorinated hydrocarbons such as dichloromethane, 1,2-dichloroethane, and chloroform; amides such as dimethyl formamide; hydrocarbons such as cyclohexanone; ethers such as tetrahydrofuran, ethyl ether, and dioxane; alcohols such as ethanol, n-propanol, isopropanol, n-butanol, and diacetone alcohol; fluorosolvents such as 2,2,3,3-tetrafluoropropanol; and glycol ethers such as ethyleneglycol monomethyl ether, ethyleneglycol monoethyl ether, and propyleneglycol monoethyl ether. These solvents may be employed singly or in combinations of two or more based on the solubility of the compound being employed. Oxidation inhibitors, UV-absorbing agents, plasticizers, lubricants, and various other additives may be further added as needed to the coating liquid.

Examples of binders are: natural organic high-molecular substances such as gelatin, cellulose derivatives, dextran, rosin, and rubber; and synthetic organic polymers such as hydrocarbon resins such as polyethylene, polypropylene, polystyrene, and polyisobutylene; vinyl resins such as polyvinyl chloride, polyvinylidene chloride, and copolymers of polyvinyl chloride and polyvinyl acetate; acrylic resins such as polymethyl acrylate and polymethyl methacrylate; and the initial condensation products of thermosetting resins such as polyvinyl alcohol, chlorinated polyethylene, epoxy resin, butyral resin, rubber derivatives, and phenol formaldehyde resin. When employing a binder in combination as a recording layer material, the quantity of binder employed generally falls within a range of 0.1 to 50-fold, preferably 0.1 to 5-fold, the quantity (by mass) of the total quantity of dye. The dye concentration of the coating liquid thus prepared generally falls within a range of 0.01 to 10 mass percent, preferably a range of 0.1 to 5 mass percent.

Examples of coating methods are spraying, spin coating, dipping, roll coating, blade coating, doctor rolling, and screen printing. The recording layer may be a single layer or multiple layers. The thickness of the recording layer generally falls within a range of 20 to 500 nm, preferably 50 to 300 nm.

To enhance the reflectivity during information reproduction, a reflective layer is generally provided on the recording layer. The photoreflective substance employed as the material of the reflective layer is highly reflective with regard to laser beams. Examples are: Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn, Bi, and other metals, semimetals, and stainless steel. Of these, Cr, Nit Pt, Cu, Ag, Au, Al, and stainless steel are preferred, and Ag is particularly preferred. These substances may be employed singly, in combinations of two or more, or as alloys. The reflective layer can be formed on the recording layer by, for example, vapor deposition, sputtering, or ion plating of the above reflective substance. The thickness of the reflective layer generally falls within a range of 10 to 300 nm, preferably 50 to 200 nm.

A protective layer can be provided on the reflective layer to physically and chemically protect the recording layer and the like. The protective layer can also be provided on the side of the substrate on which no recording layer is provided to enhance scratch resistance and moisture resistance. Examples of the material employed in the protective layer are inorganic substances such as SiO, $SiO_2$, $MgF_2$, $SnO_2$, and $Si_3N_4$; and organic substances such as thermoplastic resins, thermosetting resins, and UV-setting resins. The protective layer can be formed, for example, by laminating a film obtained by plastic extrusion processing on the reflective layer and/or the substrate with an adhesive layer. Alternatively, the protective layer can be provided by vacuum vapor deposition, sputtering, coating, or some other method. Further, when employing a thermoplastic resin or thermosetting resin, it can be dissolved in a suitable solvent to prepare a coating liquid. The coating liquid can then be coated and dried to form a protective layer. When employing a UV-setting resin, it can be employed as is or dissolved in a suitable solvent to prepare a coating liquid, the coating liquid coated, and the coating liquid cured by irradiation with UV light to form a protective layer. Various additives such as antistatic agents, antioxidizing agents, and UV absorbing agents can be added as needed to the coating liquid. The thickness of the protective layer generally falls within a range of 0.1 to 100 micrometers. By means of the above steps, it is possible to prepare a laminate comprising a recording layer, a reflective layer, and, as needed, a protective layer on a substrate. By preparing two laminates as set forth above and adhering them together with adhesive with each recording layer on the inside, an optical information recording medium having two recording layers can be manufactured. Further, the laminate obtained and a disklike protective substrate of roughly identical dimensions with the substrate of the laminate can be adhered together with an adhesive with the recording layer on the inside to produce an optical information recording medium having a single recording layer.

Examples of the material employed in the adhesive layer are: thermoplastic resins, thermosetting resins, electron beam-setting resins, UV-setting resins, pressure sensitive double-sided tape, $SiO_2$, and other inorganic materials. These materials may be employed singly or in combination, and employed not just in single layer, but in multilayer films. The adhesive layer may be formed by spin coating, casting, or sputtering. The thickness of the adhesive layer is preferably 5 to 100 micrometers, more preferably 10 to 70 micrometers.

The method of recording information on the optical information recording medium of the present invention is as follows, for example. First, while rotating the information recording medium at a constant linear speed or constant angular speed, a recording-use laser beam such as a semiconductor laser beam is irradiated from the substrate side. The irradiation of this beam either forms holes at the interface between the recording layer and the reflective layer (holes are formed by deforming the recording layer or reflective layer, or by deforming both layers), by building up the substrate by deformation, or by changing the refractive index by some change in color or associative state in the recording layer, to record information. The recording beam employed is a semiconductor laser beam having an oscillation wavelength falling within a range of 770 to 790 nm for CD-Rs and 600 to 700 nm for DVD-Rs (with 620 to 680 nm being preferable and 630 to 660 nm being more preferable). The information that has thus been recorded can be reproduced by rotating the information recording medium at the same constant linear speed as above, simultaneously irradiating a semiconductor laser having the same wavelength as that employed during recording from the substrate side, and detecting the reflected light.

EXAMPLES

The present invention is further described through Examples below. However, the present invention is not limited to the embodiments shown in Examples.

Example 1

Synthesis of Dye Compound D-1

(1) Synthesis of p-toluene Sulfonate of Compound Example V-1

According to the following reaction scheme, 3 g of ammonium chloride and 30 g of reduced iron were added to 300 mL of isopropanol and the mixture was heat refluxed for 30 minutes. Next, while continuing the heat refluxing, 25.8 g of 4-nitrophenyl-1-imidazole was gradually added. After continuing heat refluxing for another two hours, filtration was conducted while heating to remove the insoluble matter. The isopropanol solution obtained was concentrated and dried.

The product was then purified by silica gel chromatography, yielding 16.0 g of intermediate A. To 20 mL of dimethyl formamide were then added 2.07 g of intermediate A and 3.36 g of DNPV (1,1'-bis(2,4-dinitrophenyl)[4,4']bipyridinium-dichloride), and the mixture was stirred with heating for 2 hours at 90° C.

When the reaction ended, the mixture was allowed to cool and was left to stand overnight. The crystals that precipitated were filtered out, washed with dimethyl formamide, and dried under reduced pressure, yielding 3.0 g of intermediate B. To 2.0 g of intermediate B was then added 20 mL of p-toluenesulfonic acid methyl ester, and the mixture was stirred with heating for 6 hours at 120° C. The mixture was allowed to cool, after which 30 mL of ethyl acetate was added, and stirring was conducted for 30 minutes. The precipitating crystals were filtered out and dried, yielding 2.75 g of p-toluenesulfonate of V-1.

$^1$H-NMR data (d$^6$-DMSO): 9.99 (s, 2H), 9.74 (d, 4H), 9.10 (d, 4H), 8.46 (s, 2H), 8.28 (dd, 8H), 8.05 (s, 2H), 7.48 (d, 8H), 7.12 (d, 8H), 4.03 (s, 6H), 2.30 (s, 12H)

(2) Synthesis of Dye Compound (Formation of Salt)

A 0.58 g quantity of the p-toluenesulfonate of V-1 obtained above was completely dissolved with heating in 30 mL of methanol, 1.24 g of the dye starting material described below were added, and the mixture was stirred for 30 minutes at 60° C.

After cooling, the mixture was stirred for 2 hours at room temperature. The precipitating crystals were filtered out, washed with methanol, and dried, yielding dye compound D-1 (absorbance λ(lamhda)max=561.6 nm, ϵ(epsilon)= 6.13×10$^5$/2,2,3,3-tetrafluoropropanol (TFP)).

$^1$H-NMR data (d$^6$-DMSO): 9.94 (s, 2H), 9.78 (s, 4H), 9.15 (d, 4H), 8.44 (s, 2H), 8.25 (dd, 8H), 8.05 (s, 2H), (7.70-7.47 (m, 12H), 7.20-7.08 (m, 8H), 4.00 (s, 6H), 1.98 (s, 16H), 1.80-1.75 (m, 8H), 1.52 (s, 12H), 1.47-1.32 (m, 8H), 0.88 (t, 12H)

[Chem. 51]

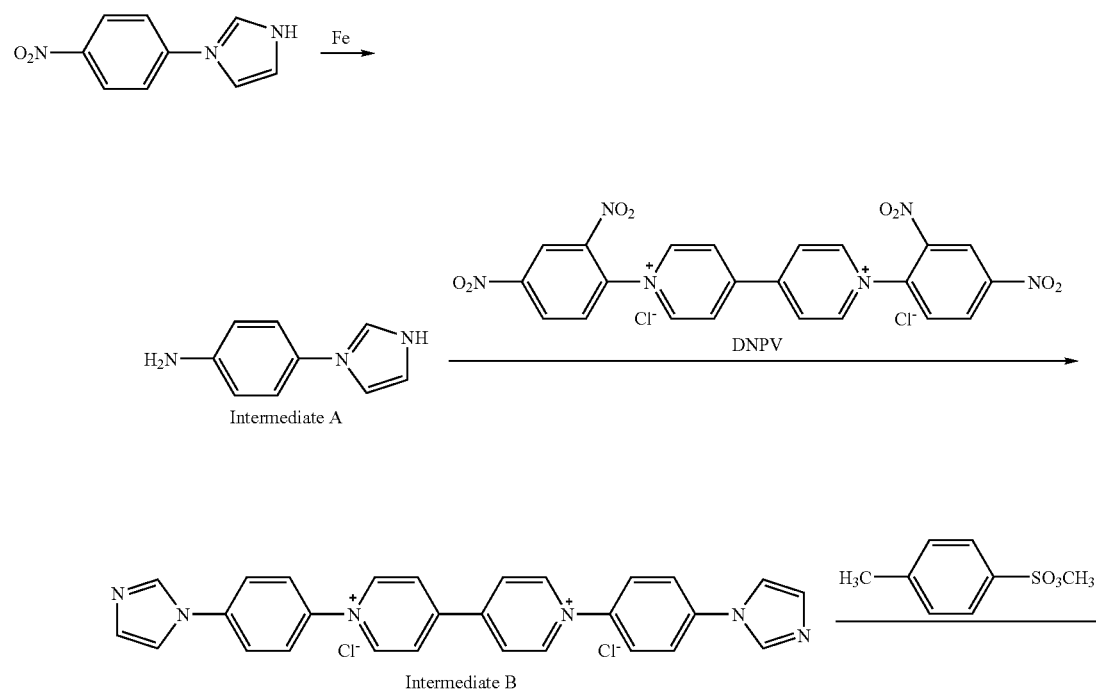

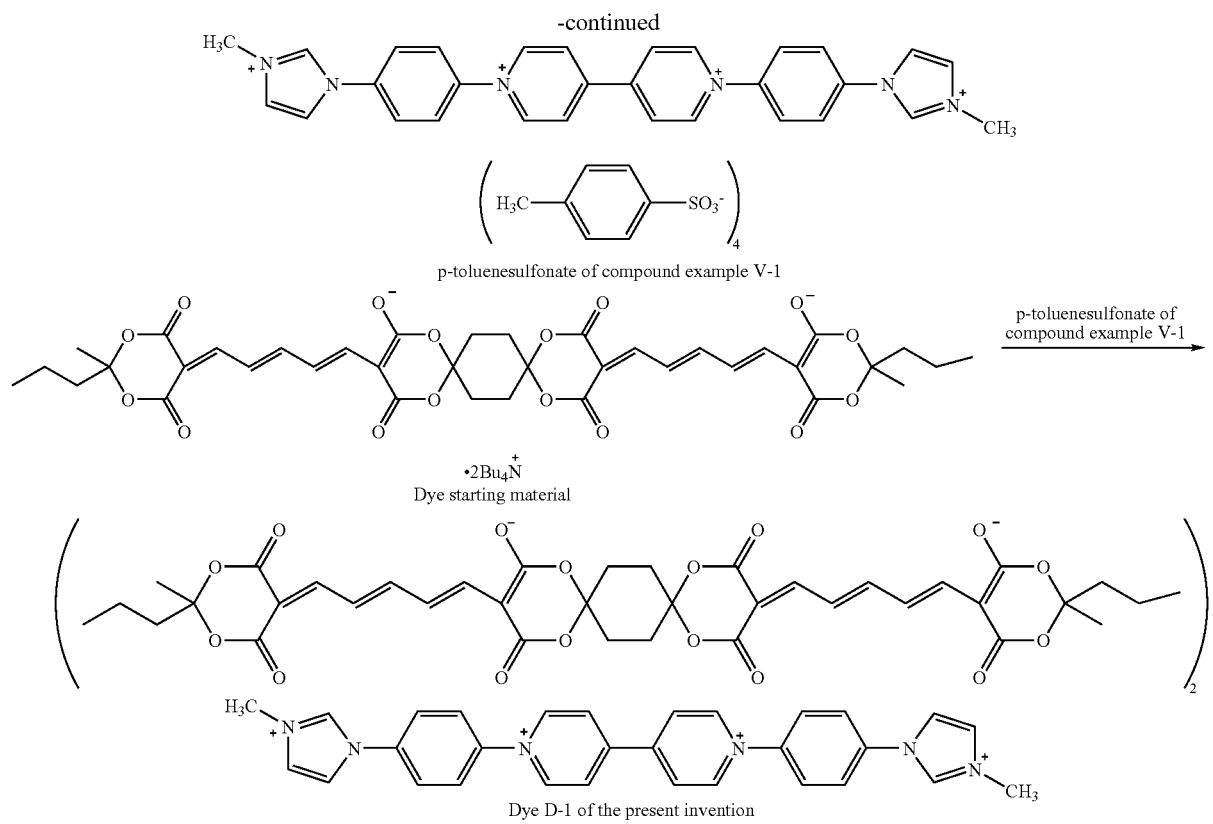

Example 2

Synthesis of Dye Compound D-2

(1) Synthesis of Br⁻, Cl⁻ Mixed Salt of Compound Example V-2

Intermediate B and benzyl bromide were reacted according to the following reaction scheme to synthesize a Br⁻, Cl⁻ mixed salt of compound example V-2.

$^1$H-NMR data (d$^6$-DMSO): 10.32 (s, 2H), 9.80 (d, 4H), 9.17 (d, 4H), 8.53 (s, 2H), 8.32 (d d, 8H), 8.15 (s, 2H), 7.60 (d, 4H), 7.50-7.42 (m, 6H), 5.60 (s, 4H)

(2) Synthesis of Dye Compound (Formation of Salt)

Reaction was conducted with the dye starting material described below in the same manner as in Example 1, yielding dye compound D-2 (absorbanceλ(lambda)max=561.7 nm, ε(epsilon)=6.08×10$^5$/TFP).

$^1$H-NMR data (d$^6$-DMSO): 10.16 (s, 2H), 9.78 (d, 4H), 9.13 (d, 4H), 8.50 (s, 2H), 8.27 (d d, 8H), 8.12 (s, 2H), (7.70-7.41 (m, 22H), 7.20-7.09 (m, 8H), 5.55 (s, 4H), 1.98 (s, 16H), 1.80-1.75 (m, 8H), 1.52 (s, 12H), 1.47-1.32 (m, 8H), 0.88 (t, 12H)

[Chem. 52]

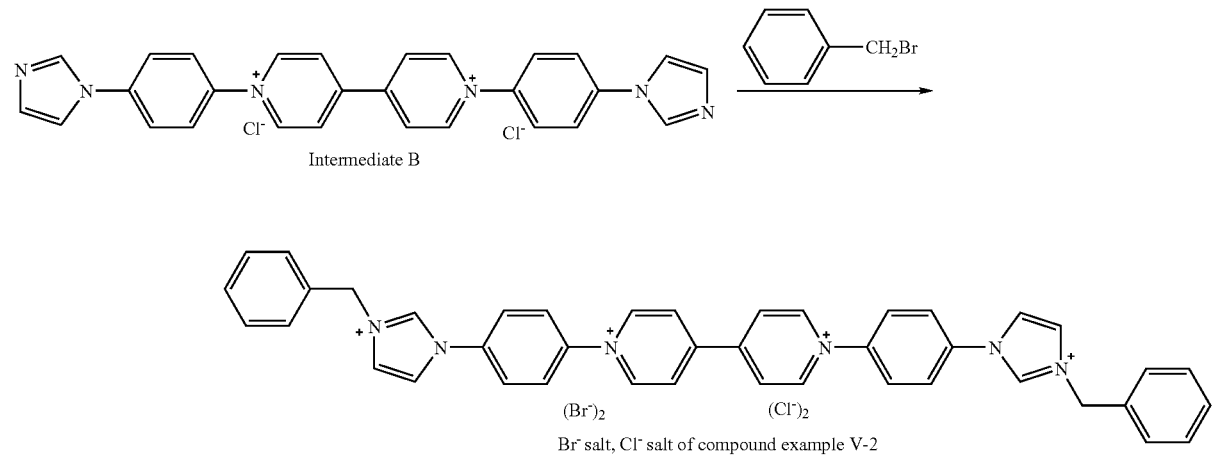

-continued

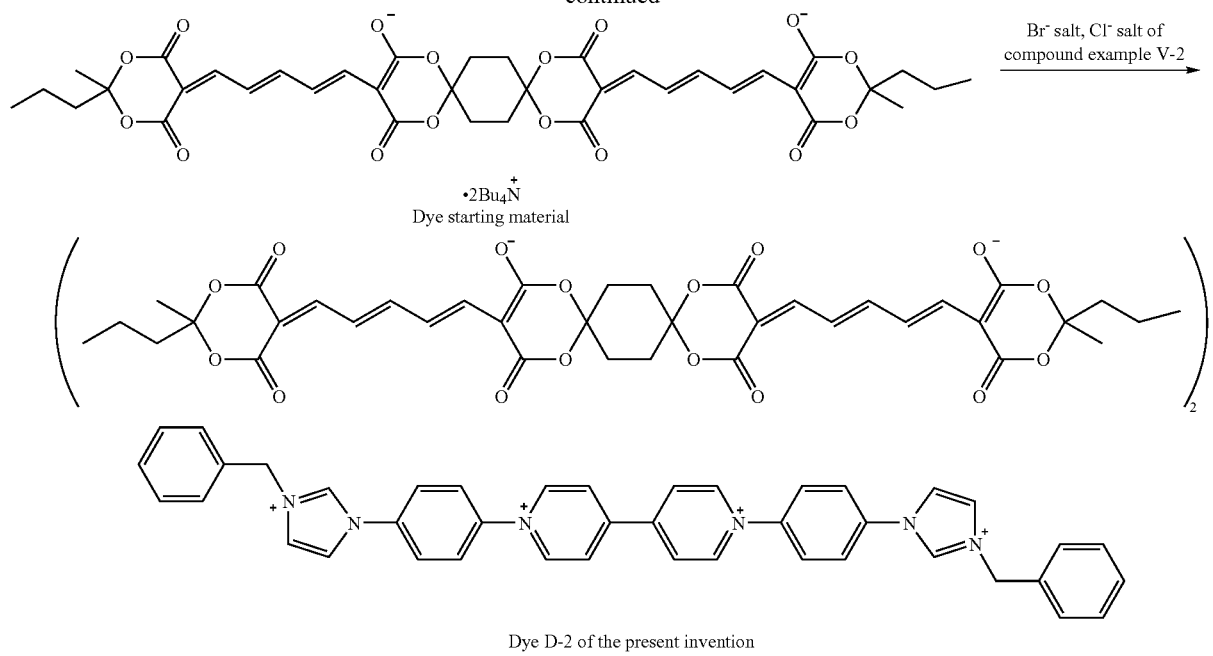

Dye starting material

Dye D-2 of the present invention

Example 3

Synthesis of Dye Compound D-3

(1) Synthesis of p-toluenesulfonate of Dye Compound V-3

Synthesis was conducted according to the following reaction scheme. First, 3.23 g of benzimidazole, 17.3 g of rubidium carbonate, 56 mg of palladium acetate, and tri-t-butylphosphine were added to 50 mL of mesitylene, and the mixture was stirred at 100° C. To this was then gradually added 6.23 g of 1-iodo-4-nitrobenzene. The mixture was heat refluxed for 8 hours and then cooled. Ethyl acetate and water were added and the mixture was extracted with ethyl acetate. The extract was concentrated and purified by column chromatography, yielding 2.4 g of intermediate C. Intermediates D and E were then synthesized by the same operations as in Example 1 and reacted with p-toluenesulfonic acid methyl ester to synthesize the p-toluenesulfonate of compound example V-3.

$^1$H-NMR data (d$^6$-DMSO): 10.30 (s, 2H), 9.81 (d, 4H), 9.17 (d, 4H), 8.39 (d, 4H), 8.29 (d, 4H), 8.22 (d, 2H), 7.92-7.78 (m, 8H), 7.49 (d, 2H), 7.45 (d, 8H), 7.10 (d, 8H), 4.25 (s, 6H), 2.28 (s, 12H)

(2) Synthesis of Dye Compound (Formation of Salt)

Reaction with the following starting material was conducted in the same manner as in Example 1, yielding dye compound D-3 (absorbance λ(lambda)max=562.0 nm, ε(epsilon)=5.76×10$^5$/TFP).

$^1$H-NMR data (d$^6$-DMSO): 10.30 (s, 2H), 9.83 (d, 4H), 9.19 (d, 4H), 8.38 (d, 4H), 8.28 (d, 4H), 8.21 (d, 2H), 7.91-7.80 (m, 6H), 7.70-7.45 (m, 12H), 7.20-7.08 (m, 8H), 4.25 (s, 6H), 1.98 (s, 16H), 1.80-1.75 (m, 8H), 1.52 (s, 12H), 1.47-1.32 (m, 8H), 0.88 (t, 12H)

[Chem. 53]

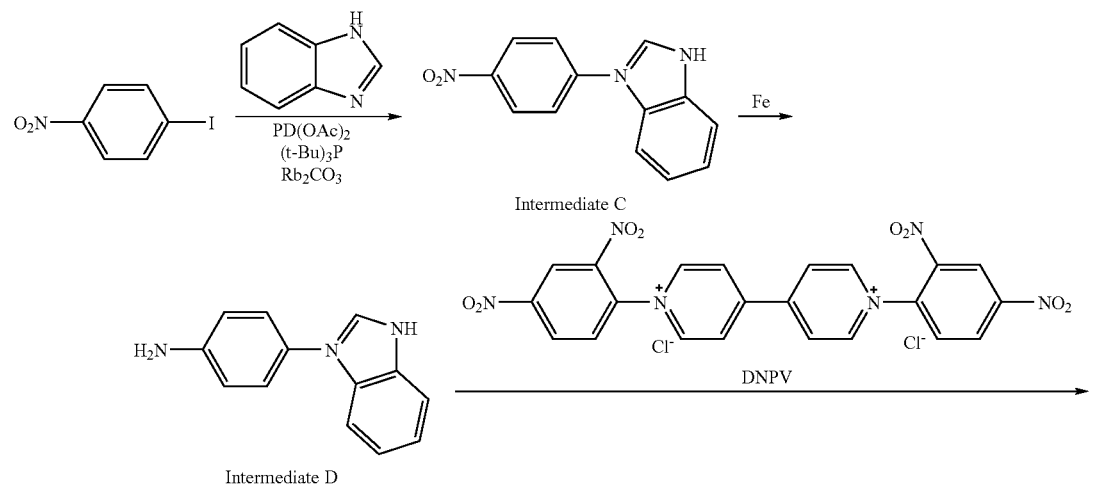

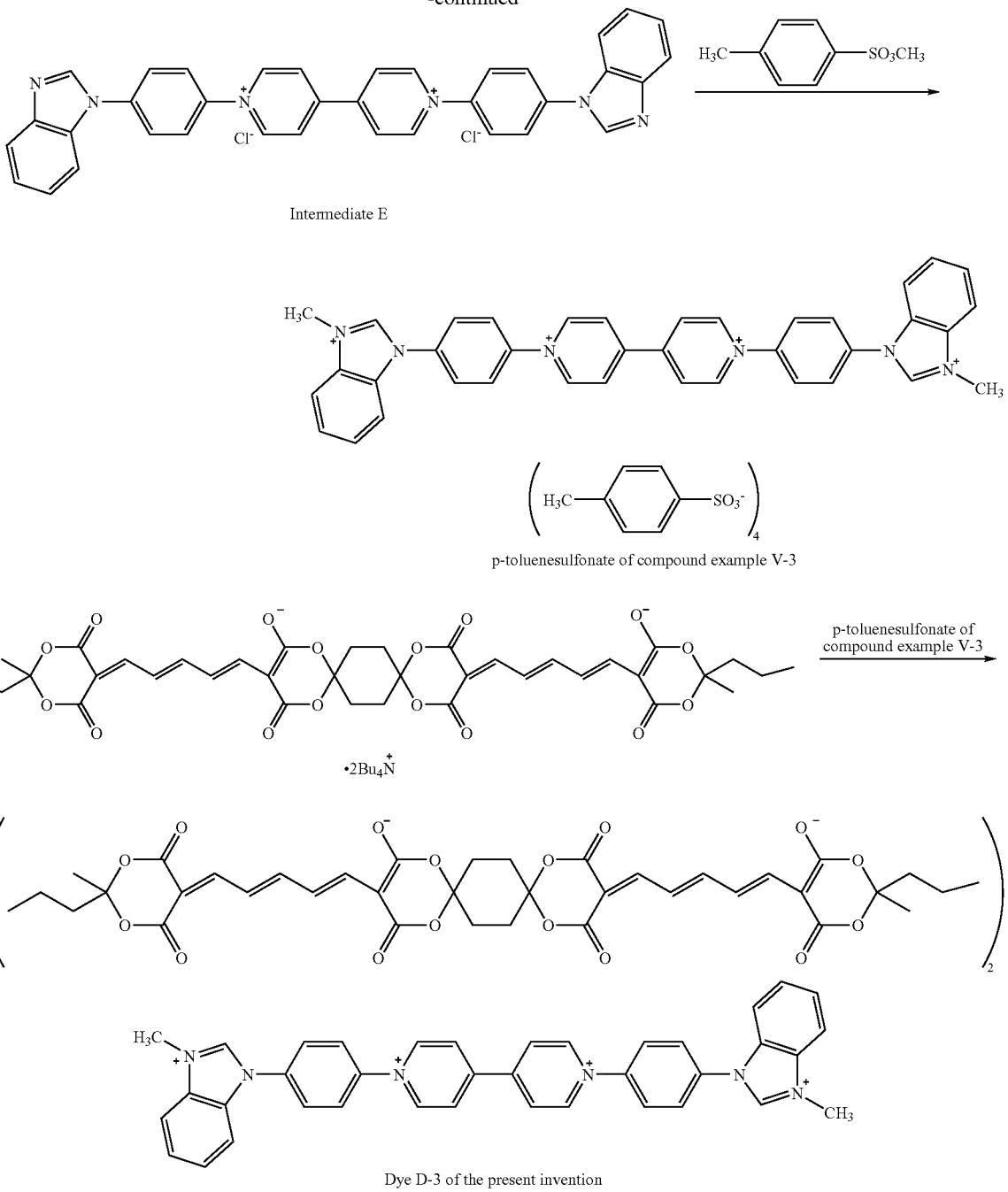

Example 4

Synthesis of Dye Compound D-4

(1) Synthesis of Br⁻, Cl⁻ Mixed Salt of Compound Example V-4

Intermediate E and benzyl bromide were reacted according to the following reaction scheme to synthesize a Br⁻, Cl⁻ mixed salt of compound example V-4.

$^1$H-NMR data (d$^6$-DMSO): 10.68 (s, 2H), 9.88 (d, 4H), 9.23 (d, 4H), 8.40 (dd, 4H), 8.13-8.10 (m, 2H), 7.95-7.91 (m, 2H), 7.83-7.77 (m, 4H), 7.71 (d, 4H), 7.50-7.40 (m, 6H), 5.96 (s, 4H)

(2) Synthesis of Dye Compound (Formation of Salt)

Reaction with the following starting material was conducted in the same manner as in Example 1, yielding dye compound D-4 (absorbanceλ(lambda)max=562.0 nm, ϵ(epsilon)=6.05×10$^5$/TFP).

$^1$H-NMR data (d$^6$-DMSO): 10.53 (s, 2H), 9.84 (d, 4H), 9.19 (d, 4H), 8.38 (dd, 4H), 8.12-8.09 (m, 2H), 7.93-7.90 (m, 2H), 7.80-7.77 (m, 4H), 7.70-7.40 (m, 22H), 7.20-7.08 (m, 8H), 5.93 (s, 4H), 1.98 (s, 16H), 1.80-1.75 (m, 8H), 1.52 (s, 12H), 1.47-1.32 (m, 8H), 0.88 (t, 12H)

[Chem. 54]

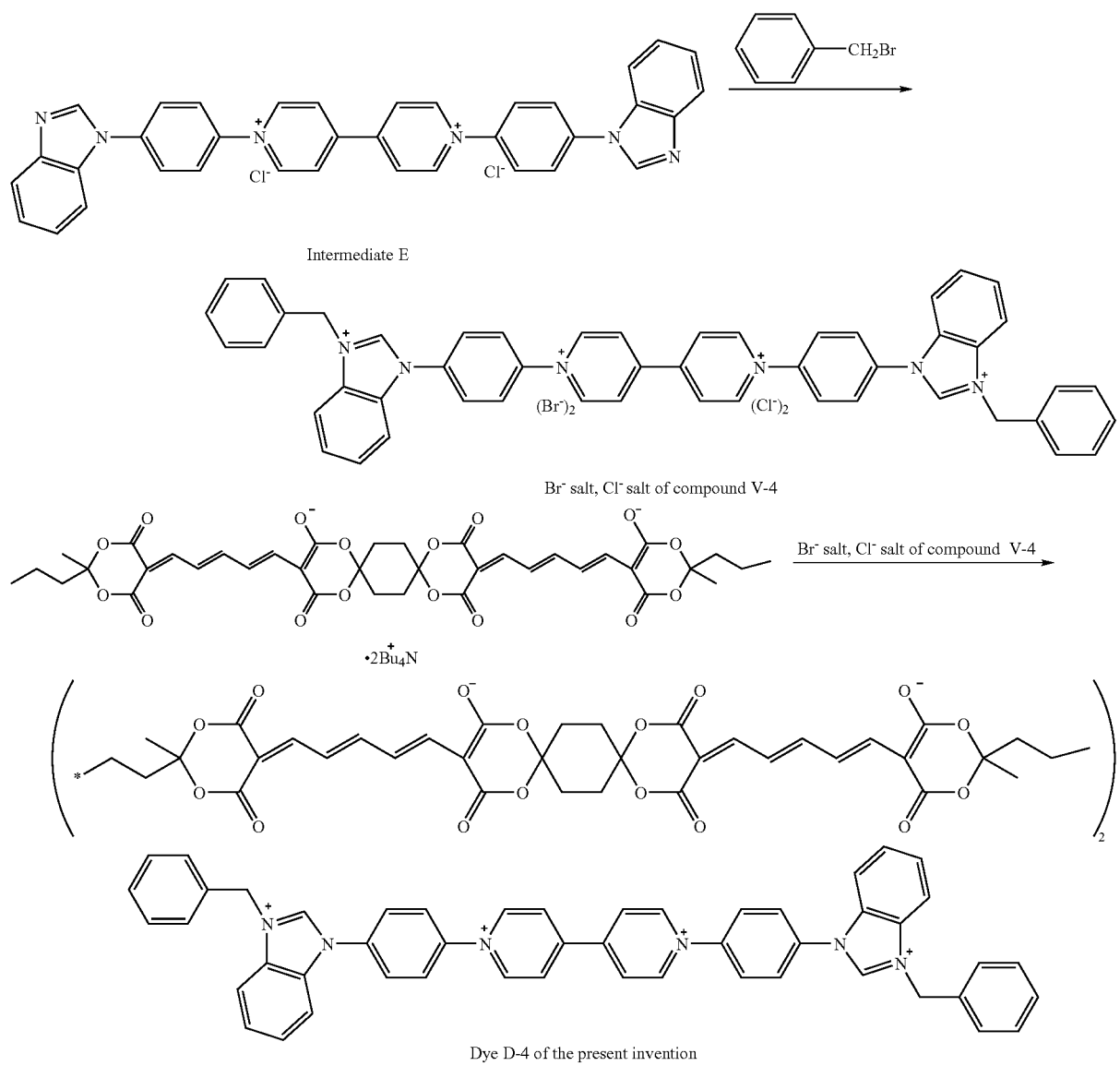

Dye D-4 of the present invention

Example 5

Synthesis of Dye Compound D-53

(1) Synthesis of Hydrochloride of Compound Example V-31

Synthesis was conducted according to the following scheme.

(i) Synthesis of Intermediate F

A 15 g quantity of 4,4'-bipyridyl was dissolved in 100 mL of acetone, 13.2 g of 1-chloro-2,4-dinitrobenzene was added, the mixture was stirred for 15 minutes at room temperature, and the mixture was heat refluxed for 15 hours. When the reaction ended, cooling was conducted to room temperature, and the precipitating crystals were filtered out under reduced pressure. The crystals finally obtained were washed with acetate and dried, yielding 18.8 g of intermediate F.

(ii) Synthesis of Intermediate G

A 14.4 g quantity of intermediate F was suspended in 100 mL of acetonitrile, 4.6 g of aniline was added, and the mixture was heat refluxed for 7 hours. When the reaction ended, cooling was conducted to room temperature. The precipitating crystals were filtered out, washed with acetonitrile, and dried. A 20 mL quantity of methanol was added to the crude crystals that had been obtained, they were dissolved with heating, 200 mL of ethyl acetate was added, and the mixture was stirred for 1 hour at room temperature. The crystals obtained were filtered out, yielding 10.4 g of intermediate G.

(iii) Synthesis of Intermediate H

A 5 mL quantity of N-methylpyrrolidone was added to 3 g of intermediate G and 7 g of 1-chloro-2,4-dinitrobenzene, and the mixture was heated for 9 hours on an oil bath with an external temperature of 110° C. When the reaction ended, cooling was conducted to room temperature. The precipitating crystals were filtered out, washed with N-methylpyrrolidone, further washed with ethyl acetate, and dried, yielding 3.7 g of intermediate H.

(iv) Synthesis of Hydrochloride of Compound Example V-31

A 2.4 g quantity of intermediate H was suspended in 30 mL of dimethyl formamide, 0.4 g of 4,4'-diaminodiphenylether was added, and the mixture was stirred with heating at 100° C. for 6 hours. When the reaction ended, cooling was conducted to room temperature. The precipitating crystals were washed with dimethyl formamide, further washed with ethyl acetate, and dried, yielding 1.16 g of c.

V-27 and hydrochloride of V-72 from compound example V-32 by the same method as that set forth above, and subjecting chlorine anions in the hydrochlorides obtained to anion exchange. As described in the above examples, reaction was conducted with dye starting material to obtain compounds having oxonol dye as paired anions. Identification NMR data are given below for a number of these compounds.

$^1$H-NMR data of hydrochloride of compound example V-41 (CD$_3$OD): 9.58-9.55 (m, 8H), 8.94-8.91 (m, 8H), 7.96-

[Chem. 55]

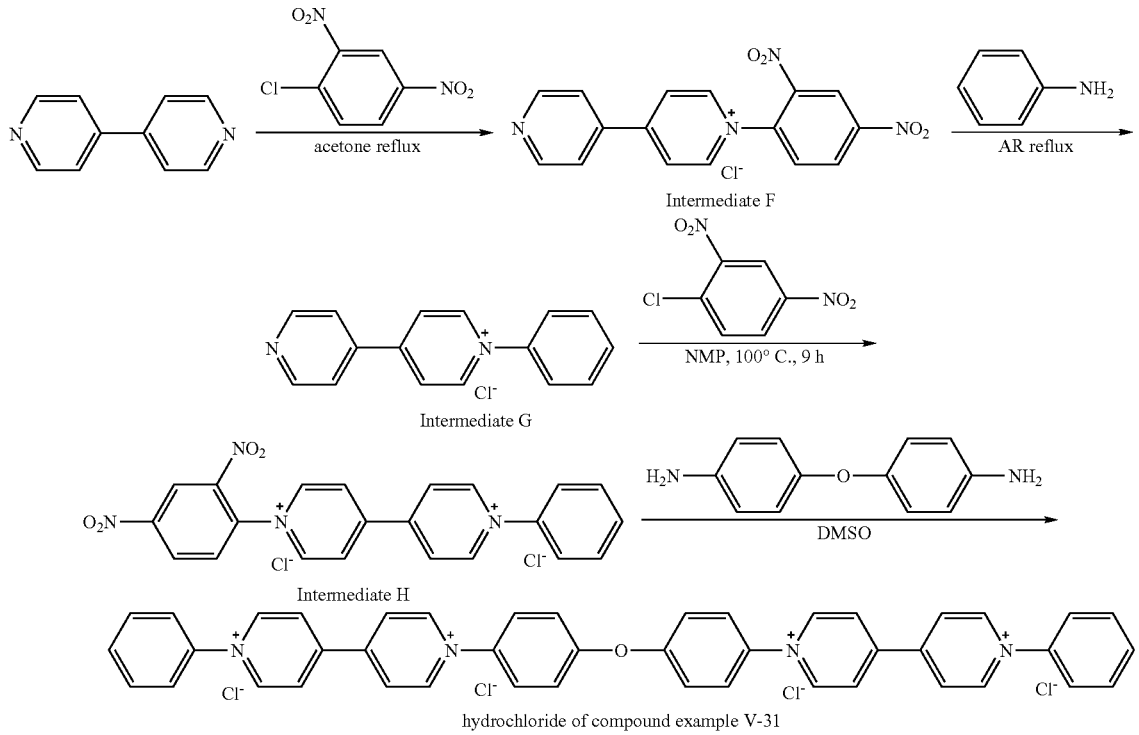

$^1$H-NMR data of hydrochloride of compound example V-31 (CD$_3$OD): 9.62-9.56 (m, 8H), 8.97-8.83 (m, 8H), 8.10-8.06 (m, 4H), 7.97-7.94 (m, 4H), 7.83-7.80 (m, 6H), 7.57-7.53 (m, 4H)

(2) Synthesis of Dye Compound D-53 (Formation of Salt)

A 1.0 g quantity of the hydrochloride of V-31 obtained above was dissolved with heating in 30 mL of methanol, 3.1 g of the dye starting material described in Example 1 was added, and the mixture was stirred for 30 minutes at 60° C. After cooling, the mixture was stirred for 2 hours at room temperature. The precipitating crystals were filtered out, washed with methanol, and dried, yielding 1.8 g of compound D-53 (absorbance λ(lambda)max=561.8 nm, ϵ(epsilon)= 6.07×10$^5$/2,2,3,3-tetrafluoropropanol (TFP)).

$^1$H-NMR data of compound example D-53 (d$^6$-DMSO): 9.70 (s(br), 8H), 9.08 (s(br), 8H), 8.08 (s(br), 4H), 7.98 (s(br), 4H), 7.81 (s(br), 6H), (7.70-7.46 (m, 16H), 7.20-7.08 (m, 8H), 1.99 (s, 16H), 1.80-1.75 (m, 8H), 1.52 (s, 12H), 1.47-1.32 (m, 8H), 0.88 (t, 12H)

Example 6

Synthesis of Dye Compound

Compounds having various anions can be synthesized by synthesizing hydrochloride of V-30 from compound example 7.94 (m, 4H), 7.83-7.78 (m, 8H), 7.73-7.70 (m, 4H), 7.52 (t, 1H), 7.47 (d, 2H), 7.06-7.02 (m, 3H)

$^1$H-NMR data of dye compound D-63 (d$^6$-DMSO): 9.70 (s(br), 8H), 9.07 (s(br), 8H), 7.95 (s(br), 4H), 7.80 (s(br), 8H), (7.70-7.45 (m, 19H), 7.20-7.07 (m, 8H), 7.02-6.98 (m, 3H), 1.98 (s, 16H), 1.81-1.75 (m, 8H), 1.5 (s, 12H), 1.47-1.33 (m, 8H), 0.88 (t, 12H)

$^1$H-NMR data of hydrochloride of compound example V-51 (CD$_3$OD): 9.64 (dd, 8H), 8.98 (dd, 8H), 8.53 (d, 2H), 8.38 (d, 2H), 8.18 (d, 2H), 8.07 (d, 4H), 7.97 (t, 2H), 7.77 (d, 4H), 7.57 (d, 4H), 7.40 (t, 4H), 7.20 (t, 2H)

$^1$H-NMR data of dye compound D-73 (d$^6$-DMSO): 10.53 (s, 2H), 9.77 (d(br), 8H), 9.12 (s(br), 8H), 8.51 (s(br), 2H), 8.39 (s(br), 2H), 8.09 (m(br), 6H), 7.80 (d, 4H), 7.70-7.47 (m, 18H), 7.42 (t, 4H), 7.20-7.09 (m, 8H), 1.98 (s, 16H), 1.80-1.76 (m, 8H), 1.52 (s, 12H), 1.43-1.35 (m, 8H), 0.89 (t, 12H)

$^1$H-NMR data of hydrochloride of compound example V-54 (CD$_3$OD): 9.68-9.55 (m, 8H), 9.00-8.92 (m, 8H), 8.42 (d, 2H), 8.28 (d, 2H), 8.17 (d, 2H), 8.00 (d, 2H), 7.71 (t, 2H), 7.54 (s, 2H), 7.48 (d, 2H), 7.38 (d, 2H), 3.97 (s, 6H)

$^1$H-NMR data of dye compound D-76 (d$^6$-DMSO): 10.98 (s, 1H), 9.73 (s(br), 8H), 9.09 (s(br), 8H), 8.41 (s(br), 2H), 8.20 (s(br), 4H), 8.02 (s(br), 2H), 7.71-7.47 (m, 18H), 7.39 (s(br), 2H), 7.20-7.09 (m, 8H), 3.93 (s, 6H), 1.99 (s, 16H), 1.82-1.77 (m, 8H), 1.53 (s, 12H), 1.47-1.35 (m, 8H), 0.89 (t, 12H)

$^1$H-NMR data of hydrochloride of compound example V-57 (CD$_3$OD): 9.68-9.57 (m, 8H), 9.00-8.92 (m, 8H), 8.42 (d, 2H), 8.29 (d, 2H), 8.17 (d, 2H), 8.02-7.93 (m, 6H), 7.83-7.80 (m, 6H)

$^1$H-NMR data of dye compound D-79 (d$^6$-DMSO): 10.98 (s, 1H), 9.72 (s(br), 8H), 9.10 (s(br), 8H), 8.41 (s(br), 2H), 8.20 (s(br), 4H), 7.99 (s(br), 6H), 7.82 (s(br), 6H), 7.71-7.47 (m, 12H), 7.21-7.08 (m, 8H), 1.99 (s, 16H), 1.82-1.77 (m, 8H), 1.53 (s, 12H), 1.47-1.35 (m, 8H), 0.89 (t, 12H)

Evaluation Method (1) Evaluation of Suitability to Spin Coating

The dyes (0.3 g) described in Table 3 were dissolved in 10 mL of 2,2,3,3-tetrafluoropropanol (TFP) and the solutions obtained were coated by spin coating to polycarbonate substrates. A visual inspection was then conducted for coating striae. The results are given in Table 3.

(2) Test of Dissolution Stability Over Time

The dyes described in Table 3 were prepared as 5.0 mass percent solutions of 2,2,3,3-tetrafluoropropanol and left standing for one week at 20° C. The amount of crystal precipitation was then visually determined. The results are given in Table 3.

⊚: Absolutely no crystal precipitation observed
○: No crystal precipitation observed
Δ: Slight crystal precipitation observed
X: Substantial crystal precipitation observed (3) Measurement of Refractive Index of Dye Film The dye solution (10 mg/1 mL of each dye shown in FIG. 3 in TFP) coated to a glass substrate and the refractive index thereof was measured by ellipsometry. The results are given in Table 3.

TABLE 3

| Dye compound | Coating striae | Dissolution stability over time | Refractive index (660 nm) |
|---|---|---|---|
| D-1 | Not observed | ⊚ | 2.38 |
| D-2 | Not observed | ⊚ | 2.36 |
| D-3 | Not observed | ○ | 2.37 |
| D-4 | Not observed | ○ | 2.33 |
| D-53 | Not observed | ⊚ | 2.30 |
| D-63 | Not observed | ⊚ | 2.30 |
| D-73 | Not observed | ⊚ | 2.27 |
| D-76 | Not observed | ⊚ | 2.31 |
| D-79 | Not observed | ⊚ | 2.30 |
| Comparative compound A | Some striae observed | Δ | 2.24 |
| Comparative compound B | Striae observed | ⊚ | 2.15 |
| Comparative compound C | Some striae observed | X | 2.29 |

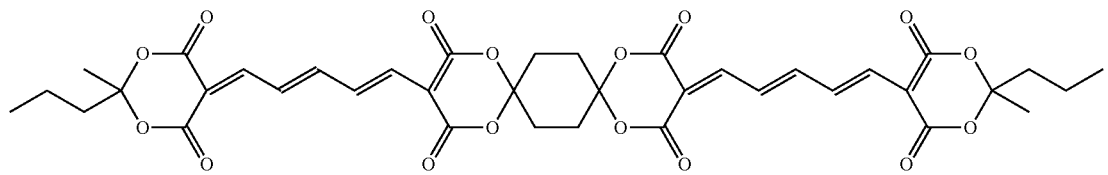

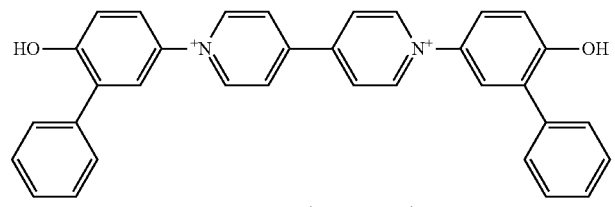

Comparative compound A

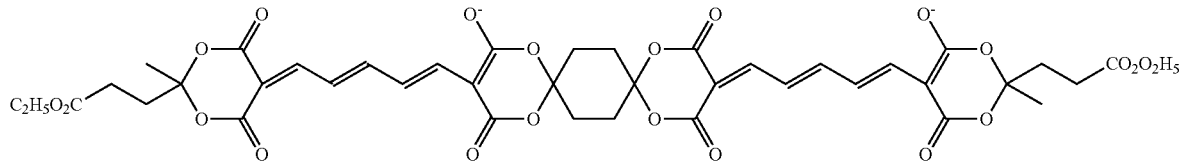

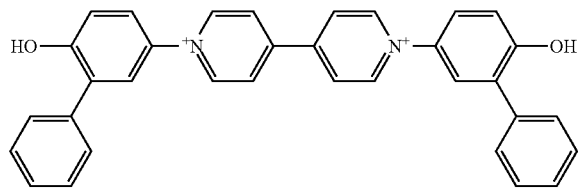

Comparative compound B

TABLE 3-continued

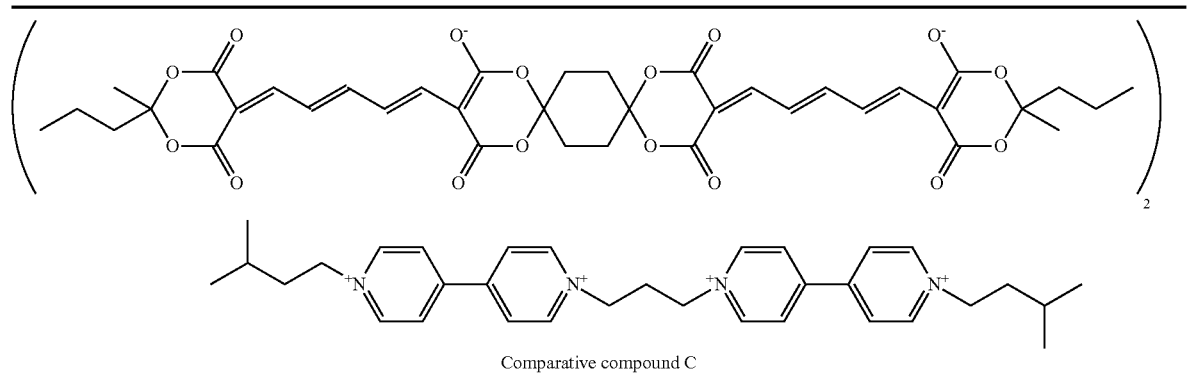

Comparative compound C

As apparent from the results in Table 3, the dye compound of the present invention tended not to develop coating striae and had good dissolution stability over time. It also had a high refractive index. This tendency was similarly observed when other dye compounds of the present invention were employed.

Preparation of Optical Information Recording Medium

Polycarbonate resin was molded by injection molding into a substrate 0.6 mm in thickness and 120 mm in diameter having spiral grooves (130 nm in depth, 310 nm in width, track pitch 0.74 micrometer). A coating liquid was prepared by dissolving 1.25 g of comparative compound A in 100 mL of 2,2,3,3-tetrafluoropropanol, and this coating liquid was coated to the grooved surface of the above substrate above substrate by spin coating to form a dye layer.

Next, silver was sputtered on the dye-coated surface to form a reflective layer about 150 nm in thickness, and then adhered to a dummy substrate 0.6 mm in thickness using an adhesive in the form of a UV-setting resin (Daicure Clear SD640 made by Dainippon Ink and Chemicals, Inc.) to prepare a DVD-R disk.

Evaluation of Optical Information Recording Medium

A DDU1000 and a multisignal generator (made by Pulstec Industrial Co., Ltd.; laser wavelength: 660 nm, aperture rate: 0.60) were employed to record 8-16 modulating signals at equivalent-speed (11.08 Mbps), octuple-speed (88.64 M) and decuple-speed (110.8 Mbps) transfer rates.

The recording strategies used are given in Table 4. The equivalent-speed recording and the decuple-speed recording were each performed using one type of recording strategy, while the octuple-speed recording was performed using two types of recording strategies that varied greatly in pulse width.

The recording power was set so as to minimize the amount of jitter in the recording on each medium. Subsequently, reproduction was conducted with a laser of the same wavelength as that used in recording, and the sensitivity and jitter was measured. The results are given in Table 5. Good recording strategies could be set.

[Table 4]

TABLE 4

| | Recording strategies | | | |
|---|---|---|---|---|
| Recording speed | 1X | 8X | 8X | 10X |
| Recording strategies | A | B | C | D |
| 3Ttop | 1.55 | 2.55 | 1.85 | 2.75 |
| 4Ttop | 1.50 | 2.92 | 2.12 | 3.20 |
| nTtop | 1.55 | 1.70 | 1.30 | 1.90 |
| Tmp | 0.65 | — | — | — |
| nTwt | — | 0.50 | −0.30 | 0.55 |
| nTlp | — | 1.40 | 0.60 | 1.40 |
| 3-nTld | — | −0.03 | −0.05 | −0.03 |
| 3Tdtop | — | −0.15 | −0.05 | −0.15 |
| 4Tdtop | — | 0.20 | 0.35 | 0.20 |
| nTdtop | — | 0.00 | 0.00 | 0.00 |
| 5Ttop2 | — | −0.15 | −0.05 | −0.20 |
| 5Tlp2 | — | −0.10 | −0.15 | −0.20 |
| 5Tdlp2 | — | 0.00 | 0.00 | 0.00 |
| P0/Pm | — | 1.48 | 1.58 | 1.36 |

TABLE 4-continued

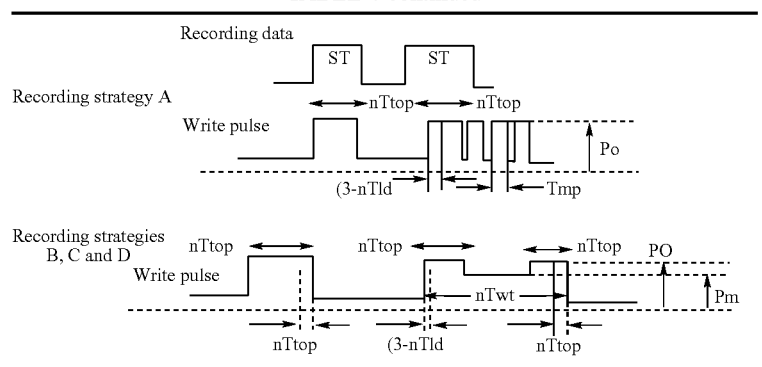

TABLE 5

|  | Examples Recording speed | | | |
|---|---|---|---|---|
|  | 1X | 8X | 8X | 10X |
| Recording strategy | A | B | C | D |
| Optimal recording power (mW) | 10 | 26 | 32 | 32 |
| Refractive index (%) | 51.2 | 52.1 | 51.8 | 51.7 |
| Jitter (%) | 6.7 | 6.8 | 6.9 | 6.9 |
| 14T modulation degree | 0.52 | 0.71 | 0.77 | 0.78 |
| PI error | 23 | 18 | 11 | 16 |
| AR (%) | 50 | 35 | 28 | 26 |

Next, a 12× recording strategy was set with comparative compound A in the same manner as in Tables 4 and 5. Then, DVD-R disks were prepared in the same manner as above, with the exception that the various dyes shown in Table 6 were employed instead of comparative compound A. A 12× recording and reproducing test was conducted using the disks. The results are given in Table 6.

TABLE 6

| Dye compound | Sensitivity (mW) | Jitter (%) |
|---|---|---|
| D-1 | 32 | 6.0 |
| D-2 | 34 | 5.9 |
| D-3 | 33 | 6.2 |
| D-4 | 35 | 6.1 |
| D-53 | 30 | 5.8 |
| D-63 | 33 | 6.1 |
| D-73 | 33 | 5.9 |
| D-76 | 32 | 6.0 |
| D-79 | 31 | 5.8 |
| Comparative compound A | 37 | 7.2 |
| Comparative compound B | 42 | 7.5 |
| Comparative compound C | 50 | 8.5 |

As shown in Table 6, the DVD-R disks employing the dye compounds synthesized in Examples as a dye for recording layer had excellent sensitivity and jitter. As shown in Table 3, they also exhibited high refractive index. This refractive index was of a level capable of achieving adequate recording properties in DL media. As shown in Table 3, the dye compounds synthesized in Examples had excellent manufacturing suitability.

INDUSTRIAL APPLICABILITY

The optical information recording medium of the present invention is suitable as a DVD-R optical information recording medium.

BRIEF DESCRIPTION OF THE DRAWINGS

FIG. 1 A schematic sectional view of a recordable DVD having a single recording layer.

FIG. 2 A schematic sectional view of a recordable DVD having two recording layers.

The invention claimed is:

1. A cationic compound denoted by the following general formula (I):

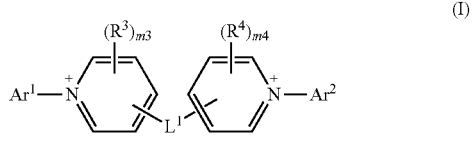

wherein $Ar^1$ and $Ar^2$ each independently denotes an optionally substituted aryl group or aromatic heterocyclic group, $L^1$ denotes a single bond or a divalent linkage group, with at least one from among $Ar^1$, $Ar^2$ and $L^1$ comprising one or more onium cations; $R^3$ and $R^4$ each independently denotes a substituent and may form a ring with a benzene ring substituted; m3 and m4 each independently denotes an integer ranging from 0 to 4, and plural $R^3$s and $R^4$s may be identical or different from each other when m3 and m4 are an integer ranging from 2 to 4;

and further wherein, in said general formula (I), $Ar^1$ is denoted by:

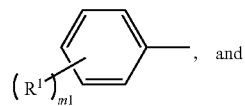, and $Ar^2$ is denoted by:

wherein $R^1$ and $R^2$ each independently denotes a substituent and may form a ring with a benzene ring substituted; one of m1 and m2 denotes an integer ranging from 0 to 5 and the other denotes an integer ranging from 1 to 5, and plural $R^1$s and $R^2$s may be identical or different from each other when m1 and m2 are an integer ranging from 2 to 5;

at least one from among $R^1$ and $R^2$ denotes a substituent comprising a nitrogen cation; and said nitrogen cation is a tetra-substituted nitrogen atom cation or nitrogen atom-containing aromatic heterocyclic cation.

2. The cationic compound according to claim 1, wherein, in said general formula (I), $L^1$ is a single bond.

3. The cationic compound according to claim 1, wherein said nitrogen atom-containing aromatic heterocyclic cation is a pyridinium cation, imidazolium cation, thiazolium cation, oxazolium cation, or iminium cation.

4. The cationic compound according to claim 1, wherein, in general formula (I), $L^1$ is denoted by:

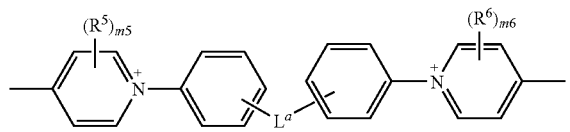

wherein $R^5$ and $R^6$ each independently denotes a substituent; m5 and m6 each independently denotes an integer ranging from 0 to 4, and plural $R^5$s and $R^6$s may be identical or different from each other when m5 and m6 are an integer ranging from 2 to 4.

5. The cationic compound according to claim 1, wherein the compound denoted by said general formula (I) is a compound denoted by the following general formula (IV):

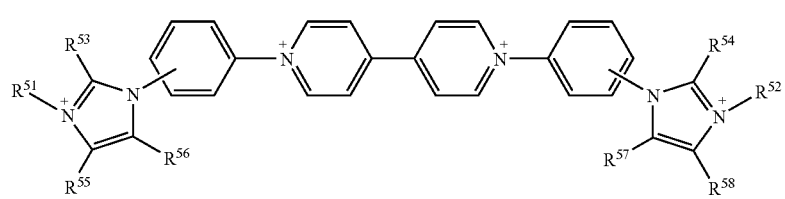

wherein $R^{51}$ and $R^{52}$ each independently denotes a hydrogen atom or alkyl group; $R^{53}$, $R^{54}$, $R^{55}$, $R^{56}$, $R^{57}$, and $R^{58}$ each independently denotes a hydrogen atom, alkyl group, aryl group, or aromatic heterocyclic group, it being permissible for $R^{55}$ and $R^{56}$, and $R^{57}$ and $R^{58}$, to be linked, forming a five or six-membered ring, and $R^{51}$, $R^{52}$, $R^{53}$, $R^{54}$, $R^{55}$, $R^{56}$, $R^{57}$, and $R^{58}$ each may be further substituted.

6. A dye compound comprising the cationic compound according to claim 1 and an anion in an amount capable of neutralizing the charge of said cationic compound.

7. The dye compound according to claim 6, wherein said anion is an anionic dye.

8. The dye compound according to claim 7, wherein said anionic dye is an oxonol dye.

9. The dye compound according to claim 8, wherein said oxonol dye is denoted by the following general formula (V):

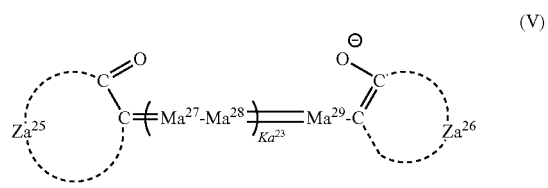

wherein $Za^{25}$ and $Za^{26}$ each independently denotes an atom group forming an acidic nucleus; $Ma^{27}$, $Ma^{28}$, and $Ma^{29}$ each independently denotes a substituted or unsubstituted methine group; $Ka^{23}$ denotes an integer ranging from 0 to 3, and plural $Ma^{27}$s and $Ma^{28}$s may be identical or different from each other when $Ka^{23}$ is 2 or 3.

10. The dye compound according to claim 8, wherein said oxonol compound is denoted by the following general formula (VI):

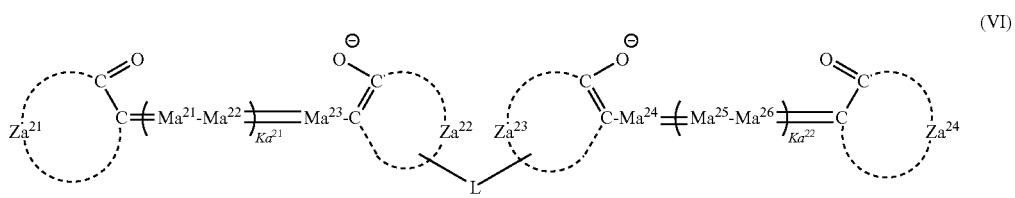

wherein $Za^{21}$, $Za^{22}$, $Za^{23}$, and $Za^{24}$ each independently denotes an atom group forming an acidic nucleus; $Ma^{21}$, $Ma^{22}$, $Ma^{23}$, $Ma^{24}$, $Ma^{25}$, and $Ma^{26}$ each independently denotes a substituted or unsubstituted methine group; L denotes a divalent linkage group that does not form a pi-conjugation with two bonds, and plural $Ma^{21}$s, $Ma^{22}$s, $Ma^{25}$s, and $Ma^{26}$s may be identical or different from each other when $Ka^{21}$ and $Ka^{22}$ are 2 or 3.

11. An optical information recording medium comprising a recording layer on a substrate, wherein said recording layer comprises the dye compound according to claim 6.

12. A cationic compound denoted by the following general formula (I):

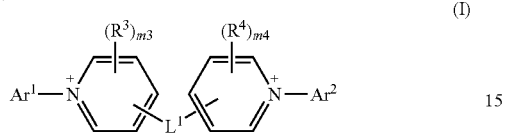

(I)

wherein $Ar^1$ and $Ar^2$ each independently denotes an optionally substituted aryl group or aromatic heterocyclic group, $L^1$ denotes a single bond or a divalent linkage group, with at least one from among $Ar^1$, $Ar^2$ and $L^1$ comprising one or more onium cations; $R^3$ and $R^4$ each independently denotes a substituent and may form a ring with a benzene ring substituted; m3 and m4 each independently denotes an integer ranging from 0 to 4, and plural $R^3$s and $R^4$s may be identical or different from each other when m3 and m4 are an integer ranging from 2 to 4;

and further wherein the compound denoted by said general formula (I) is a compound denoted by the following general formula (IV):

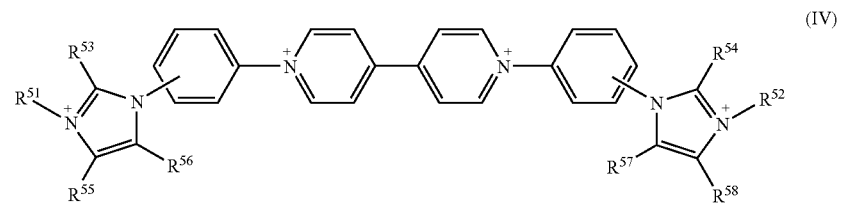

(IV)

wherein $R^{51}$ and $R^{52}$ each independently denotes a hydrogen atom or alkyl group; $R^{53}$, $R^{54}$, $R^{55}$, $R^{56}$, $R^{57}$, and $R^{58}$ each independently denotes a hydrogen atom, alkyl group, aryl group, or aromatic heterocyclic group, it being permissible for $R^{55}$ and $R^{56}$, and $R^{57}$ and $R^{58}$, to be linked, forming a five or six-membered ring, and $R^{51}$, $R^{52}$, $R^{53}$, $R^{54}$, $R^{55}$, $R^{56}$, $R^{57}$, and $R^{58}$ each may be further substituted.

* * * * *